United States Patent
Rabinowitz et al.

(10) Patent No.: US 10,646,475 B2
(45) Date of Patent: *May 12, 2020

(54) SHMT INHIBITORS

(71) Applicant: The Trustees of Princeton University, Princeton, NJ (US)

(72) Inventors: Joshua D. Rabinowitz, Princeton, NJ (US); Hahn Kim, Princeton, NJ (US); Gregory S. Ducker, Rocky Hill, NJ (US); Jonathan M. Ghergurovich, Philadelphia, PA (US)

(73) Assignee: The Trustees of Princeton University, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/552,442

(22) PCT Filed: Mar. 10, 2016

(86) PCT No.: PCT/US2016/021870
§ 371 (c)(1),
(2) Date: Aug. 21, 2017

(87) PCT Pub. No.: WO2016/145252
PCT Pub. Date: Sep. 15, 2016

(65) Prior Publication Data
US 2018/0117010 A1    May 3, 2018

Related U.S. Application Data

(60) Provisional application No. 62/131,205, filed on Mar. 10, 2015.

(51) Int. Cl.
| | |
|---|---|
| A61K 31/519 | (2006.01) |
| A61K 45/06 | (2006.01) |
| A61P 37/00 | (2006.01) |
| A61P 35/00 | (2006.01) |
| A61K 31/19 | (2006.01) |
| A61K 31/4162 | (2006.01) |

(52) U.S. Cl.
CPC .......... *A61K 31/4162* (2013.01); *A61K 31/19* (2013.01); *A61K 31/519* (2013.01); *A61K 45/06* (2013.01); *A61P 35/00* (2018.01); *A61P 37/00* (2018.01)

(58) Field of Classification Search
CPC .. A61K 31/4162; A61K 31/19; A61K 31/519; A61K 45/06; A61P 37/00; A61P 35/00
USPC ........................................................ 514/407
See application file for complete search history.

(56) References Cited

U.S. PATENT DOCUMENTS

| | | | |
|---|---|---|---|
| 4,918,074 A | 4/1990 | Tsuda et al. | |
| 9,480,259 B2 | 11/2016 | Witshel et al. | |
| 10,077,273 B2 * | 9/2018 | Rabinowitz | ........ C07D 491/052 |
| 2018/0072751 A1 | 3/2018 | Rabinowitz et al. | |
| 2018/0354964 A1 | 12/2018 | Rabinowitz et al. | |

FOREIGN PATENT DOCUMENTS

| | | |
|---|---|---|
| WO | WO 2005/012577 A1 | 2/2005 |
| WO | WO 2012/078902 A2 | 6/2012 |
| WO | WO 2013/096820 A1 | 6/2013 |
| WO | WO 2013/182472 A1 | 12/2013 |
| WO | WO 2016/007905 A1 | 1/2016 |
| WO | WO 2016/145252 A1 | 9/2016 |

OTHER PUBLICATIONS

International Search Report and Written Opinion of International Application No. PCT/US2016/021870, entitled: "SHMT Inhibitors," dated May 13, 2016.

Kamel, M. M., "Convenient Synthesis, Characterization, Cytotoxicity and Toxicity of Pyrazole Derivatives," *Acta Chim. Slov.*, vol. 62; 136-151 (2015).

Sirotnak, F. M., et al., "Optimization of High-Dose Methotrexate with Leucovorin Rescue Therapy in the L1210 Leukemia and Sarcoma 180 Murine Tumor Models," *Cancer Research*, vol. 38; 345-353 (1978).

Yan, C., et al., "Discovery and characterization of small molecules that target the GTPase Ral," *Nature*, vol. 515; 443-447 (2014).

Antle, V.D., et al. "Substrate specificity of glycinamide ribonucleotide synthetase from chicken liver", *J. Biol. Chem.* 271(14):8192-8195 (1996).

Ben-Sahra I., et al., "mTORC1 induces purine synthesis through control of the mitochondrial tetrahydrofolate cycle", *Science* 351(6274): 728-732 (2016).

Cader, M.Z., et al. :Crystal structure of human wildtype and S581L-mutant glycyl-tRNA synthetase, an enzyme underlying distal spinal muscular atrophy, *FEBS Lett.* 581(16):2959-2964 (2007).

Clasquin, M.F., et al., "LC-MS Data Processing with MAVEN: a Metabolomic Analysis and Visualization Engine", *Curr. Protoc. Bioinformatics* Ch. 14, Unit 14.11, doi: 10.1002/0471250953. bi1411s37 (2012).

Cockrell, G.M., et al. "New Paradigm for Allosteric Regulation of *Escherichia coli* Aspartate Transcarbamoylase", *Biochemistry* 52(45):8036-8047 (2013).

(Continued)

*Primary Examiner* — Yevgeny Valenrod
(74) *Attorney, Agent, or Firm* — Hamilton, Brook, Smith & Reynolds, P.C.

(57) ABSTRACT

The present invention relates to a method for the treatment of cancer or an autoimmune disorder, comprising the administration of a serine hydroxymethyltransferase (SHMT) inhibitor, and in particular the administration of pyrazolopyran compounds of Formula (VI) as presently described, wherein the compounds are capable of inhibiting a mammalian SHMT, such as human SHMT1 and/or SHMT2. The treatment method further comprises the optional administration of an additional agent as a rescue therapy to reduce toxicity, wherein said agent may be chosen from formate, a formate salt, folinic acid, formate ester, or leucovorin.

23 Claims, 9 Drawing Sheets

(56) References Cited

OTHER PUBLICATIONS

Figure 2:
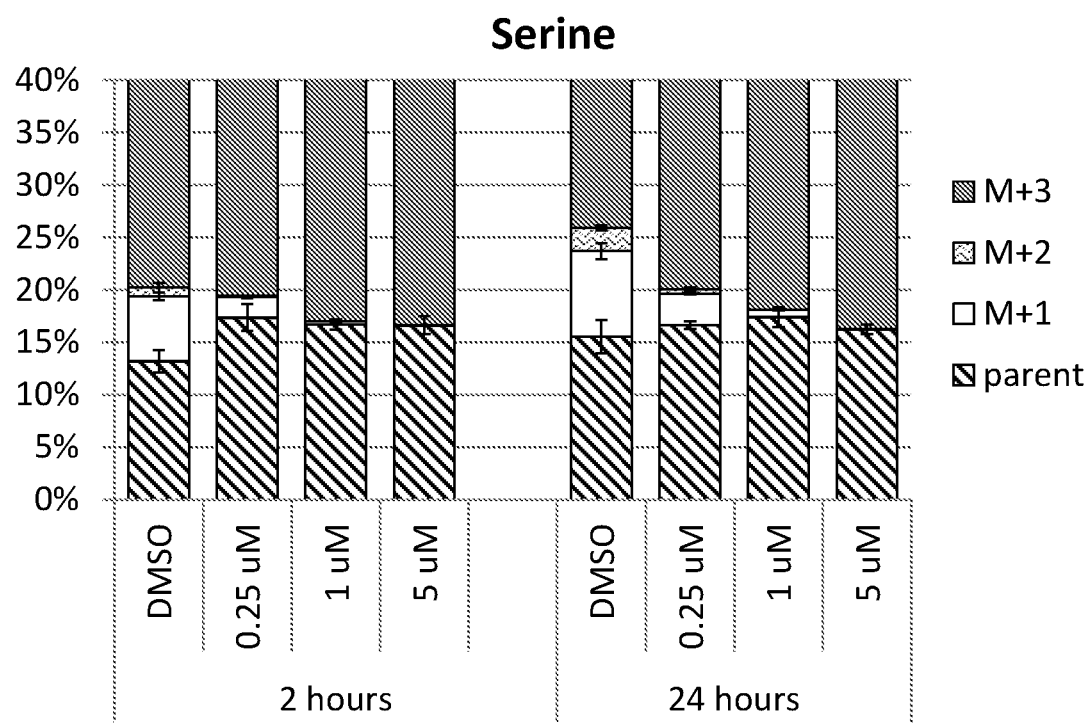

Ducker, G.S., et al., "One-Carbon Metabolism in Health and Disease", Cell Metab. 25, 27-42 (2017).
Ducker, G.S., et al., "Reversal of cytosolic One-Carbon Flux Compensates for Loss of the Mitochondrial Folate Pathway", Cell Metab. 23:1140-1153 (2016).
Eggert, U.S., et al. "Parallel Chemical Genetic and Genome-Wide RNAi Screens Identify Cytokinesis Inhibitors and Targets", Plos Biol 2(12):e379-9 (2004).
Farber, S. "Temporary remissions in acute leukemia in children produced by folid acid antagonist, 4-aminopteroyl-glutamic acid (aminopterin)", New England Journal of Medicine 238(787-793):1-7 (1948).
Ginman, T., et al., Core Refinement toward Permeable β-Secretase (BACE-1) Inhibitors with Low HERG Activity, J. Med. Chem. 56(11): 4181-4205 (2013).
Guertin, D.A., et al. "Ablation in mice of the mTORC components raptor, rictor, or mLST8 reveals that mTORC2 is required for signaling to Akt-FOXO and PKCalpha, but not S6K1", Dev. Cell 11(6):859-871 (2006).
Harvey, R.J., Yee BK "Glycine transporters as novel therapeutic targets in schizophrenia, alcohol dependence and pain", Nat. Rev. Drug Discov. 12(11):866-885 (2013).
International Preliminary Report on Patentability for International Application No. PCT/US2016/021870, "SHMT Inhibitors", dated May 13, 2016.
Jain M., et al. "Metabolite Profiling Identifies a Key Role for Glycine in Rapid Cancer Cell Proliferation", Science 336(6084):1040-1044 (2012).
Kiriyama, Y., et al. "Biochemical characterization of U937 cells resistant to L-asparaginase: the role of asparagine synthetase", Leukemia 3(4):294-297 (1989).
Komykhov, S.A., et al., "The Reaction of Amino-Imidazoles, -Pyrazoles and -Triazoles with α-β-Unsaturated Nitriles", J. Heterocyclic Chem. 42(6): 1111-1116 (2005).
Labuschagne, C.F., et al., "Serine, but Not Glycine, Supports One-Carbon Metabolism and Proliferation of Cancer Cells", CellReports 7, 1248-1258 (2014).
Lamarre, S.G., et al., "An isotope-dilution, GC-MS assay for formate and its application to human and animal metabolism", Amino Acids 46: 1885-1891 (2014).
Lee, G.Y., et al. "Comparative oncogenomics identifies PSMB4 and SHMT2 as potential cancer driver genes", Cancer Res. 74(11):3114-3126 (2014).
Lewis, C.A., et al. "Tracing compartmentalized NADPH metabolism in the cytosol and mitochondria of Mammalian cells" Mol. Cell 55(2):253-263 (2014).
Loayza-Puch, F., et al. "Tumour-specific proline vulnerability uncovered by differential ribosome codon reading", Nature 530(7591):490-494 (2016).
Locasale, J.W., et al. "Phosphoglycerate dehydrogenase diverts glycolytic flux and contributes to oncogenesis" Nat. Genet. 43(9):869-874 (2011).
Longley, D.B., et al., "5-Fluorouracil: mechanisms of action and clinical strategies" Nat. Rev. Cancer 3(5):330-338 (2003).
Lu, W., et al., "Metabolomic Analysis via Reversed-Phase Ion-Pairing Liquid Chromatography Coupled to a Stand Alone Orbitrap Mass Spectrometer", Anal. Chem. 82: 3212-3221 (2010).
Ma, E.H., et al., "Serine Is an Essential Metabolite for Effector T Cell Expansion," Cell Metab. 25, 345-357 (2017).
Marani, M., et al., "A pyrazolopyran derivative preferentially inhibits the activity of human cytosolic serine hydroxymethyltransferase and induces cell death in lung cancer cells", Oncotarget 7(4):4570-4583 (2016).
Mullarky, E., et al., "Identification of a small molecule inhibitor of 3-phosphoglycerate dehydrogenase to target serine biosynthesis in cancers", Proc. Natl Acad. Sci. USA 113(7):1778-1783 (2016).
Nilsson, R., et al., Metabolic enzyme expression highlights a key role for MTHFD2 and the mitochondrial folate pathway in cancer. Nat. Commun. 5:3128 (2014).
Nixon, P.F., "Folinic Acid: Pharmacokinetics and Pharmacodynamics", Clinical and Experimental Pharmacology & Physiology Suppl. 5, pp. 35-41 (1979).
Njalsson, R., et al. "Cooperative Binding of γ-Glutamyl Substrate to Human Glutathione Synthetase", Biochemical and Biophysical Research Communications 289(1):80-84 (2001).
Pacold, M.E., et al. "A PHGDH inhibitor reveals coordination of serine synthesis and one-carbon unit fate", Nat. Chem. Biol. 12(6):452-458 (2016).
Patel, H., et al., "Mammalian fibroblasts lacking mitochondrial NAD+-dependent methylenetetrahydrofolate dehydrogenase-cyclohydrolase are glycine auxotrophs", J. Biol. Chem. 278(21):19436-19441 (2003).
Pavlova, N.N., et al., "The Emerging Hallmarks of Cancer Metabolism", Cell Metab. 23(1):27-47 (2016).
Possemato, R., et al. "Functional genomics reveal that the serine synthesis pathway is essential in breast cancer", Nature 476(7360):346-350 (2011).
Pui, C.-H., et al., "Treatment of acute lymphoblastic leukemia", N. Engl. J. Med. 354(2):166-178 (2006).
Ran, F.A., et al., "Double nicking by RNA-guided CRISPR Cas9 for enhanced genome editing specificity", Cell 154: 1380-1389 (2013).
Ran, F.A., et al., "Genome engineering using the CRISPR-Cas9 system", Nat. Protoc. 8, 2281-2308 (2013).
Schulze, A., Harris, A.L. "How cancer metabolism is tuned for proliferation and vulnerable to disruption", Nature 491(7424):364-373 (2012).
Tibbetts, A.S., et al., "Compartmentalization of Mammalian Folate-Mediated One-Carbon Metabolism", Annu. Rev. Nutr. 30(1):57-81 (2010).
Wang, Q., et al. "Rational Design of Selective Allosteric Inhibitors of PHGDH and Serine Synthesis with Anti-tumor Activity", Cell Chem. Biol. 24(1):55-65 (2017).
Witschel, M.C., et al. "Inhibitors of plasmodial serine hydroxymethyltransferase (SHMT): cocrystal structures of pyrazolopyrans with potent blood- and liver-stage activities" J. Med. Chem. 58(7):3117-3130 (2015).
Zhao, R., et al., "Resistance to antifolates", Oncogene (2003) 22,7431-7457.
Notice of Allowance for U.S. Appl. No. 15/705,200, entitled: "SHMT Inhibitors," dated May 7, 2018.
Non-Final Office Action for U.S. Appl. No. 16/103,375, entitled: "SHMT Inhibitors," dated Feb. 26, 2019.

\* cited by examiner

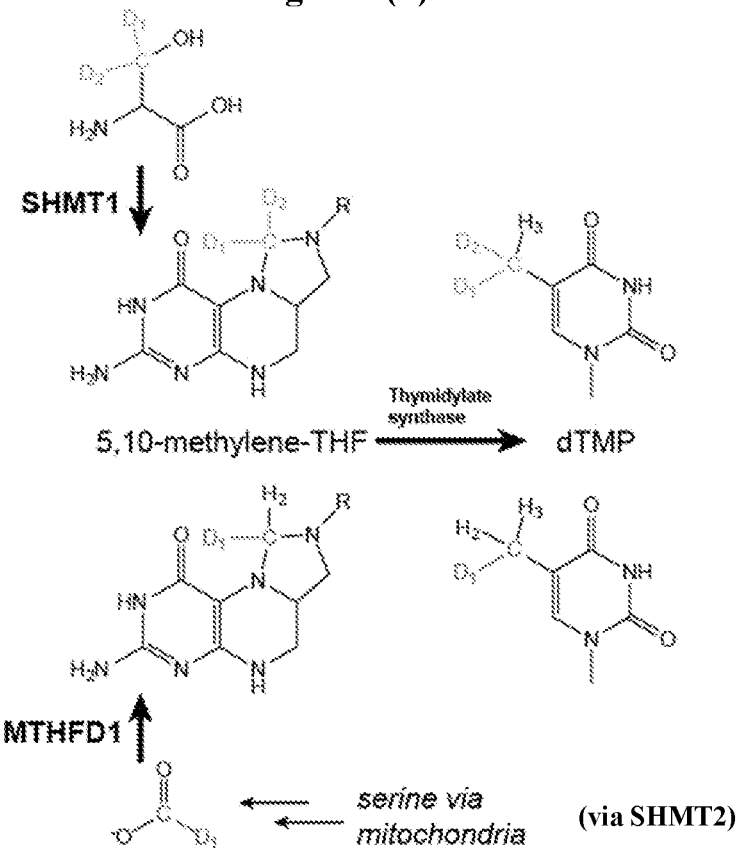
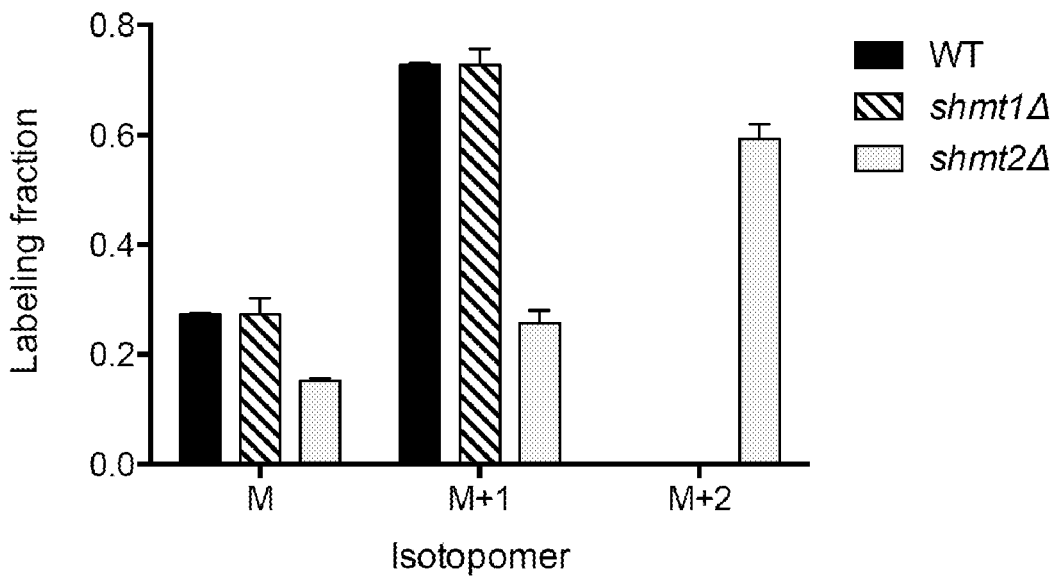
FIGURE 1

Figure 2(a)
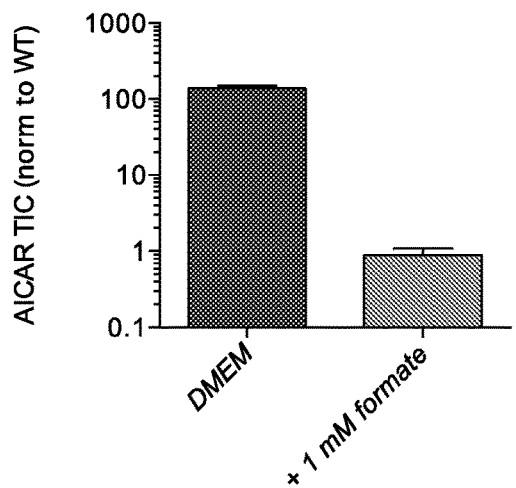
Figure 2(b)
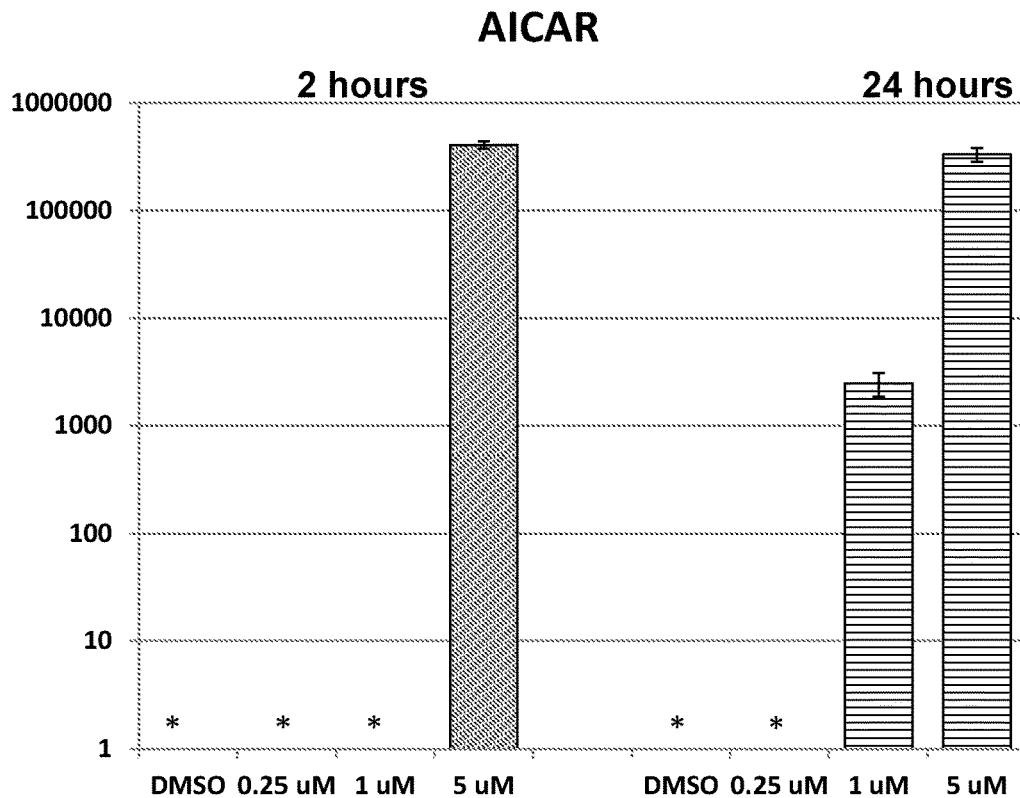
Figure 2(c)

Figure 3(a)
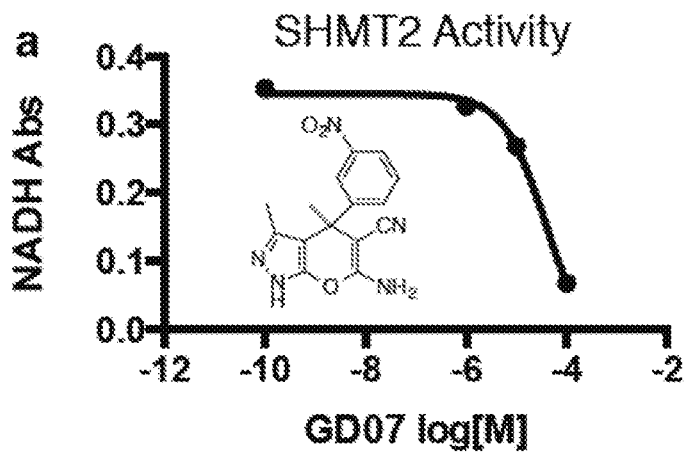
Figure 3(b)
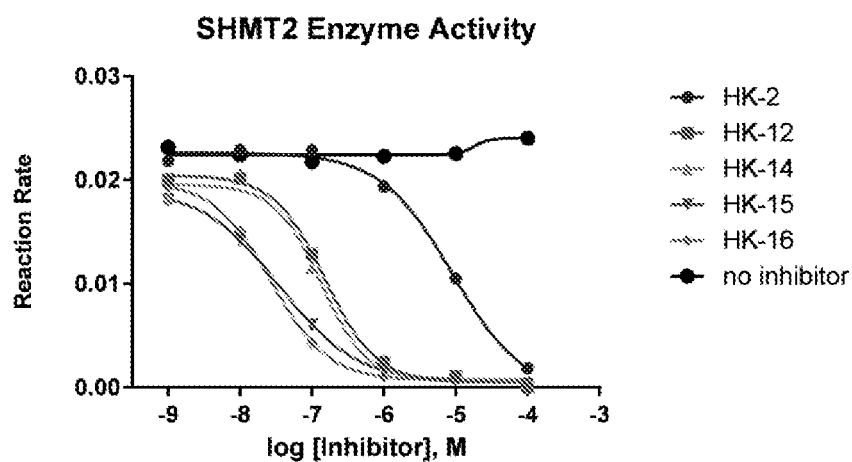
Figure 3(c)
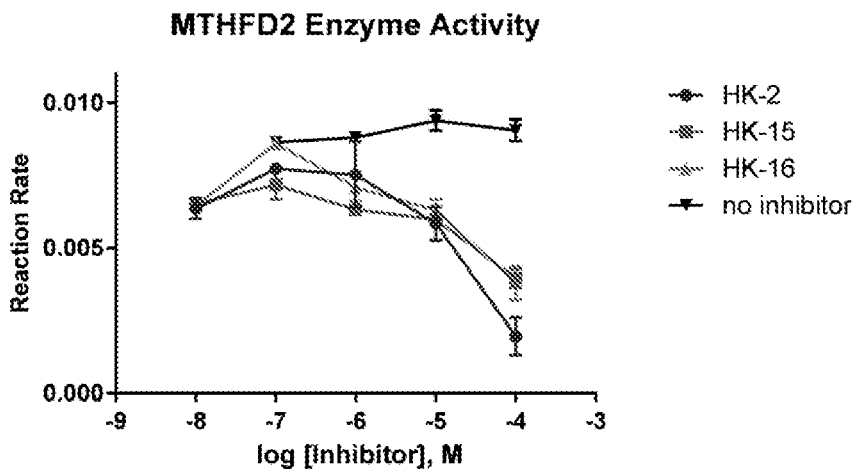
FIGURE 3

Figure 4(a)
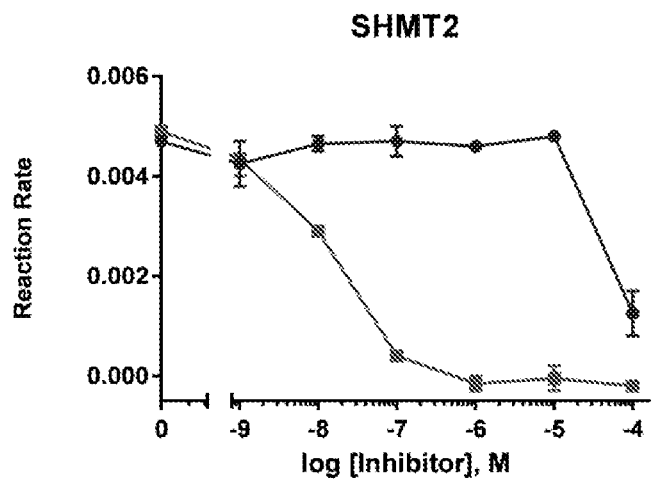
Figure 4(b)
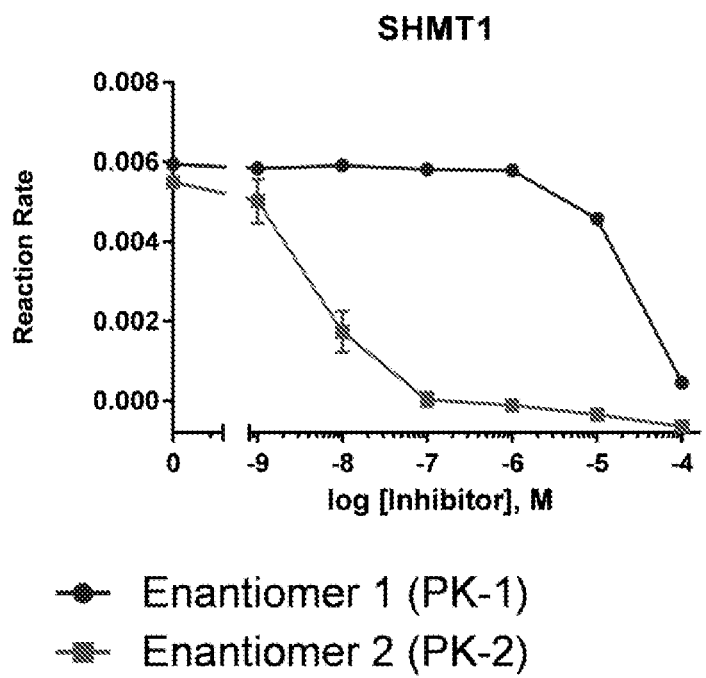
FIGURE 4

Figure 5(a)
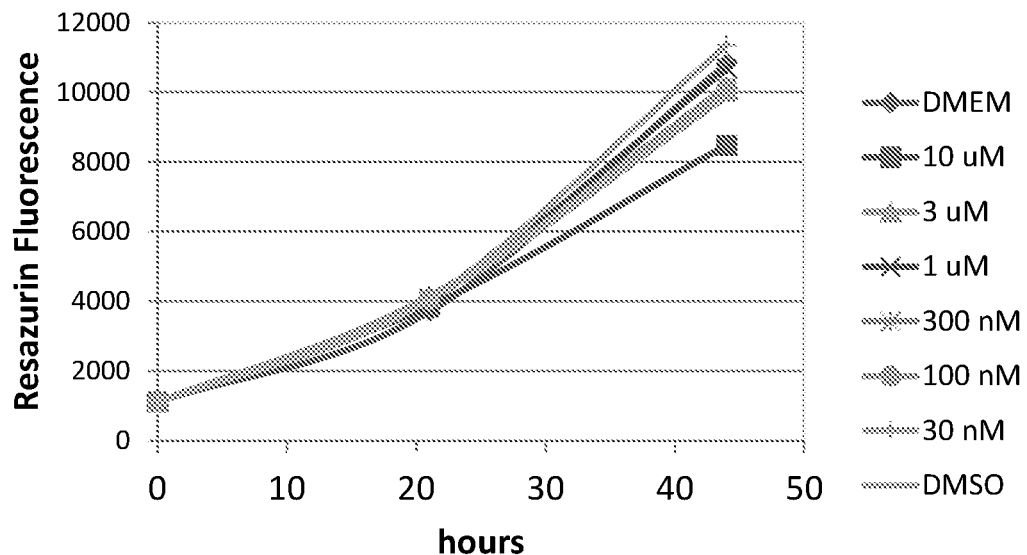
Figure 5(b)
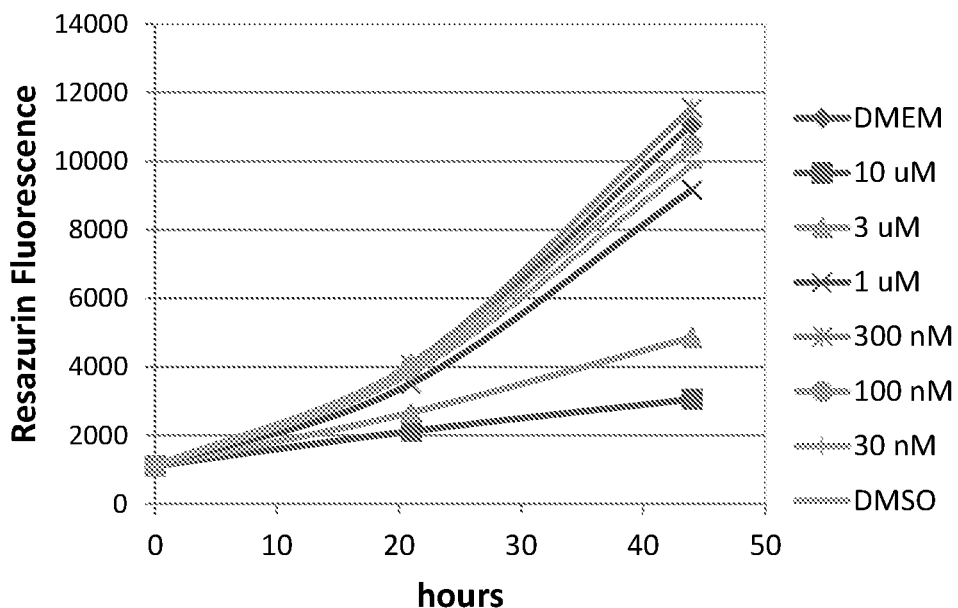
FIGURE 5

Figure 6(a) HK-16-P2
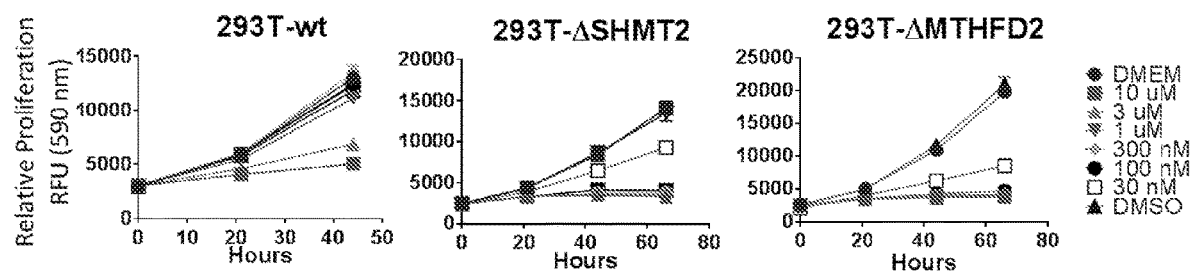
Figure 6(b) HK-16-P1
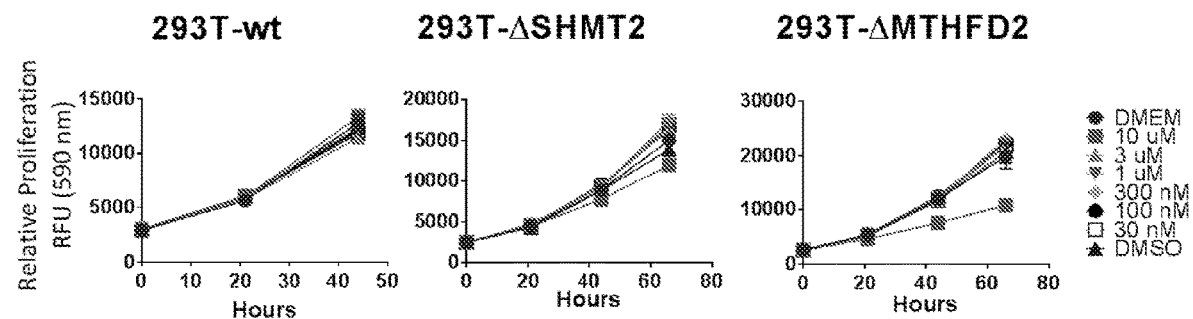

Figure 7(a) HK-16-P2
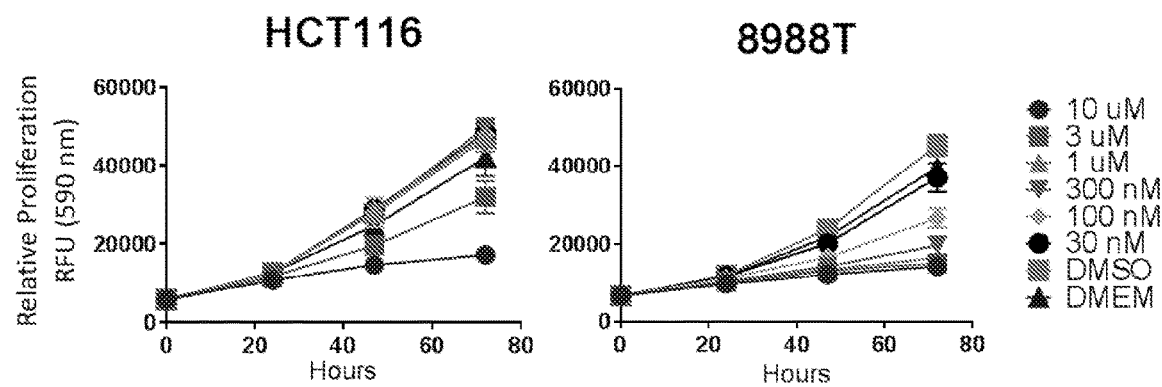
Figure 7(b) HK-16-P1
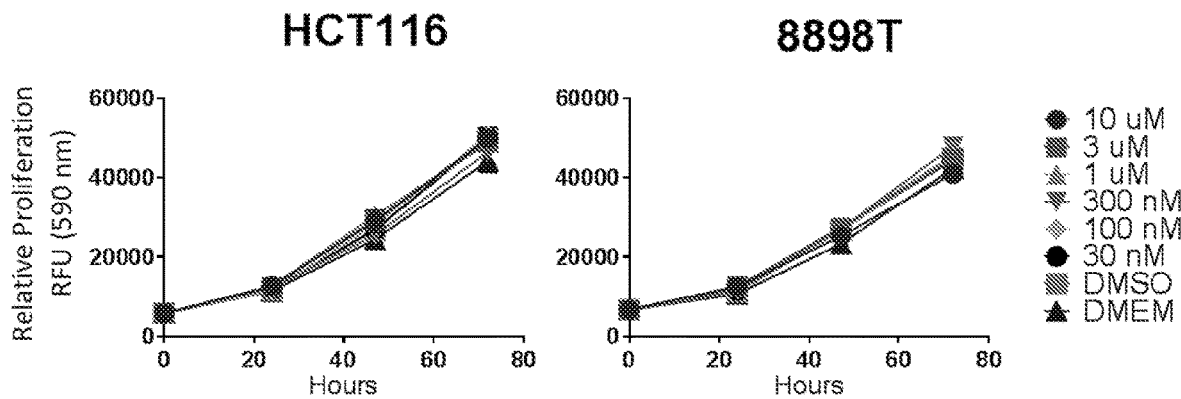

SHMT INHIBITORS

RELATED APPLICATIONS

This application is the U.S. National Stage of International Application No. PCT/US2016/021870, which designated the United States and was filed on Mar. 10, 2016, published in English, which claims priority to U.S. provisional application Ser. No. 62/131,205, filed Mar. 10, 2015. The content of the foregoing applications is incorporated herein by reference in its entirety.

STATEMENT OF GOVERNMENT SUPPORT

This invention was made with government support under Subaward #4769 from Rutgers, the State University of New Jersey, under its Prime Award No. CA163591 awarded by the National Institutes of Health. The government has certain rights in this application.

BACKGROUND OF THE DISCLOSURE

Serine catabolism is initiated by serine hydroxymethyltransferase (SHMT) activity, catalyzed in the cytosol by SHMT1 and in the mitochondria by SHMT2. SHMTs catalyze a reversible reaction converting serine to glycine, with concurrent methylene-tetrahydrofolate (THF) generation. Increased SHMT enzyme activity has been detected in human colon cancer and in rat sarcoma.

SHMT functions to generate one-carbon units for cellular folate metabolism. Inhibition of other aspects of folate metabolism is an established mechanism of therapy for a variety of cancers and autoimmune diseases. However, existing anti-folates are characterized by dose-limiting toxicity that limits their effectiveness in cancer therapy and their tolerability in autoimmune disease.

Hypoxia occurs in the tumor environment, and the mitochondrial form of SHMT, SHMT2, is induced under hypoxic stress. SHMT expression may help tumor cells survive under hypoxic conditions, thus promoting cancerous cell growth, survival and metastasis. Hypoxic cells are generally more resistant to radiation and chemotherapy treatment, further permitting the tumor to grow and metastasize. SHMT2 overexpression has been observed in various different cancers, including neuroblastoma, bladder cancer, colorectal cancer, kidney cancer, etc.

SUMMARY OF THE DISCLOSURE

There is a need in the art for effective treatments for cancer and other conditions, such as autoimmune disease. Without being bound by theory, SHMT enzymes are an attractive target and SHMT inhibitors such as inhibitors of SHMT1 and/or SHMT2, (e.g., selective inhibitors of SHMT2 and/or SHMT1) are suitable for a variety of purposes, such as to inhibit SHMT activity in vitro and/or in vivo. Such inhibitors may act additively or synergistically with other anti-folate compounds, such as to treat cancer and autoimmune disease.

The present disclosure provides compounds, compositions and methods, as described herein. In certain embodiments, the compounds of the disclosure are inhibitors of mammalian SHMT activity, such as mammalian SHMT1 and/or mammalian SHMT2 (e.g., human SHMT1 and/or human SHMT2). Compounds of the disclosure may be provided in isolated or substantially purified form, including as a substantially pure stereoisomer, enantiomer, diastereomer, atropisomer, and/or may be provided as compositions, such as pharmaceutical compositions.

In one aspect, the disclosure provides methods for treating a cancer or autoimmune condition, such as a cancer or autoimmune condition associated with SHMT activity and/or associated with alterations in mitochondrial folate metabolism. In some embodiments, the cancer or autoimmune condition is associated with mitochondrial dysfunction, such as alterations in mitochondrial folate metabolism. In some embodiments, the cancer or autoimmune conditions is characterized by the presence of one or more cells or tissues having mutations in, for example, myc or a protein important for proper mitochondrial function. Exemplary methods include monotherapy, in which a mammalian patient in need thereof is administered an SHMT inhibitor that inhibits activity of a mammalian SMHT2 and/or SHMT1. Further exemplary methods include methods in which an SHMT inhibitor that inhibits activity of a mammalian SHMT2 and/or SHMT1 is administered as part of a therapeutic regime with one or more additional agents or therapeutic modalities.

When multiple agents and/or treatment modalities are used as part of the therapeutic method, each such agent may be administered, independently, at the same or differing times. Similarly, when multiple agents and/or treatment modalities are used as a part of the therapeutic method, each such agent may be administered, independently, using the same or differing routes of administration and/or formulations. All such methods contemplate administration of a compound or a pharmaceutical composition of the disclosure, whether described generally by function as an SHMT inhibitor, or whether described using one or more structural and/or functional features, as set forth herein.

In certain embodiments, the method of treatment (whether as part of a monotherapy or therapeutic regimen) comprises administering to a mammalian subject in need thereof, a compound of Formula (VI) (such as VIa or VIb), as described herein. Similarly contemplated are methods in which a pharmaceutical formulation comprising such a compound is used. Also contemplated are methods comprising administering to a mammalian subject in need thereof a compound of Formula (I) (such as Ia or Ib), (II) (such as IIa or IIb), (III) (such as IIIa or IIIb), (IV) (such as IVa or IVb), or (V) (such as Va or Vb), either as a monotherapy or a combination therapy.

In certain embodiments, the method comprises administration of two or more agents (e.g., an SHMT inhibitor and a second agent or treatment modality). In certain embodiments, the second agent is another anti-cancer therapeutic agent, such as a chemotherapeutic agent, an anti-folate, radiation therapy, or the then standard of care for the particular cancer or autoimmune condition being treated. In certain embodiments, the second agent is a rescue therapy intended to help reduce toxicity or otherwise limit side effects. Such rescue therapy may be used alone with the SHMT inhibitor or together with another anti-cancer agent, such as a traditional anti-folate. Exemplary rescue therapies and other therapeutic modalities are described herein. When multiple agents to treatment modalities are used as part of a therapeutic regimen, they may be administered as the same or differing times. For example, a compound of the disclosure, such as a SHMT inhibitor, may be administered before, at the same time, or following administration of another agent, including a rescue therapy.

In certain embodiments, the cancer is a cancer of a particular tissue, and tumors or cancerous tissue may include cells comprising one or more mutations in, for example, myc or in another gene where the mutation is associated with mitochondrial dysfunction, such as mutations associated with alterations in mitochondrial folate metabolism. It is appreciated that tumors and cancerous tissues are typically heterogenous, such that not all cells in a tumor will have the same mutational status. Rather, one or more cells of the tumor or cancerous tissue contain such a mutation in a mitochondrial enzyme or otherwise associated with alterations in mitochondrial metabolism, such as mitochondrial folate metabolism.

In another aspect, the disclosure provides compounds represented by formula (I), (Ia), or (Ib), or pharmaceutically acceptable salts or stereoisomers thereof, wherein the variables are defined as described herein. In certain embodiments, such compounds are capable of inhibiting SHMT activity, such as SHMT2 and/or SHMT1 activity (e.g., mammalian SHMT1 and/or mammalian SHMT2, such as human SHMT1 and/or human SHMT2). In certain such embodiments, such compounds are selective inhibitors of SHMT2 and/or SHMT1. Of note, inhibitory activity may be evaluated in vitro and/or in vivo.

In one aspect, the disclosure provides compounds represented by general formula (II), (IIa), or (IIb), or pharmaceutically acceptable salts or stereoisomers thereof, wherein the variables are defined as described herein. In certain embodiments, such compounds are capable of inhibiting SHMT activity, such as SHMT2 and/or SHMT1 activity (e.g., mammalian SHMT1 and/or mammalian SHMT2, such as human SHMT1 and/or human SHMT2). In certain such embodiments, such compounds are selective inhibitors of SHMT2 and/or SHMT1. Of note, inhibitory activity may be evaluated in vitro and/or in vivo.

In one aspect, the disclosure provides compounds represented by general formula (III), (IIIa), or (IIIb), or pharmaceutically acceptable salts or stereoisomers thereof, wherein the variables are defined as described herein. In certain embodiments, such compounds are capable of inhibiting SHMT activity, such as SHMT2 and/or SHMT1 activity (e.g., mammalian SHMT1 and/or mammalian SHMT2, such as human SHMT1 and/or human SHMT2). In certain such embodiments, such compounds are selective inhibitors of SHMT2 and/or SHMT1. Of note, inhibitory activity may be evaluated in vitro and/or in vivo In one aspect, the disclosure provides compounds represented by general formula (IV), (Iva), or (IVb), or pharmaceutically acceptable salts or stereoisomers thereof, wherein the variables are defined as described herein. In certain embodiments, such compounds are capable of inhibiting SHMT activity, such as SHMT2 and/or SHMT1 activity (e.g., mammalian SHMT1 and/or mammalian SHMT2, such as human SHMT1 and/or human SHMT2). In certain such embodiments, such compounds are selective inhibitors of SHMT2 and/or SHMT1. Of note, inhibitory activity may be evaluated in vitro and/or in vivo In one aspect, the disclosure provides compounds represented by general formula (V), (Va), or (Vb), or pharmaceutically acceptable salts or stereoisomers thereof, wherein the variables are defined as described herein. In certain embodiments, such compounds are capable of inhibiting SHMT activity, such as SHMT2 and/or SHMT1 activity (e.g., mammalian SHMT1 and/or mammalian SHMT2, such as human SHMT1 and/or human SHMT2). In certain such embodiments, such compounds are selective inhibitors of SHMT2 and/or SHMT1. Of note, inhibitory activity may be evaluated in vitro and/or in vivo In one aspect, the disclosure provides compounds represented by general formula (VI), (VIa), or (VIb), or pharmaceutically acceptable salts or stereoisomers thereof, wherein the variables are defined as described herein. In certain embodiments, such compounds are capable of inhibiting SHMT activity, such as SHMT2 and/or SHMT1 activity (e.g., mammalian SHMT1 and/or mammalian SHMT2, such as human SHMT1 and/or human SHMT2). In certain such embodiments, such compounds are selective inhibitors of SHMT2 and/or SHMT1. Of note, inhibitory activity may be evaluated in vitro and/or in vivo In certain embodiments, compounds of any of formulae (I)-(VI), (Ia)-(VIa), or (Ib)-(VIb) may be described based on any combination of structural and/or functional features provided herein.

In another aspect, the disclosure provides pharmaceutical compositions comprising a compound of the disclosure (e.g., a compound of any of formulae (I)-(VI), (Ia)-(VIa), or (Ib)-(VIb), or a pharmaceutically acceptable salt thereof) formulated with one or more pharmaceutically acceptable carriers and/or excipients.

In another aspect, the disclosure provides compounds of formulae (I)-(VI), (Ia)-(VIa), or (Ib)-(VIb), or pharmaceutically acceptable salts or stereoisomers of any of the foregoing, or pharmaceutical compositions comprising any one of the foregoing, for use as a medicament.

In another aspect, the disclosure provides numerous methods of using compounds of the disclosure alone or in combination with other agents or treatment modalities. Compounds of the disclosure (e.g., a compound of any of formulae (I)-(VI), (Ia)-(VIa), or (Ib)-(VIb)) may be used in any of the in vitro and/or in vivo methods described herein. In certain embodiments, the method is a method of treating cancer. In certain embodiments, the method is a method of treating an autoimmune condition.

In another aspect, the disclosure provides method for treating cancer or an autoimmune disorder. The method comprises administering to a mammalian subject in need thereof an effective amount of an SHMT inhibitor. In certain embodiments, the method comprises administering (either before, at the same time, or after) one or more additional agents, such as a rescue therapy to reduce toxicity.

In certain embodiments, SHMT inhibitor is an inhibitor of SHMT2 and SHMT1. In certain embodiments, the cancer or autoimmune condition is associated with alterations in mitochondrial folate metabolism.

In certain embodiments, the method is a method of treating cancer. In certain embodiments, the cancer comprises a mutation or alteration that affects mitochondrial metabolism, such as a mutation or alteration in a mitochondrial folate pathway gene. By "cancer comprises" it is understood that one or more cells of the tumor or cancerous tissue contain the mutation or alteration. In certain embodiments, the cancer comprises a mutation or alteration in SHMT2, MTHFD2, MTHFD2L, MTHFD1L, fumarate hydratase (FH), SLC25A32, KEAP1, or NRF2, or the patient otherwise has such a mutation or alteration in non-cancerous tissue.

In certain embodiments, the method is for treating an autoimmune disorder. In certain embodiments, the autoimmune disorder is selected from rheumatoid arthritis, dermatomyositis, psoriasis, lupus, sarcoidosis, Crohn's disease, eczema, or vasculitis. In certain embodiments, the subject in need thereof comprises a mutation or alteration that affects mitochondrial metabolism, such as a mutation or alteration in a mitochondrial folate pathway gene. In certain embodiments, the subject in need thereof comprises activation of mitochondrial metabolism.

In certain embodiments, of any of the foregoing or following, the SMHT inhibitor comprises a compound of Formula (VI) or a pharmaceutically acceptable salt thereof:

Formula (VI)

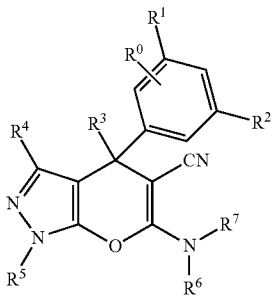

wherein:
$R^0$, $R^1$ and $R^2$ are each independently selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted C$_1$-C$_6$ alkyl, substituted or unsubstituted cycloalkyl, substituted or unsubstituted heterocyclyl, substituted or unsubstituted aryl, substituted or unsubstituted heteroaryl substituted or unsubstituted arylalkyl, substituted or unsubstituted heteroarylalkyl, substituted or unsubstituted C$_1$-C$_6$ haloalkyl, or substituted or unsubstituted C$_1$-C$_6$ haloalkoxy;

$R^3$ is selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted C$_1$-C$_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted C$_1$-C$_6$ haloalkyl, or substituted or unsubstituted C$_1$-C$_6$ haloalkoxy;

$R^4$ is selected from —H, substituted or unsubstituted C$_1$-C$_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

$R^5$, $R^6$ and $R^7$ are each independently selected from —H, —C(O)R$^{11}$, substituted or unsubstituted C$_1$-C$_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl, or $R^5$ is selected from any of the foregoing and $R^6$ and $R^7$ taken together with the nitrogen atom to which they are attached form a substituted or unsubstituted 3-6 membered ring;

each occurrence of $R^{11}$ is independently selected from substituted or unsubstituted C$_1$-C$_6$ alkyl, substituted or unsubstituted cycloalkyl, substituted or unsubstituted heterocyclyl, substituted or unsubstituted aryl, or substituted or unsubstituted heteroaryl; and each occurrence of $R^{10}$ and $R^{12}$ is each independently selected from —H, substituted or unsubstituted C$_1$-C$_6$ alkyl, substituted or unsubstituted cycloalkyl, substituted or unsubstituted heterocyclyl, substituted or unsubstituted aryl, or substituted or unsubstituted heteroaryl.

The disclosure contemplates combinations of any of the aspects and/or embodiments described herein. Compounds of the disclosure may be described based on any suitable combination (e.g., as valence and stability permit) of structural and/or functional properties provided herein. For example, any of the compounds described herein, such as any of the SHMT inhibitors (e.g., compounds that inhibit activity of mammalian SHMT2 and/or SHMT1) described herein, may be used in the treatment of any of the conditions described herein, such as by administering an effective amount to a subject in need thereof. Similarly, any of the compounds described herein may be provided as compositions, such as pharmaceutical compositions, and any such pharmaceutical compositions may be used in the treatment of any of the conditions described herein. Similarly, compounds or compositions of the disclosure may be used in vivo or in vitro, such as in any of the methods, described herein.

DETAILED DESCRIPTION OF THE DRAWINGS

FIG. 1: Deuterated serine (2,2,3-$^2$H serine) isotopic labeling into deoxythymidine phosphates reveals mitochondrial versus cytosolic compartmentalization of serine metabolism. FIG. 1(a) Mitochondrial serine metabolism, utilizing the mitochondrial isoform of serine hydroxymethyl transferase (SHMT2), generates one-carbon units via a formate intermediate resulting in a single deuteron being incorporated into dTMP. Conversely, when serine is metabolized by the cytosolic isoform of serine hydroxymethyl transferase (SHMT1), both deuterons on the carbon atom are retained and incorporated into dTMP. FIG. 1(b) Isotope labeling pattern of deoxythymidine triphosphate (dTTP) in SHMT1 and SHMT2 deletion human cell lines. Wild type (WT) and SHMT1 deletion cells exclusively utilize the mitochondrial pathway to metabolize serine. For each of M, M+1 and M+2, the bars depict, from left to right, data from wild type, SHMT1 deletion cell lines, and SHMT2 deletion cell lines.

FIG. 2: Inhibition of SHMT2 in cells decreases serine metabolism and leads to one-carbon stress. FIG. 2(a) Genetically engineered SHMT2 deletion cell lines show high constitutive levels of 5-aminoimidazole-4-carboxamide ribonucleotide (AICAR), a marker for one-carbon unit stress. This can be rescued by exogenous treatment with sodium formate. FIG. 2(b) Treatment of human cells expressing SHMT2 for 24 hours with HK-16, an inhibitor of SHMT2, results in AICAR accumulation in a dose-dependent manner. (*) indicates AICAR was below the limit of detection. FIG. 2(c) SHMT serine metabolic activity in human cells is inhibited by HK-16, an inhibitor of SHMT2. Uniformly labeled serine is metabolized into various isoptomers in WT cells by the forward and reverse enzymatic activity of SHMT. This process is inhibited in cells by HK-16 in a dose-dependent manner.

FIG. 3: Selective inhibition of human SHMT by racemic pyrazolopyran compounds. FIG. 3(a) Parent pyrazolopyran GD07 shows weak inhibitory activity against recombinant human SHMT2 in an in vitro coupled enzymatic assay as measured at a single time point. FIG. 3(b) Inhibition of enzyme activity (using calculated percent inhibition) by potent pyrazolopyran compounds described in this disclosure against human SHMT2 in an in vitro assay. FIG. 3(c) Pyrazolopyrans that show activity against SHMT2 in vitro do not inhibit human MTHFD2 in enzymatic assays.

FIG. 4: Pyrazolopyran inhibitors are enantiomerically specific. FIG. 4(a) Compound HK-16 was enantiomerically resolved by HPLC into two pure fractions, "Peak 1" and "Peak 2". The anti-SHMT2 activity of HK-16 was confined to the enantiomer represented by "Peak 2" (PK-2). FIG. 4(b) The enantiomer in "Peak 2" is also active against SHMT1 in an in vitro enzyme assay.

FIG. 5: Enantiomerically pure "Peak 2" inhibits human cell growth. FIG. 5(a) Growth of human HEK293T cells in this assay was not appreciably inhibited by enantiomer "Peak 1". FIG. 5(b) Cell growth was inhibited in a dose-dependent manner by the enantiomer ("Peak 2") of the SHMT inhibitor HK-16.

FIG. 6: Cell growth inhibitory effects of varying concentrations of compounds HK-16-P2 and HK-16-P1, versus vehicle, in human embryonic kidney HEK293T cells. FIG. 6(a) shows that Compound HK-16-P2 (Peak 2) is active in wild-type HEK293, SHMT2 knock-out HEK293 cells, and MTHFD2 knock-out HEK293T cells; FIG. 6(b) shows that HK-16-P1 (Peak 1) has significantly less or no effect in wild-type HEK293, SHMT2 knock-out HEK293 cells, and MTHFD2 knock-out HEK293T cells. Cell lines deficient in mitochondrial folate enzymes (generated using CRISPR-Cas9 editing) or otherwise associated with alterations in mitochondrial folate metabolism demonstrate increased sensitivity to inhibition.

FIG. 7. Cell growth inhibitory effects of varying concentrations of compounds HK-16-P1 and HK-16-P2, versus vehicle, in 8988T pancreatic cancer cells and HCT116 human colon carcinoma cells. FIG. 7(a) shows that HK-16-P2 inhibits cancer cell growth. The cancer cells, such as the 8988T pancreatic cancer cells, which harbors a mutation in the downstream mitochondrial folate enzyme MTHFD1L, is significantly more sensitive to HK-16-P2 than cell lines without such a mutation (e.g., with seemingly native expression and/or activity of the mitochondrial folate pathway and/or of mitochondrial metabolism). FIG. 7(b) shows that HK-16-P1 (peak 1) does not inhibit cell growth in HCT116 cell lines. Thus, while the SHMT inhibitor has activity across multiple cancer cell lines, certain cancers appear particularly sensitized (e.g., those associated with alterations in mitochondrial folate metabolism).

Figure 8:
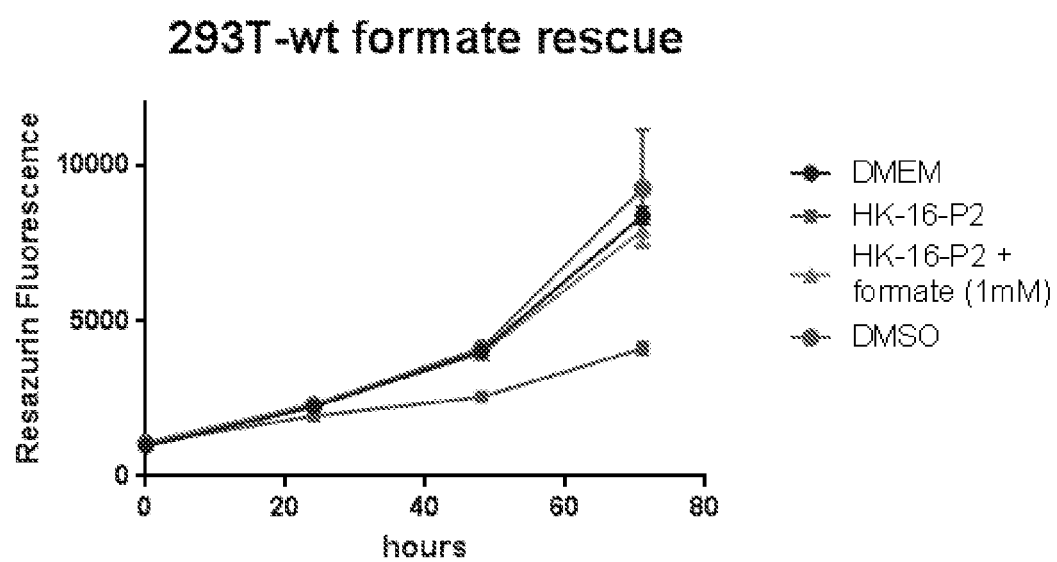

FIG. 8. An example of the rescue effect of formate in cells treated with pyrazolopyran compounds. The inhibitory effects of compound HK-16-P2 (Peak 2) at 10 µM in HEK293T cells were rescued upon co-culturing cells with formate at 1 mM.

DETAILED DESCRIPTION OF THE DISCLOSURE

A. Overview

Serine hydroxymethyltransferase (SHMT) is an enzyme which plays an important role in cellular one-carbon pathways by catalyzing the reversible conversions of L-serine to glycine. In addition, SHMT catalyzes the conversion of tetrahydrofolate to 5,10-methylenetetrahydrofolate (e.g., SHMTs catalyze a reversible reaction converting serine to glycine, with concurrent methylene-tetrahydrofolate (meTHF) generation). SHMT enzymatic activity provides the largest part of the one-carbon units available to the cell. In mammals, such as humans, there are two isoforms of SHMT: SHMT1 in the cytosol and SHMT2 in the mitochondria.

The mammalian enzyme is a tetramer of four identical subunits of approximately 50,000 Daltons each. The intact holoenzyme in vivo has a molecular weight of approximately 200,000 Daltons and incorporates four molecules of vitamin $B_6$ as a coenzyme.

Human beings have an absolute dietary requirement for folic acid, the essential cofactor for one-carbon metabolism, and adequate levels are necessary for both normal embryological development and adult tissue function. It has long been recognized that proliferative tissues are particularly dependent upon one-carbon metabolism, and this led to the development of the first effective chemotherapy, the antifolates. These agents, including methotrexate, and the more recently approved pemetrexed, are routinely used in the treatment of a variety of cancers, including non-small cell lung cancer (NSCLC), osteosarcoma, mesothelioma, breast cancer, and multiple hematological malignancies. However, the utility of these medications is limited by toxicities arising from antifolate activity in normal tissue, which include anemia, neutropenia, diarrhea, and alopecia. These toxicities often necessitate administration of leucovorin as a rescue therapy, although new evidence suggests that folate rescue therapy combined with traditional anti-folates may contribute to drug resistance. These traditional antifolate therapies are believed to function mainly through inhibition of the cytosolic folate enzymes dihydrofolate reductase (DHFR) and thymidylate synthetase (TS), resulting in impaired DNA synthesis and impaired cellular replication. This model is consistent with the toxicity profiles observed in patients who receive antifolate therapies. In contrast, modulation of serine flux and/or folate metabolism via inhibition of SHMT may provide the benefits of traditional antifolate therapies without the deficiencies of an approach based on inhibiting DHFR and/or TS (e.g., traditional anti-folates; alternative anti-folates). Moreover, rescue therapy can still be used, in combination, to help further decrease or manage toxicity. The present disclosure provides methods and compositions suitable for treating cancer and autoimmune conditions, including in subjects having mutations or alterations affecting mitochondrial function or a mitochondrial folate pathway. Without being bound by theory, even in subjects without known alterations in mitochondrial metabolism, SHMT inhibitors are suitable for altering folate metabolism, and thus, depriving cells of the energy necessary to fuel pathological growth and activity. Accordingly, these agents that modulate folate metabolism in the mitochondria and, potentially, in the cytoplasm, have significant utility in modulating cell behavior in numerous contexts including cancer and autoimmune conditions.

Folate metabolism occurs as a cycle between two interconnected pathways: one in the cytosol, which directly contributes one-carbon (1C) units to cellular biosynthetic processes, and one in the mitochondria. The pathways are connected by the metabolites serine, glycine, and formate. Since most studies on folate metabolism initially revolved around the actions of antifolate therapy and the cellular pathophysiology of folate/vitamin B12 deficiency, both of which were believed to involve cytosolic enzymes, the role of the mitochondrial pathway in regulating 1C metabolism was underappreciated until much later. Since its elucidation, however, it has been shown that folate metabolism in the mitochondrial compartment is central to eukaryotic 1C metabolism and is an original source for the majority of 1C units in the tissue systems studied to date. In cancer, mitochondrial serine hydroxymethyl transferase (SHMT2) and the immediate downstream enzyme, mitochondrial methylene tetrahydrofolate dehydrogenase (MTHFD2), which forms the core of the mitochondrial pathway, are highly expressed in multiple cancer types. In contrast, expression of SHMT2 in normal adult tissue was found to be consistently low, even in most rapidly proliferating tissues examined. In a separate study, high SHMT2 expression correlated with lower overall survival in lung cancer patients, and overexpression of this pathway was associated with a poor prognosis in breast cancer.

Without being bound by theory, high expression of core mitochondrial folate enzymes in cancer is consistent with the role of serine flux (which provides these 1C units) through the mitochondria in cancer. A potential outcome of higher serine flux through this compartment is increased export of formate from the mitochondria, effectively augmenting the cytosolic 1C pool. In addition, and without being bound by theory, roles for SHMT2 in cancer may also include a non-biosynthetic role of mitochondrial folate metabolism in cancer as a redox defense through generation of NADPH within the mitochondria (e.g., such as a defense to hypoxic conditions). In addition, and without being bound by theory, the role for SHMT2 in cancer may also include a non-1C metabolism biosynthetic contribution in the form of glycine generation both specifically localized to within the mitochondria and in the cytosol. Glycine synthesis can support mitochondrial health and function as well as the redox state of the entire cell.

Modulation of folate metabolism is suitable for therapeutic intervention, such as in cancer. The present disclosure provides inhibitors of SHMT2 and/or SHMT1. Such inhibitors represent an alternative to traditional anti-folates or anti-folates that directly inhibit DHFR or TS for modulating folate metabolism in cells in vitro and/or in vivo. Thus, in certain embodiments, the disclosure provides compounds, compositions and methods for modulation of serine flux and/or folate metabolism using inhibitors, such as selective inhibitors, of mammalian SHMT enzymes. In certain embodiments, the disclosure provides compounds and methods to modulate (e.g., inhibit) serine flux and/or the mitochondrial folate pathway by inhibiting SHMT2 (e.g., using inhibitors of SHMT2; providing compounds capable of inhibiting SHMT2). Such inhibitors may optionally also inhibit SHMT1. Similarly, in certain embodiments, the disclosure provides compounds and methods to modulate (e.g., inhibit) generation of NADPH by inhibiting SHMT2 (e.g., using inhibitors of SHMT2; providing compounds capable of inhibiting SHMT2). Such inhibitors may optionally also inhibit SHMT1. In certain embodiments, the disclosure provides compounds and methods for modulating (e.g., inhibiting) glycine generation in the mitochondria and/or cytosol in cells. Accordingly, the disclosure provides, in certain embodiments, compounds capable of inhibiting a mammalian SHMT enzyme (e.g., SHMT2 and/or SHMT1), as well as methods for using such compounds. In certain embodiments, such inhibitors of a mammalian SHMT2 and/or SHMT1 are selective inhibitors for SHMT enzymes (e.g., the compounds show selectivity for SHMT enzymes over DHFR and/or TS and/or MTHFD2). In certain embodiments, suitable inhibitors of mammalian SHMT2 and/or SHMT1 do not substantially inhibit the activity of DHFR and/or TS and/or MTHFD2.

These SHMT inhibitors are useful in numerous in vitro and in vivo applications, as described herein, including in the treatment of cancer and other hyperproliferative conditions, as well as in the treatment of autoimmune disorders, particularly those caused or exacerbated by proliferation or increased metabolic activity of immune cells. In certain embodiments, SHMT inhibitors are useful in cancers or other contexts that are associated with alterations in mitochondrial metabolism, such as mitochondrial folate metabolism (e.g., cancers that contain alterations in genes associated with mitochondrial metabolism). Without being bound by theory, such cancers seem to be particularly sensitized to SHMT inhibitors.

B. Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, immunology, and pharmacology, described herein, are those well known and commonly used in the art.

Chemistry terms used herein are used according to conventional usage in the art, for example as exemplified by "The McGraw-Hill Dictionary of Chemical Terms", Parker S., Ed., McGraw-Hill, San Francisco, Calif. (1985).

All of the above, and any other publications, patents and published patent applications referred to in this disclosure are specifically incorporated by reference herein. In case of conflict, the present disclosure, including its specific definitions, will control.

The term "alkoxy" refers to an oxygen atom having an alkyl group attached thereto. Representative alkoxy groups include methoxy, ethoxy, propoxy, tert-butoxy and the like.

The term "alkyl" refers to a saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g., methyl, ethyl, n-propyl, i-propyl, n-butyl and n-pentyl. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone.

Moreover, the term "alkyl" (or "lower alkyl") as used throughout the disclosure, examples, and claims is intended to include both "unsubstituted alkyls" and "substituted alkyls", the latter of which refers to alkyl moieties having substituents replacing a hydrogen on one or more carbons of the hydrocarbon backbone.

Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety.

The term "arylkyl", as used herein, refers to an alkyl group substituted with one or more aryl groups.

The term "aryl", as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, and the like.

The terms "nitrile" or "cyano," as used herein, refers to —CN.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl. The terms "halo" and "halogen", as used herein, means halogen and includes chloro, fluoro, bromo, and iodo.

The term "haloalkyl", as used herein, means an alkyl group substituted with one or more halogens. When more than one halogen is present, the halogens may be the same or different. For examples, haloalkyl groups include, but are not limited to, fluoromethyl, difluoromethyl, trifluoromethyl, chlorodifluoromethyl, 2,2,2-trifluoroethyl, pentafluoroethyl, and the like.

The term "haloalkoxy", as used herein, means an alkoxy group substituted with one or more halogens. When more than one halogen is present, the halogens may be the same or different. For examples, haloalkyl groups include, but are not limited to, difluoromethoxy, trifluoromethoxy, 2,2,2-trifluoroethoxy, pentafluoroethoxy, and the like.

The term "heteroarylakyl", as used herein, refers to an alkyl group substituted with a heteroaryl group.

The term "heteroaryl" includes substituted or unsubstituted aromatic single ring structures, preferably 5- to 7-membered rings, more preferably 5- to 6-membered rings, whose ring structures include at least one heteroatom (e.g., O, N, or S), preferably one to four, or one to 3 heteroatoms, more preferably one or two heteroatoms. When two or more heteroatoms are present in a heteroaryl ring, they may be the same or different. For examples, heteroaryl groups include, but are not limited to, pyrrole, furan, thiophene, imidazole, tetrazole, oxazole, thiazole, pyrazole, pyridine, pyrazine, pyridazine, pyrimidine, and the like.

The term "heteroatom", as used herein, means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. In certain embodiments, the ring structure can have two cyclic rings. In some embodiments, the two cyclic rings can have two or more atoms in common, e.g., the rings are "fused rings." Heterocyclyl groups include, for example, piperidine, piperazine, pyrrolidine, morpholine, lactones, lactams, and the like.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

Unless specifically stated as "unsubstituted," references to chemical moieties herein are understood to include substituted variants. For example, reference to an "alkyl" group or moiety implicitly includes both substituted and unsubstituted variants.

The term "ring" or "ring system", unless context indicates otherwise, may include monocyclic rings or polycyclic rings, such as bicyclic rings. When the term ring refers to a polycyclic or bicyclic ring, each ring is independently selected from saturated or unsaturated, and either or both rings may contain one or more heteroatoms, preferably a total of 0, 1, 2, 3 or 4 heteroatoms across the ring system.

At various places in the present specification substituents of compounds of the disclosure are disclosed in groups or in ranges. It is specifically intended that the disclosure include each and every individual subcombination of the members of such groups and ranges. For example, the term "$C_1$-$C_6$ alkyl" is specifically intended to individually disclose methyl, ethyl, propyl, isopropyl, n-butyl, sec-butyl, isobutyl, etc.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats). In certain embodiments, the patient or subject is a human patient or subject, such as a human patient having a condition associated with SHMT activity and in need of treatment. In certain embodiments, the patient or subject is a mammal or a mammal other than a human.

"SHMT" refers to serine hydroxymethyltransferase. Such enzymes are known and, in mammals, both SHMT1 and SHMT2 are expressed and active. Exemplary SHMTs include mammalian SHMT1 and SHMT2, such as human SHMT1 and SHMT2. Further structural information regarding human SHMT1 can be found at NCBI entrez ID number 6470. Further structural information regarding human SHMT2 can be found at NCBI entrez ID number 6472.

"Inhibitor" as used herein refers to any molecule that is capable of interacting directly or indirectly with another molecule (e.g., an enzyme or receptor) and causing a decrease in a biological activity of that other molecule. In certain embodiments, the compounds of the present disclosure inhibit mammalian SHMT enzyme activity (e.g., SHMT1 and/or SHMT2). In certain embodiments the inhibitors are selective inhibitors of SHMT enzyme activity (e.g., SHMT1 and/or SHMT2). In certain embodiments, the inhibitors bind to SHMT1 and/or SHMT2 (e.g., bind to the enzyme). In certain embodiments, the SHMT inhibitor is an inhibitor of SHMT2 and does not inhibit or inhibits with a significantly lower $IC_{50}$ an activity of SHMT1. In certain embodiments, the SHMT inhibitor inhibits an activity of SHMT2 and, optionally, SHMT1. In certain embodiments, the SHMT inhibitor inhibits both SHMT1 and SHMT2 (e.g., either with approximately the same $IC_{50}$ or within 2, 3 or 4-fold). In certain embodiments, the compounds of the disclosure (such as compounds of formula (I) (including compounds of formulae (Ia) and formula (Ib)), formula (II) (including compounds of formulae (IIa) and (IIb)), formula (III) (including compounds of formulae (IIIa) and (IIIb)), formula (IV) (including compounds of formulae (Iva) and (IVb)), formula (V) (including compounds of formulae (Va) and (Vb)), or (VI) (including compounds of formula (VIa) and formula (VIb)), and pharmaceutically acceptable salts thereof, as well as the individual compounds disclosed herein) are used as inhibitors of SHMT activity (e.g., enzyme activity). In certain embodiments, compounds of the disclosure are SHMT inhibitors, such as selective SHMT inhibitors (SHMT1 and/or SHMT2). It should be noted that a compound may be characterized as an SHMT1 and/or SHMT2 inhibitor by evaluation in an in vitro assay. This gives an accurate characterization. However, in vivo, the compound's mechanism of action may be primarily via its effect on one but not both enzymes. For example, when used in a subject or cell line deficient in SHMT2, the compound's effect on cell proliferation may be primarily through its effect as an SHMT1 inhibitor. Similarly, in some systems, a compound may have poor penetration or accessibility to the mitochondria, and thus, the effect of the compound may be primarily through its effect on SHMT1—despite its high intrinsic activity against SHMT2. Regardless of the particular mechanism of action at play in any particular in vivo system, inhibitors may be characterized as SHMT2 and/or SHMT1 inhibitors based on activity in one or more in vitro assays, as described herein.

In certain embodiments, by "SHMT activity" is meant a native function of a mammalian SHMT enzyme, such its native enzymatic activity. In certain embodiments, SHMT activity refers to the function of mammalian SHMT to catalyze a reversible reaction converting serine to glycine. In certain embodiments, SHMT activity refers to the function of mammalian SHMT to catalyze a reversible reaction converting serine to glycine with concurrent methylene-tetrahydrofolate (meTHF) generation. In certain embodiments, SHMT activity refers to the generation of 1C units. SHMT activity may be assayed or evaluated in numerous ways, such as is described herein. SHMT activity may be evaluated by evaluating serine flux and/or folate metabolism, such as mitochondrial serine flux, glycine synthesis, NADPH generation, generation and excretion of formate or mitochondrial folate metabolism.

The term "compounds of the disclosure" refers to any of the compounds described herein based on any combination of structural and/or functional features, including compounds of formula (I) (including compounds of formulae (Ia) and formula (Ib)), formulae (II) (including compounds of formulae (IIa) and (IIb)), formulae (III) (including compounds of formulae (IIIa) and (IIIb)), formula IV (including compounds of formulae (Iva) and (IVb)), formula (V) (including compounds of formulae (Va) and (Vb)), or formula (VI) (including compounds of formulae (VIa) and (VIb)), wherein the variables are defined as provided herein, as well as to any of the specific compounds described herein. The term "compounds of the disclosure" refers, unless context indicates otherwise, to salts of such compounds, such as pharmaceutically acceptable salts. In certain embodiments, compounds of the disclosure are capable of inhibiting SHMT activity, such as enzyme activity. In certain embodiments, compounds of the disclosure are inhibitors of SHMT2 and, optionally, SHMT1. In certain embodiments, compounds of the disclosure are selective inhibitors of SHMT (e.g., SHMT1 and/or 2). In certain embodiments, compounds of the disclosure are selective for SHMT over MTHFD2 and/or DHFR and/or TS. For example, in certain embodiments, compounds of the disclosure either do not inhibit or inhibit one or more of MTHFD2, DHFR, FH, TS and/or another protein involved in mitochondrial folate metabolism with an IC50 at least 25 fold, at least 50 fold, at least 75 fold, at least 100 fold, at least 200 fold, at least 500 fold, at least 1000 fold, or greater than 1000 fold less than that for SHMT2 and/or SHMT1.

In certain embodiments, compounds of the disclosure include compounds provided as a pharmaceutical composition.

Compounds of the disclosure also include tautomeric forms, such as keto-enol tautomers, prototropic tautomers, and the like, for example annular tautomers wherein a proton can occupy two or more positions on a heteroaryl system. Tautomeric forms can be in equilibrium or sterically locked into one form by appropriate substitution. It is understood that the various tautomeric forms are within the scope of the compounds of the present disclosure.

Compounds of the disclosure also include all isotopes of atoms occurring in the intermediates and/or final compounds. Isotopes include those atoms having the same atomic number but different mass numbers. For example, isotopes of hydrogen include deuterium and tritium.

Compounds of formula I (including compounds of formula Ia and formula Ib) and II, III, IV, V, or VI (and the other compounds of the disclosure) have one or more chiral centers and therefore can exist as enantiomers and/or diastereomers. Compounds of formula (I) (including compounds of formula (Ia) and formula (Ib)) and (II), (III), (IV), (V), or (VI) (and the other compounds of the disclosure) may also exist as stereoisomers, for example atropisomers, resulting from hindered rotation about a single bond. The compound of the disclosure are understood to extend to, and embrace all such enantiomers, diastereomers, atropisomers, stereoisomers, and mixtures thereof, including but not limited to racemates. Formula (I) (including compounds of formula (Ia) and formula (Ib) and (II), (III), (IV), (V), or (VI) (and the other compounds of the disclosure) used throughout this disclosure are intended to represent all individual stereoisomers and mixtures thereof, unless stated or shown otherwise.

"Treating" a condition or patient refers to taking steps to obtain beneficial or desired results, including clinical results. Beneficial or desired clinical results include, but are not limited to, alleviation, amelioration, or slowing the progression, of one or more symptoms associated with a condition, such as cancer. Exemplary beneficial clinical results are described herein.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent.

Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. When a method is part of a therapeutic regimen involving more than one agent or treatment modality, the disclosure contemplates that the agents may be administered at the same or differing times and via the same or differing routes of administration.

Appropriate methods of administering a substance, a compound or an agent to a subject will also depend, for example, on the age of the subject, whether the subject is active or inactive at the time of administering, whether the subject is cognitively impaired at the time of administering, the extent of the impairment, and the chemical and biological properties of the compound or agent (e.g. solubility, digestibility, bioavailability, stability and toxicity).

A "therapeutically effective amount" or a "therapeutically effective dose" of a drug or agent is an amount of a drug or an agent that, when administered to a subject will have the intended therapeutic effect, sufficient to show a meaningful patient benefit, e.g., treatment, healing, inhibition or amelioration of a physiological response or condition, etc. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of disease, the therapeutics or combination of therapeutics selected for administration, and the mode of administration. The skilled worker can readily determine the effective amount for a given situation by routine experimentation.

The term "pharmaceutical composition" refers to a composition suitable for pharmaceutical use in a subject animal, including humans and mammals, e.g., combined with one or more pharmaceutically acceptable carriers, excipients or solvents. Such a composition may also contain diluents, fillers, salts, buffers, stabilizers, solubilizers, and other materials well known in the art. In certain embodiments, a pharmaceutical composition encompasses a composition comprising the active ingredient(s), and the inert ingredient(s) that make up the excipient, carrier or diluent, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and one or more pharmaceutically acceptable excipient(s), carrier(s) and/or diluent(s).

Accordingly, the pharmaceutical compositions of the present disclosure encompass any composition made by admixing a compound of the disclosure and one or more pharmaceutically acceptable excipient(s), carrier(s) and/or diluent(s).

In certain embodiments, a "pharmaceutically acceptable" substance is suitable for use in contact with cells, tissues or organs of animals or humans without excessive toxicity, irritation, allergic response, immunogenicity or other adverse reactions, in the amount used in the dosage form according to the dosing schedule, and commensurate with a reasonable benefit/risk ratio. In certain embodiments, a "pharmaceutically acceptable" substance that is a component of a pharmaceutical composition is, in addition, compatible with the other ingredient(s) of the composition.

The terms "pharmaceutically acceptable excipient", "pharmaceutically acceptable carrier" and "pharmaceutically acceptable diluent" encompass, without limitation, pharmaceutically acceptable inactive ingredients, materials, compositions and vehicles, such as liquid fillers, solid fillers, diluents, excipients, carriers, solvents and encapsulating materials. Carriers, diluents and excipients also include all pharmaceutically acceptable dispersion media, coatings, buffers, isotonic agents, stabilizers, absorption delaying agents, antimicrobial agents, antibacterial agents, antifungal agents, adjuvants, and so on. Except insofar as any conventional excipient, carrier or diluent is incompatible with the active ingredient, the present disclosure encompasses the use of conventional excipients, carriers and diluents in pharmaceutical compositions. See, e.g., Remington: The Science and Practice of Pharmacy, 21st Ed., Lippincott Williams & Wilkins (Philadelphia, Pa., 2005); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Preformulation and Formulation, Gibson, Ed., CRC Press LLC (Boca Raton, Fla., 2004). A "pharmaceutically acceptable salt" is a salt of a compound that is suitable for pharmaceutical use, including but not limited to metal salts (e.g., sodium, potassium, magnesium, calcium, etc.), acid addition salts (e.g., mineral acids, carboxylic acids, etc.), and base addition salts (e.g., ammonia, organic amines, etc.).

"Pharmaceutically acceptable salt" or "salt" is used herein to refer to an agent or a compound according to the disclosure that is a therapeutically active, non-toxic base and acid salt form of the compounds. The acid addition salt form of a compound that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclic, salicylic, p-aminosalicylic, pamoic and the like. See, e.g., WO 01/062726. Some pharmaceutically acceptable salts listed by Berge et al., *Journal of Pharmaceutical Sciences*, 66: 1-19 (1977), incorporated herein by reference in its entirety.

Compounds containing acidic protons may be converted into their therapeutically active, non-toxic base addition salt form, e.g. metal or amine salts, by treatment with appropriate organic and inorganic bases. Appropriate base salt forms include, for example, ammonium salts, alkali and earth alkaline metal salts, e.g., lithium, sodium, potassium, magnesium, calcium salts and the like, salts with organic bases, e.g. N-methyl-D-glucamine, hydrabamine salts, and salts with amino acids such as, for example, arginine, lysine and the like. Conversely, said salt forms can be converted into the free forms by treatment with an appropriate base or acid. Compounds and their salts can be in the form of a solvate, which is included within the scope of the present disclosure. Such solvates include for example hydrates, alcoholates and the like. See, e.g., WO 01/062726.

The disclosure further provides pharmaceutical compositions comprising one or more compounds of the disclosure together with a pharmaceutically acceptable carrier or excipient. Compounds or pharmaceutical compositions of the disclosure may be used in vitro or in vivo. Exemplary compounds of the disclosure, including examples of SHMT inhibitors, are provided herein. SHMT inhibitors may include any such compounds, as well as other compounds described structurally and/or functionally.

C. Compounds

In one aspect, the disclosure provides compounds represented by general formula I:

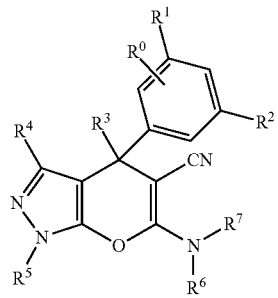

Formula (I)

wherein:
$R^0$, $R^1$ and $R^2$ are each independently selected from —H, halogen, hydroxyl, nitro, nitrile, —$SOR^{11}$, —$S(O)_2R^{11}$, —$S(O)_2NR^{10}R^{12}$, —$OR^{11}$, —$OC(O)R^{12}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;
$R^3$ is selected from —H, halogen, hydroxyl, nitro, nitrile, —$SOR^{11}$, —$S(O)_2R^{11}$, —$S(O)_2NR^{10}R^{12}$, —$OR^{11}$, —$OC(O)R^{12}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;
$R^4$ is selected from H, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;
$R^5$, $R^6$ and $R^7$ are each independently selected from —H, —$C(O)R^{11}$, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl, or $R^5$ is selected from any of the foregoing and $R^6$ and $R^7$ taken together with the nitrogen atom to which they are attached form a substituted or unsubstituted 3-6 membered ring; with the proviso that the occurrences of $R^5$, $R^6$ and $R^7$ are not all H simultaneously; each occurrence of $R^{11}$ is independently selected from substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl; and each occurrence of $R^{10}$ and $R^{12}$ is each independently selected from —H, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl, or a pharmaceutically acceptable salt thereof.

In certain embodiments, the compounds of the disclosure, or a pharmaceutically acceptable salt thereof, are represented by Formula (Ia) (wherein the R groups are as described above for Formula (I):

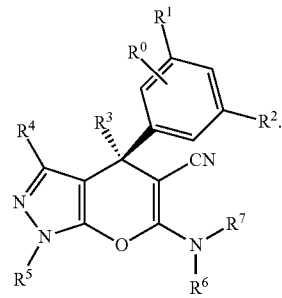

Formula (Ia)

In certain embodiments, the compounds of the disclosure, or a pharmaceutically acceptable salt thereof, are represented by Formula (Ib) (wherein the R groups are as described above for Formula (I)):

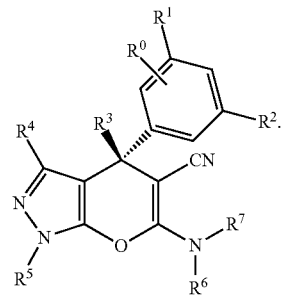

Formula (Ib)

In certain embodiments, any of the compounds of Formula (I) (including of Formula Ia or Ib) described herein, or a pharmaceutically acceptable salt thereof, are capable of inhibiting activity of an SHMT enzyme (e.g., are SHMT inhibitors, such as an SHMT2 inhibitor). Any such compounds described based on any of the structural features described herein may, in certain embodiments, also be described based on any of the functional features described herein (e.g., binding affinity for SHMT1 and/or 2, IC50, selectivity, inhibitory effect on serine flux or mitochondrial serine flux, etc.)

In certain embodiments of any of the foregoing or following, a compound of the disclosure is provided in isolated or substantially purified form, such as a substantially purified stereoisomer of a compound of the disclosure. Without being bound by theory, compounds of the disclosure have a stereocenter. Thus, in certain embodiments, substantially purified stereoisomers are provided and are suitable in any of the methods described herein.

In certain embodiments, the disclosure provides a pharmaceutically acceptable salt of any of the compounds of the disclosure.

In certain embodiments of any of the foregoing or following, $R^0$, $R^1$ and $R^2$ are each independently selected from —H, halogen, hydroxyl, nitro, nitrile, —$SOR^{11}$, —$S(O)_2R^{11}$, —$S(O)_2NR^{10}R^{12}$, —$OR^{11}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy.

In certain embodiments of any of the foregoing or following, $R^0$ is selected from hydroxyl, —$S(O)_2R^{11}$, —$S(O)_2NR^{10}R^{12}$, —$OR^{11}$, —$C(O)NR^{10}R^{12}$, —$NR^{10}R^{12}$, —$N(R^{12})C(O)R^{11}$, or —$NS(O)_2R^{12}$. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ (and, optionally $R^0$) are each independently selected from —H, halogen, hydroxyl, nitro, nitrile, —$OR^{11}$, substituted or unsubstituted $C_1$-$C_6$ alkyl, substituted or unsubstituted $C_1$-$C_6$ haloalkyl, or substituted or unsubstituted $C_1$-$C_6$ haloalkoxy. In other embodiments, $R^1$ and $R^2$ (and, optionally $R^0$) are each independently selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl.

In certain embodiments of any of the foregoing or following, $R^1$ and $R^2$ (and, optionally $R^0$) are each independently selected from —H, methoxy, fluoro, chloro, bromo, hydroxyl, nitro, nitrile, methyl, trifluoromethyl, or trifluoromethoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ (and, optionally $R^0$) are each independently selected from —H, methoxy, chloro, nitro, nitrile, or trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ (and, optionally, $R^0$) are each trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^3$ is selected from —H, halogen, hydroxyl, nitro, nitrile, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected from substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected from substituted or unsubstituted $C_1$-$C_6$ alkyl, or substituted or unsubstituted cycloalkyl.

In certain embodiments of any of the foregoing or following, $R^3$ is selected from methyl, ethyl, propyl, isopropyl, cyclopropyl, or cyclobutyl. In certain embodiments, any of the foregoing may be optionally substituted.

In certain embodiments of any of the foregoing or following, $R^3$ is selected from isopropyl, cyclopropyl, or cyclobutyl. In certain embodiments, any of the foregoing may be optionally substituted.

In certain embodiments of any of the foregoing or following, $R^3$ is cyclobutyl. In certain embodiments, acyclobutyl may be optionally substituted.

In certain embodiments of any of the foregoing or following, $R^4$ is selected from —H, substituted or unsubstituted $C_1$-$C_6$ alkyl, substituted or unsubstituted cycloalkyl, substituted or unsubstituted aryl, substituted or unsubstituted heteroaryl, or substituted or unsubstituted arylalkyl.

In certain embodiments of any of the foregoing or following, $R^4$ is selected from —H, substituted or unsubstituted $C_1$-$C_6$ alkyl, substituted or unsubstituted cycloalkyl, substituted or unsubstituted aryl, or substituted or unsubstituted arylalkyl.

In certain embodiments of any of the foregoing or following, $R^4$ is selected from methyl, ethyl, isopropyl, cyclopropyl, cyclobutyl, cyclopentyl, cyclohexyl, phenyl or benzyl. In certain embodiments, any of the foregoing may be optionally substituted.

In certain embodiments of any of the foregoing or following, $R^4$ is methyl or isopropyl. In certain embodiments, any of the foregoing may be optionally substituted.

In certain embodiments of any of the foregoing or following, $R^4$ is methyl. In certain embodiments, methyl may be optionally substituted.

In certain embodiments of any of the foregoing or following, $R^5$, $R^6$ and $R^7$ are each independently selected from —H, —$C(O)R^{11}$, substituted or unsubstituted $C_1$-$C_6$ alkyl, substituted or unsubstituted cycloalkyl, substituted or unsubstituted aryl, substituted or unsubstituted arylalkyl, or $R^5$ is selected from any of the foregoing and $R^6$ and $R^7$ taken together with the nitrogen atom to which they are attached form a substituted or unsubstituted 3-6 membered ring.

In certain embodiments of any of the foregoing or following, $R^5$, $R^6$ and $R^7$ are each independently selected from —H, —$C(O)R^{11}$, substituted or unsubstituted $C_1$-$C_6$ alkyl, substituted or unsubstituted cycloalkyl, substituted or unsubstituted aryl, or substituted or unsubstituted arylalkyl.

In certain embodiments of any of the foregoing or following, $R^5$, $R^6$ and $R^7$ are each independently selected from —H, methyl, ethyl, isopropyl, cyclopropyl, cyclobutyl, cyclopentyl, cyclohexyl, phenyl, benzyl, or —$COCH_3$. In certain embodiments, any of the foregoing, except —H, may be optionally substituted.

In certain embodiments of any of the foregoing or following, $R^5$, $R^6$ and $R^7$ are each independently selected from —H, methyl, phenyl, or —$COCH_3$. In certain embodiments, any of the foregoing, except —H, may be optionally substituted.

In certain embodiments of any of the foregoing or following, $R^5$ and $R^6$ are each independently selected from —H, methyl or phenyl. In certain embodiments, any of the foregoing, except —H, may be optionally substituted.

In certain embodiments of any of the foregoing or following, $R^7$ is —H.

In certain embodiments of any of the foregoing or following, $R^6$ and $R^7$ taken together with the nitrogen atom to which they are attached form a substituted or unsubstituted 3-6 membered ring. In certain embodiments the 3-6 membered ring is a monocylic ring. In certain embodiments, the 3-6 membered ring may be saturated or unsaturated (e.g., contain at least one double bond). In certain embodiments, the 3-6 membered ring may contain one or two additional heteroatoms, other than the nitrogen atom to which $R^6$ and $R^7$ are attached.

In certain embodiments of any of the foregoing or following, $R^5$ is selected from —H, methyl, ethyl, isopropyl, cyclopropyl, cyclobutyl, cyclopentyl, cyclohexyl, phenyl, benzyl, or —COCH$_3$, and $R^6$ and $R^7$ taken together with the nitrogen atom to which they are attached form a substituted or unsubstituted ring selected from:

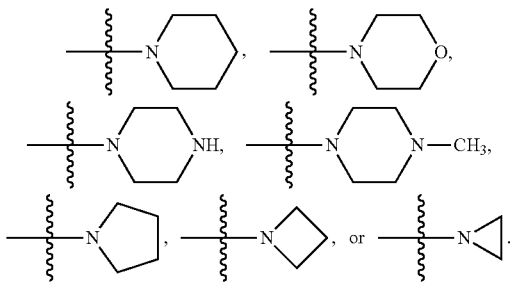

In certain embodiments of any of the foregoing or following, $R^5$ is selected from —H, methyl, phenyl, or —COCH$_3$, and $R^6$ and $R^7$ taken together with the nitrogen atom to which they are attached form a substituted or unsubstituted ring selected from:

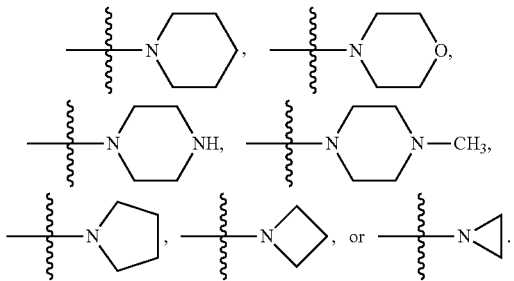

In certain embodiments of any of the foregoing or following, each occurrence of $R^{11}$ is independently selected from substituted or unsubstituted $C_1$-$C_6$ alkyl or substituted or unsubstituted cycloalkyl. In certain embodiments, there is no occurrence of $R^{11}$.

In certain embodiments of any of the foregoing or following, each occurrence of $R^{10}$ and $R^{12}$ is each independently selected from —H, substituted or unsubstituted $C_1$-$C_6$ alkyl, or substituted or unsubstituted cycloalkyl, such as from —H, or substituted or unsubstituted $C_1$-$C_6$ alkyl. In certain embodiments, each occurrence of $R^{10}$ and $R^{12}$ is —H. In certain embodiments, there is no occurrence of $R^{10}$ and/or $R^{12}$.

In certain embodiments of any of the foregoing or following, $R^0$ is selected from —H, halogen, hydroxyl, nitro, nitrile, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;

$R^1$ and $R^2$ are each independently selected from —H, methoxy, fluoro, chloro, bromo, hydroxyl, nitro, nitrile, methyl, or trifluoromethyl;

$R^3$ is selected from methyl, ethyl, propyl, isopropyl, cyclopropyl, or cyclobutyl;

$R^4$ is selected from methyl, ethyl, isopropyl, cyclopropyl, cyclobutyl, cyclopentyl, cyclohexyl, phenyl or benzyl; and $R^5$, $R^6$ and $R^7$ are each independently selected from —H, methyl, ethyl, isopropyl, cyclopropyl, cyclobutyl, cyclopentyl, cyclohexyl, phenyl, benzyl, or —COCH$_3$.

In certain embodiments of any of the foregoing or following, $R^0$ is selected from —H, hydroxyl, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, or —NS(O)$_2$R$^{12}$;

$R^1$ and $R^2$ are each independently selected from —H, methoxy, chloro, nitro, nitrile, or trifluoromethyl;

$R^3$ is selected from isopropyl, cyclopropyl, or cyclobutyl;

$R^4$ is methyl or isopropyl; and $R^5$, $R^6$ and $R^7$ are each independently selected from —H, methyl, phenyl, or —COCH$_3$.

In certain embodiments of any of the foregoing or following, $R^0$ is selected from —H, hydroxyl, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, or —NS(O)$_2$R$^{12}$;

$R^1$ and $R^2$ are each —CF$_3$;

$R^3$ is cyclobutyl;

$R^4$ is methyl;

$R^5$ and $R^6$ are each independently selected from H, methyl or phenyl; and $R^7$ is H.

In certain embodiments, the compound is selected from:

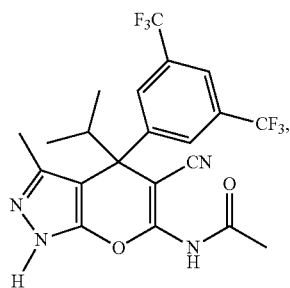

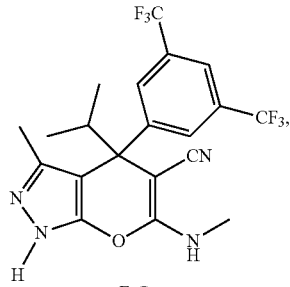

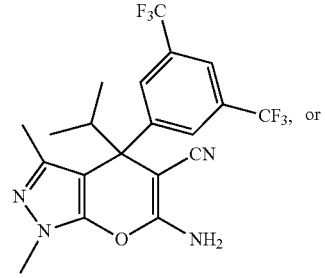

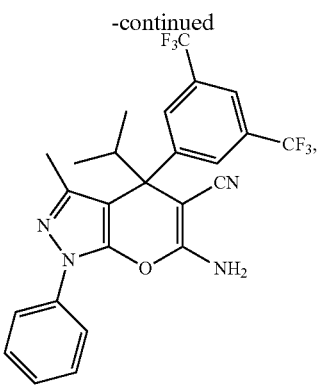

or a pharmaceutically acceptable salt thereof.

In certain embodiments of any of the foregoing or following, the disclosure provides a pharmaceutically acceptable salt thereof or an enantiomer thereof.

In certain embodiments of any of the foregoing or following, the $R^0$, $R^1$ and $R^2$ are not all simultaneously —H. In other embodiments, $R^0$ is —H and the ring to which it is attached, is substituted with a single substituent (other than —H) at one of $R^1$ or $R^2$. In certain embodiments, $R^0$ is —H, and $R^1$ and $R^2$ are not —H. In other embodiments, $R^1$ is —H and the ring to which it is attached is substituted with a single substituent (other than —H) at one of $R^0$ or $R^2$. In certain embodiments, $R^1$ is —H, and $R^0$ and $R^2$ are not —H. In other embodiments, $R^2$ is —H and the ring to which it is attached is substituted with a single substituent (other than —H) at one of $R^0$ or $R^1$. In certain embodiments, $R^2$ is —H, and $R^0$ and $R^1$ are not —H. In other embodiments, $R^0$, $R^1$ and $R^2$ are not —H.

In certain embodiments of any of the foregoing or following, compounds of Formula I are inhibitors of SHMT, such as are capable of inhibiting an activity of an SHMT enzyme. In certain embodiments, compounds of Formula I are SHMT2 inhibitors and, optionally, are also inhibitors of SHMT1. In certain embodiments, compounds of Formula I are SHMT2 inhibitors, but do not inhibit SHMT1. In certain embodiments, compounds of Formula I inhibit SHMT2 with an IC50 of less than 5000 nM and, optionally, inhibit SHMT1 with an IC50 of less than 5000 nM. In certain embodiments, compound of Formula I inhibit SHMT2 with an IC50 of less than 2000 nM, less than 1500 nM, less than 800 nM, less than 500 nM, less than 250 nM, less than 150 nM, or less than 50 nM. In certain embodiments, such compounds also inhibit SHMT1 with an IC50 of less than 5000 nM. In certain embodiments, such compounds inhibit SHMT1 with an IC50 of less than 1000 nM, less than 750 nM, less than 500 nM, less than 250 nM, less than 100 nM, or less than 50 nM.

In certain embodiments, compounds of Formula I described using any combination of structural and/or functional activity, including any combination of one or more features described above or herein, are provided (and may be provided as an isolated or purified form or as a pharmaceutical composition). In certain embodiments, any such compounds of the disclosure may be used in any of the methods described herein, such as to inhibit SHMT activity in vitro or in vivo, or to treat cancer.

In one aspect, the disclosure provides compounds represented by general Formula (II):

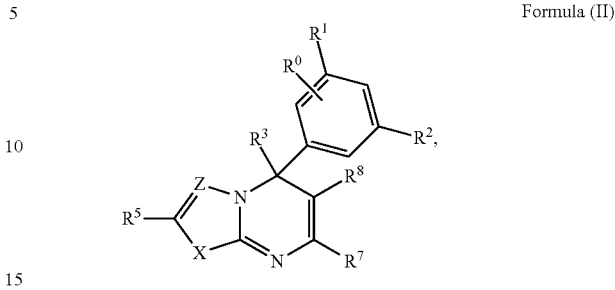

Formula (II)

wherein:
Z is N or $CR^4$;
X is O, S, $CH_2$, or $NR^6$;
$R^0$, $R^1$ and $R^2$ are each independently selected from —H, halogen, hydroxyl, nitro, nitrile, —$SOR^{11}$, —$S(O)_2R^{11}$, —$S(O)_2NR^{10}R^{12}$, —$OR^{11}$, —$OC(O)R^{12}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;
$R^3$ is selected from —H, halogen, hydroxyl, nitro, nitrile, —$SOR^{11}$, —$S(O)_2R^{11}$, —$S(O)_2NR^{10}R^{12}$, —$OR^{11}$, —$OC(O)R^{12}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;
$R^4$ is selected from —H, —$NR^{10}R^{12}$, —$C(O)NR^{10}R^{12}$, —$N(R^{12})C(O)R^{11}$, nitrile, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;
$R^5$ is selected from —H, —$NR^{10}R^{12}$, —$C(O)NR^{10}R^{12}$, —$N(R^{12})C(O)R^{11}$, nitrile, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl, or $R^5$ and $R^4$ taken together with the respective carbon atom to which they are attached form a substituted or unsubstituted 4-12 membered ring;
$R^6$ is selected from H, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, or substituted or unsubstituted heteroarylalkyl;
$R^7$ and $R^8$ are each independently selected from —H, —$NR^{10}R^{12}$, —$C(O)NR^{10}R^{12}$, —$N(R^{12})C(O)R^{11}$, nitrile, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

each occurrence of $R^{11}$ is independently selected from substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl; and each occurrence of $R^{10}$ and $R^{12}$ is each independently selected from —H, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl, or a pharmaceutically acceptable salt thereof.

In certain embodiments, the compounds of the disclosure, or a pharmaceutically acceptable salt thereof, are represented by Formula (IIa) (wherein the R groups are as described above for Formula (II)):

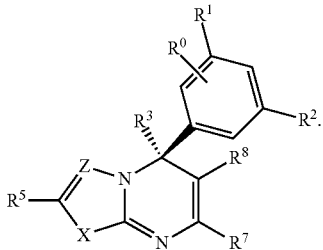

Formula (IIa)

In certain embodiments, the compounds of the disclosure, or a pharmaceutically acceptable salt thereof, are represented Formula (IIb) (wherein the R groups are as described above for Formula (II)):

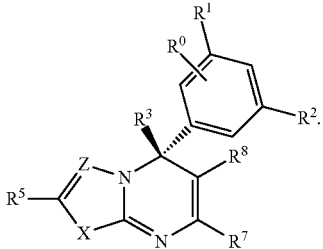

Formula (IIb)

In certain embodiments of any of the foregoing or following, any of the compounds of Formula II (including of Formula IIa or IIb) described herein, or a pharmaceutically acceptable salt thereof, are capable of inhibiting activity of an SHMT enzyme (e.g., are SHMT inhibitors, such as an SHMT2 inhibitor). Any such compounds described based on any of the structural features described herein may, in certain embodiments, also be described based on any of the functional features described herein (e.g., binding affinity for SHMT1 and/or 2, IC50, selectivity, inhibitory effect on serine flux or mitochondrial serine flux, etc.)

In certain embodiments of any of the foregoing or following, a compound of the disclosure is provided in isolated or substantially purified form, such as a substantially purified stereoisomer of a compound of the disclosure. Without being bound by theory, compounds of the disclosure have a stereocenter. Thus, in certain embodiments, substantially purified stereoisomers are provided and are suitable in any of the methods described herein.

In certain embodiments, the disclosure provides a pharmaceutically acceptable salt of any of the compounds of the disclosure.

In certain embodiments of any of the foregoing or following, $R^0$, $R^1$ and $R^2$ are each independently selected from —H, halogen, hydroxyl, nitro, nitrile, —$SOR^{11}$, —$S(O)_2R^{11}$, —$S(O)_2NR^{10}R^{12}$, —$OR^{11}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy.

In certain embodiments of any of the foregoing or following, $R^0$ is selected from hydroxyl, —$S(O)_2R^{11}$, —$S(O)_2NR^{10}R^{12}$, —$OR^{11}$, —$C(O)NR^{10}R^{12}$, —$NR^{10}R^{12}$, —$N(R^{12})C(O)R^{11}$, or —$NS(O)_2R^{12}$. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from —H, halogen, hydroxyl, nitro, nitrile, —$OR^{11}$, substituted or unsubstituted $C_1$-$C_6$ alkyl, substituted or unsubstituted $C_1$-$C_6$ haloalkyl, substituted or unsubstituted $C_1$-$C_6$ haloalkoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from —H, methoxy, fluoro, chloro, bromo, hydroxyl, nitro, nitrile, methyl, trifluoromethyl, or trifluoromethoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^3$ is selected from —H, halogen, hydroxyl, nitro, nitrile, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected from methyl, ethyl, propyl, isopropyl, cyclopropyl, or cyclobutyl. In certain embodiments, any of the foregoing may be optionally substituted.

In certain embodiments of any of the foregoing or following, $R^3$ is isopropyl or cyclopropyl. In certain embodiments, any of the foregoing may be optionally substituted.

In certain embodiments of any of the foregoing or following, $R^4$ and $R^5$ are each independently selected from —H, substituted or unsubstituted $C_1$-$C_6$ alkyl, substituted or unsubstituted cycloalkyl, substituted or unsubstituted aryl, substituted or unsubstituted heteroaryl, or substituted or unsubstituted arylalkyl.

In certain embodiments of any of the foregoing or following, $R^4$ and $R^5$ are each independently selected from —H, substituted or unsubstituted $C_1$-$C_6$ alkyl, substituted or unsubstituted cycloalkyl, substituted or unsubstituted aryl, or substituted or unsubstituted arylalkyl.

In certain embodiments of any of the foregoing or following, $R^4$ and $R^5$ are each independently selected from —H, methyl, ethyl, propyl, isopropyl, cyclopropyl, cyclobutyl, cyclopentyl, cyclohexyl, phenyl or benzyl. In certain embodiments, any of the foregoing, except —H, may be optionally substituted.

In certain embodiments of any of the foregoing or following, $R^4$ and $R^5$ are independently —H or methyl. In certain embodiments, methyl may be optionally substituted.

In certain embodiments of any of the foregoing or following, $R^5$ and $R^4$ taken together with the respective carbon atom to which they are attached form a 4-12 membered ring selected from substituted or unsubstituted aryl, or substituted or unsubstituted heteroaryl.

In certain embodiments of any of the foregoing or following, $R^5$ and $R^4$ taken together with the respective carbon atom to which they are attached form a substituted or unsubstituted 4-12 membered ring containing 0-4 heteroatoms (0, 1, 2, 3 or 4) independently selected from N, O, or S.

In certain embodiments of any of the foregoing or following, the 4-12 membered ring is a monocyclic ring. In certain embodiments of any of the foregoing or following, the 4-12 membered ring is a polycyclic ring. In certain embodiments of any of the foregoing or following, the 4-12 membered ring is a bicyclic ring. In certain embodiments of any of the foregoing or following, when the 4-12 membered ring is a polycyclic ring, each ring is independently selected from saturated or unsaturated, and each ring may independently contain one or more heteroatoms (e.g., for a total of 1, 2, 3, 4 or 4 heteroatoms).

In certain embodiments of any of the foregoing or following, $R^5$ and $R^4$ taken together with the respective carbon atom to which they are attached form a phenyl ring. In certain embodiments, the phenyl ring may be optionally substituted.

In certain embodiments of any of the foregoing or following, $R^6$ is selected from H, substituted or unsubstituted $C_1$-$C_6$ alkyl, substituted or unsubstituted cycloalkyl, substituted or unsubstituted aryl, substituted or unsubstituted heteroaryl, or substituted or unsubstituted arylalkyl.

In certain embodiments of any of the foregoing or following, $R^6$ is selected from —H, methyl, ethyl, isopropyl, cyclopropyl, cyclobutyl, cyclopentyl, cyclohexyl, phenyl, pyridyl, or benzyl. In certain embodiments, any of the foregoing may be optionally substituted.

In certain embodiments of any of the foregoing or following, $R^6$ is —H.

In certain embodiments of any of the foregoing or following, $R^7$ and $R^8$ are each independently selected from —H, —NR$^{10}$R$^{12}$, —C(O)NR$^{10}$R$^{12}$, —N(R$^{12}$)C(O)R$^{11}$, nitrile, methyl, ethyl, isopropyl, cyclopropryl, cyclobutyl, cyclopentyl, cyclohexyl, phenyl, or benzyl.

In certain embodiments of any of the foregoing or following, $R^7$ is selected from —H, —NH$_2$, methyl, or phenyl. In certain embodiments, any of the foregoing except —H, may be optionally substituted.

In certain embodiments of any of the foregoing or following, $R^8$ is selected from —H, nitrile, or —C(O)NH$_2$. In certain embodiments, —C(O)NH$_2$ may be optionally substituted.

In certain embodiments of any of the foregoing or following, each occurrence of $R^{11}$ is independently selected from substituted or unsubstituted $C_1$-$C_6$ alkyl or substituted or unsubstituted cycloalkyl. In certain embodiments, there is no occurrence of $R^{11}$.

In certain embodiments of any of the foregoing or following, each occurrence of $R^{10}$ and $R^{12}$ is each independently selected from —H, substituted or unsubstituted $C_1$-$C_6$ alkyl, or substituted or unsubstituted cycloalkyl, such as from —H, or substituted or unsubstituted $C_1$-$C_6$ alkyl. In certain embodiments, each occurrence of $R^{10}$ and $R^{12}$ is —H. In certain embodiments, there is no occurrence of $R^{10}$ and/or $R^{12}$.

In certain embodiments of any of the foregoing or following, the disclosure provides a pharmaceutically acceptable salt thereof or an enantiomer thereof.

In certain embodiments of any of the foregoing or following, the $R^0$, $R^1$ and $R^2$ are not all simultaneously —H. In other embodiments, $R^0$ is —H and the ring to which it is attached, is substituted with a single substituent (other than —H) at one of $R^1$ or $R^2$. In certain embodiments, $R^0$ is —H, and $R^1$ and $R^2$ are not —H. In other embodiments, $R^1$ is —H and the ring to which it is attached is substituted with a single substituent (other than —H) at one of $R^0$ or $R^2$. In certain embodiments, $R^1$ is —H, and $R^0$ and $R^2$ are not —H. In other embodiments, $R^2$ is —H and the ring to which it is attached is substituted with a single substituent (other than —H) at one of $R^0$ or $R^1$. In certain embodiments, $R^2$ is —H, and $R^0$ and $R^1$ are not —H. In other embodiments, $R^0$, $R^1$ and $R^2$ are not —H.

In certain embodiments of any of the foregoing or following, compounds of Formula II are inhibitors of SHMT, such as are capable of inhibiting an activity of an SHMT enzyme. In certain embodiments, compounds of Formula II are SHMT2 inhibitors and, optionally, are also inhibitors of SHMT1. In certain embodiments, compounds of Formula II are SHMT2 inhibitors, but do not inhibit SHMT1. In certain embodiments, compounds of Formula II inhibit SHMT2 with an IC50 of less than 5000 nM and, optionally, inhibit SHMT1 with an IC50 of less than 5000 nM. In certain embodiments, compound of Formula II inhibit SHMT2 with an IC50 of less than 2000 nM, less than 1500 nM, less than 800 nM, less than 500 nM, less than 250 nM, less than 150 nM, or less than 50 nM. In certain embodiments, such compounds also inhibit SHMT1 with an IC50 of less than 5000 nM. In certain embodiments, such compounds inhibit SHMT1 with an IC50 of less than 1000 nM, less than 750 nM, less than 500 nM, less than 250 nM, less than 100 nM, or less than 50 nM.

In certain embodiments, compounds of Formula II described using any combination of structural and/or functional activity, including any combination of one or more features described above or herein, are provided (and may be provided as an isolated or purified form or as a pharmaceutical composition). In certain embodiments, any such compounds of the disclosure may be used in any of the methods described herein, such as to inhibit SHMT activity in vitro or in vivo, or to treat cancer.

In certain embodiments, when Z is N, and $R^8$ is H, $R^7$ cannot be substituted or unsubstituted aryl.

In certain embodiments, the compound of formula II, IIa, or IIb is not

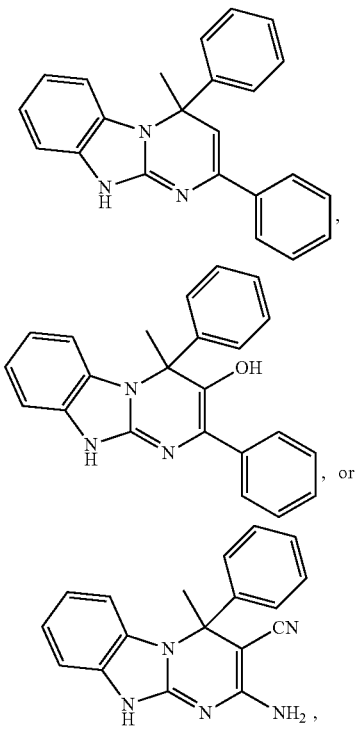

,

In certain embodiments, when $R^4$ and $R^5$ taken together with the respective carbon atoms to which they are attached for a substituted aryl ring, $R^8$ is not —H, —OH, or —CN.

In certain embodiments, the compound of formula (II), (IIa), or (IIb) is:

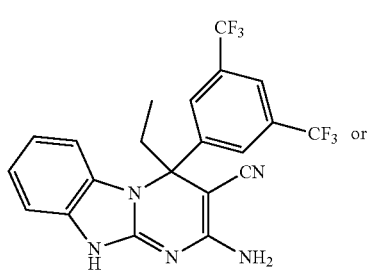

or

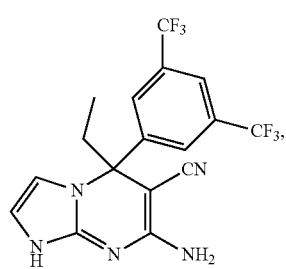

or a pharmaceutically acceptable salt thereof.

In one aspect, the disclosure provides compounds represented by general by Formula (III):

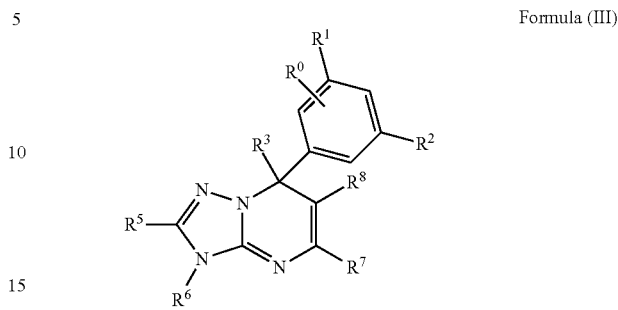

Formula (III)

wherein:
$R^0$, $R^1$ and $R^2$ are each independently selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted C$_1$-C$_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted C$_1$-C$_6$ haloalkyl, or substituted or unsubstituted C$_1$-C$_6$ haloalkoxy;
$R^3$ is selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted C$_1$-C$_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted C$_1$-C$_6$ haloalkyl, or substituted or unsubstituted C$_1$-C$_6$ haloalkoxy;
$R^5$ is selected from —H, —NR$^{10}$R$^{12}$, —C(O)NR$^{10}$R$^{12}$, —N(R$^{12}$)C(O)R$^{11}$, nitrile, substituted or unsubstituted C$_1$-C$_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;
$R^6$ is selected from —H, substituted or unsubstituted C$_1$-C$_6$ alkyl, substituted or unsubstituted cycloalkyl, substituted or unsubstituted heterocyclyl, substituted or unsubstituted aryl, substituted or unsubstituted heteroaryl substituted or unsubstituted arylalkyl, or substituted or unsubstituted heteroarylalkyl;
$R^7$ and $R^8$ are each independently selected from —H, —NR$^{10}$R$^{12}$, —C(O)NR$^{10}$R$^{12}$, —N(R$^{12}$)C(O)R$^{11}$, nitrile, substituted or unsubstituted C$_1$-C$_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;
each occurrence of R$^{11}$ is independently selected from substituted or unsubstituted C$_1$-C$_6$ alkyl, substituted or unsubstituted cycloalkyl, substituted or unsubstituted heterocyclyl, substituted or unsubstituted aryl, or substituted or unsubstituted heteroaryl; and
each occurrence of R$^{10}$ and R$^{12}$ is each independently selected from —H, substituted or unsubstituted C$_1$-C$_6$ alkyl, substituted or unsubstituted cycloalkyl, substituted or unsubstituted heterocyclyl, substituted or unsubstituted aryl, or substituted or unsubstituted heteroaryl, or a pharmaceutically acceptable salt thereof.

In certain embodiments, the compounds of the disclosure, or a pharmaceutically acceptable salt thereof, are represented by Formula (IIIa) (wherein the R groups are as described above for Formula (III)):

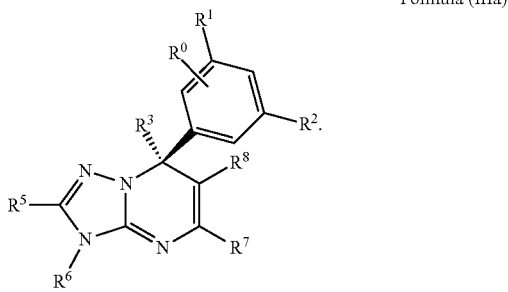

Formula (IIIa)

In certain embodiments, the compounds of the disclosure, or a pharmaceutically acceptable salt thereof, are represented by Formula (IIIb) (wherein the R groups are as described above for Formula (III)):

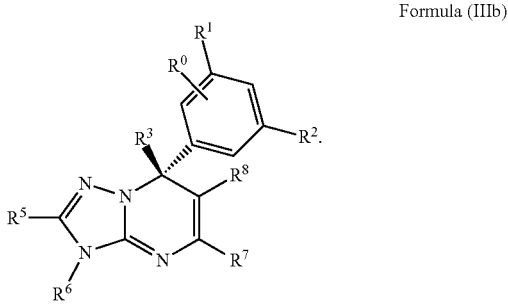

Formula (IIIb)

In certain embodiments, any of the compounds of Formula (III) (including of Formula (IIIa) or (IIIb)) described herein, or a pharmaceutically acceptable salt thereof, are capable of inhibiting activity of an SHMT enzyme (e.g., are SHMT inhibitors, such as an SHMT2 inhibitor). Any such compounds described based on any of the structural features described herein may, in certain embodiments, also be described based on any of the functional features described herein (e.g., binding affinity for SHMT1 and/or 2, IC50, selectivity, inhibitory effect on serine flux or mitochondrial serine flux, etc.).

In certain embodiments of any of the foregoing or following, a compound of the disclosure is provided in isolated or substantially purified form, such as a substantially purified stereoisomer of a compound of the disclosure. Without being bound by theory, compounds of the disclosure have a stereocenter. Thus, in certain embodiments, substantially purified stereoisomers are provided and are suitable in any of the methods described herein.

In certain embodiments, the disclosure provides a pharmaceutically acceptable salt of any of the compounds of the disclosure.

In certain embodiments of any of the foregoing or following, $R^0$, $R^1$ and $R^2$ are each independently selected from —H, halogen, hydroxyl, nitro, nitrile, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, or —NS(O)$_2$R$^{12}$, substituted or unsubstituted $C_1$-$C_6$ alkyl, substituted or unsubstituted cycloalkyl, substituted or unsubstituted $C_1$-$C_6$ haloalkyl, or substituted or unsubstituted $C_1$-$C_6$ haloalkoxy.

In certain embodiments of any of the foregoing or following, $R^0$ is selected from hydroxyl, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, or —NS(O)$_2$R$^{12}$. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from —H, halogen, hydroxyl, nitro, nitrile, —OR$^{11}$, substituted or unsubstituted $C_1$-$C_6$ alkyl, substituted or unsubstituted $C_1$-$C_6$ haloalkyl, or substituted or unsubstituted $C_1$-$C_6$ haloalkoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from —H, methoxy, fluoro, chloro, bromo, hydroxyl, nitro, nitrile, methyl, trifluoromethyl, or trifluoromethoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^3$ is selected from —H, halogen, hydroxyl, nitro, nitrile, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected from methyl, ethyl, propyl, isopropyl, cyclopropyl, or cyclobutyl. In certain embodiments, any of the foregoing may be optionally substituted.

In certain embodiments of any of the foregoing or following, $R^3$ is isopropyl or cyclopropyl. In certain embodiments, any of the foregoing may be optionally substituted.

In certain embodiments of any of the foregoing or following, $R^5$ is selected from —H, methyl, ethyl, propyl, isopropyl, cyclopropyl, cyclobutyl, cyclopentyl, cyclohexyl, phenyl or benzyl. In certain embodiments, any of the foregoing except —H, may be optionally substituted.

In certain embodiments of any of the foregoing or following, $R^5$ is —H.

In certain embodiments of any of the foregoing or following, $R^6$ is selected from H, substituted or unsubstituted $C_1$-$C_6$ alkyl, substituted or unsubstituted cycloalkyl, substituted or unsubstituted aryl, substituted or unsubstituted heteroaryl, or substituted or unsubstituted arylalkyl.

In certain embodiments of any of the foregoing or following, $R^6$ is selected from —H, methyl, ethyl, isopropyl, cyclopropyl, cyclobutyl, cyclopentyl, cyclohexyl, phenyl, pyridyl or benzyl. In certain embodiments, any of the foregoing except —H, may be optionally substituted.

In certain embodiments of any of the foregoing or following, $R^6$ is —H.

In certain embodiments of any of the foregoing or following, $R^7$ and $R^8$ are each independently selected from —H, —$NR^{10}R^{12}$, —$C(O)NR^{10}R^{12}$, —$N(R^{12})C(O)R^{11}$, nitrile, methyl, ethyl, isopropyl, cyclopropryl, cyclobutyl, cyclopentyl, cyclohexyl, phenyl, or benzyl.

In certain embodiments of any of the foregoing or following, $R^7$ is selected from —$NH_2$, methyl, or phenyl. In certain embodiments, any of the foregoing, may be optionally substituted.

In certain embodiments of any of the foregoing or following, $R^8$ is selected from —H, nitrile, or —$C(O)NH_2$. In certain embodiments, —$C(O)NH_2$ may be optionally substituted.

In certain embodiments of any of the foregoing or following, each occurrence of $R^{11}$ is independently selected from substituted or unsubstituted $C_1$-$C_6$ alkyl or substituted or unsubstituted cycloalkyl. In certain embodiments, there is no occurrence of $R^{11}$.

In certain embodiments of any of the foregoing or following, each occurrence of $R^{10}$ and $R^{12}$ is each independently selected from —H, substituted or unsubstituted $C_1$-$C_6$ alkyl, or substituted or unsubstituted cycloalkyl, such as from —H, or substituted or unsubstituted $C_1$-$C_6$ alkyl. In certain embodiments, each occurrence of $R^{10}$ and $R^{12}$ is —H. In certain embodiments, there is no occurrence of $R^{10}$ and/or $R^{12}$.

In certain embodiments of any of the foregoing or following, $R^0$ is selected from —H, halogen, hydroxyl, nitro, nitrile, —$S(O)_2R^{11}$, —$S(O)_2NR^{10}R^{12}$, —$OR^{11}$, —$C(O)NR^{10}R^{12}$, —$NR^{10}R^{12}$, —$N(R^{12})C(O)R^{11}$, or —$NS(O)_2R^{12}$, substituted or unsubstituted $C_1$-$C_6$ alkyl, substituted or unsubstituted $C_1$-$C_6$ haloalkyl, or substituted or unsubstituted $C_1$-$C_6$ haloalkoxy;

$R^1$ and $R^2$ are each independently selected from —H, methoxy, fluoro, chloro, bromo, hydroxyl, nitro, nitrile, methyl, or trifluoromethyl;

$R^3$ is selected from methyl, ethyl, propyl, isopropyl, cyclopropyl, or cyclobutyl;

$R^5$ is selected from —H, methyl, ethyl, propyl or isopropyl;

$R^6$ is selected from —H, methyl, ethyl, isopropyl, cyclopropyl, cyclobutyl, cyclopentyl, cyclohexyl, phenyl or benzyl; and $R^7$ and $R^8$ are each independently selected from —H, —$NH_2$, —$C(O)NH_2$, nitrile, methyl, ethyl, isopropyl, cyclopropryl, cyclobutyl, cyclopentyl, cyclohexyl, phenyl, or benzyl.

In certain embodiments of any of the foregoing or following, $R^0$ is selected from —H, hydroxyl, —$S(O)_2R^{11}$, —$S(O)_2NR^{10}R^{12}$, —$OR^{11}$, —$C(O)NR^{10}R^{12}$, —$NR^{10}R^{12}$, —$N(R^{12})C(O)R^{11}$, or —$NS(O)_2R^{12}$;

$R^1$ and $R^2$ are each trifluoromethyl;

$R^3$ is isopropyl or cyclopropyl;

$R^5$ is —H;

$R^6$ is —H;

$R^7$ is selected from —$NH_2$, methyl, or phenyl; and $R^8$ is selected from H, nitrile, or —$C(O)NH_2$.

In certain embodiments, the compound is selected from:

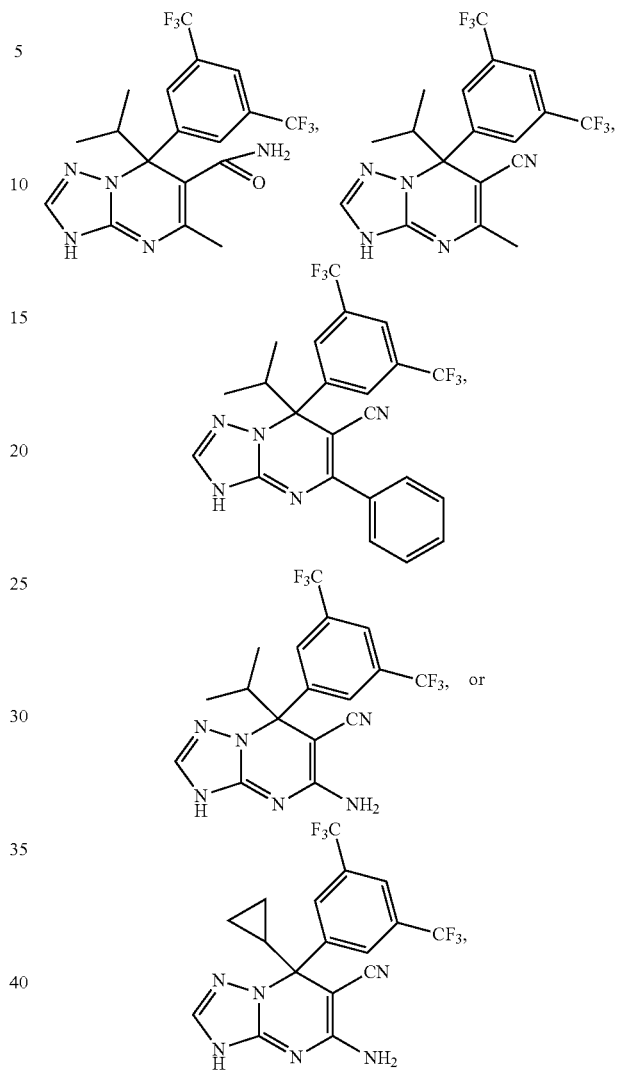

or a pharmaceutically acceptable salt thereof.

In certain embodiments of any of the foregoing or following, the disclosure provides a pharmaceutically acceptable salt thereof or an enantiomer thereof.

In certain embodiments of any of the foregoing or following, the $R^0$, $R^1$ and $R^2$ are not all simultaneously —H. In other embodiments, $R^0$ is —H and the ring to which it is attached, is substituted with a single substituent (other than —H) at one of $R^1$ or $R^2$. In certain embodiments, $R^0$ is —H, and $R^1$ and $R^2$ are not —H. In other embodiments, $R^1$ is —H and the ring to which it is attached is substituted with a single substituent (other than —H) at one of $R^0$ or $R^2$. In certain embodiments, $R^1$ is —H, and $R^0$ and $R^2$ are not —H. In other embodiments, $R^2$ is —H and the ring to which it is attached is substituted with a single substituent (other than —H) at one of $R^0$ or $R^1$. In certain embodiments, $R^2$ is —H, and $R^0$ and $R^1$ are not —H. In other embodiments, $R^0$, $R^1$ and $R^2$ are not —H.

In certain embodiments of any of the foregoing or following, compounds of Formula III are inhibitors of SHMT, such as are capable of inhibiting an activity of an SHMT enzyme. In certain embodiments, compounds of Formula III are SHMT2 inhibitors and, optionally, are also inhibitors of SHMT1. In certain embodiments, compounds of Formula III are SHMT2 inhibitors, but do not inhibit SHMT1. In certain embodiments, compounds of Formula III inhibit SHMT2 with an IC50 of less than 5000 nM and, optionally, inhibit SHMT1 with an IC50 of less than 5000 nM. In certain embodiments, compound of Formula III inhibit SHMT2 with an IC50 of less than 2000 nM, less than 1500 nM, less than 800 nM, less than 500 nM, less than 250 nM, less than 150 nM, or less than 50 nM. In certain embodiments, such compounds also inhibit SHMT1 with an IC50 of less than 5000 nM. In certain embodiments, such compounds inhibit SHMT1 with an IC50 of less than 1000 nM, less than 750 nM, less than 500 nM, less than 250 nM, less than 100 nM, or less than 50 nM.

In certain embodiments, compounds of Formula III described using any combination of structural and/or functional activity, including any combination of one or more features described above or herein, are provided (and may be provided as an isolated or purified form or as a pharmaceutical composition). In certain embodiments, any such compounds of the disclosure may be used in any of the methods described herein, such as to inhibit SHMT activity in vitro or in vivo, or to treat cancer.

In certain embodiments, when $R^8$ is H, $R^7$ is not a substituted or unsubstituted aryl.

In one aspect, the disclosure provides compounds represented by general Formula (IV):

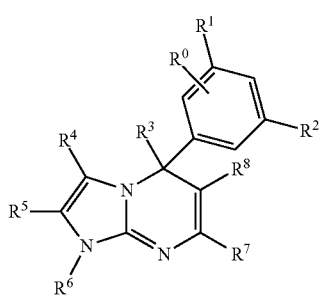

Formula (IV)

wherein:
$R^0$, $R^1$ and $R^2$ are each independently selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted C$_1$-C$_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted C$_1$-C$_6$ haloalkyl, or substituted or unsubstituted C$_1$-C$_6$ haloalkoxy;

$R^3$ is selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted C$_1$-C$_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted C$_1$-C$_6$ haloalkyl, or substituted or unsubstituted C$_1$-C$_6$ haloalkoxy;

$R^4$ and $R^5$ are independently selected from H, —NR$^{10}$R$^{12}$, —C(O)NR$^{10}$R$^{12}$, —N(R$^{12}$)C(O)R$^{11}$, nitrile, substituted or unsubstituted C$_1$-C$_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl, or $R^5$ and $R^4$ taken together with the respective carbon atom to which they are attached form a substituted or unsubstituted 4-12 membered ring;

$R^6$ is selected from —H, substituted or unsubstituted C$_1$-C$_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, or substituted or unsubstituted heteroarylalkyl;

$R^7$ and $R^8$ are each independently selected from —H, —NR$^{10}$R$^{12}$, —C(O)NR$^{10}$R$^{12}$, —N(R$^{12}$)C(O)R$^{11}$, nitrile, substituted or unsubstituted C$_1$-C$_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

each occurrence of R$^{11}$ is independently selected from substituted or unsubstituted C$_1$-C$_6$ alkyl, substituted or unsubstituted cycloalkyl, substituted or unsubstituted heterocyclyl, substituted or unsubstituted aryl, or substituted or unsubstituted heteroaryl; and each occurrence of R$^{10}$ and R$^{12}$ is each independently selected from —H, substituted or unsubstituted C$_1$-C$_6$ alkyl, substituted or unsubstituted cycloalkyl, substituted or unsubstituted heterocyclyl, substituted or unsubstituted aryl, or substituted or unsubstituted heteroaryl, or a pharmaceutically acceptable salt thereof.

In certain embodiments of any of the foregoing or following, the compounds of the disclosure, or a pharmaceutically acceptable salt thereof, are represented by Formula (IVa) (wherein the R groups are as described above for Formula (IV)):

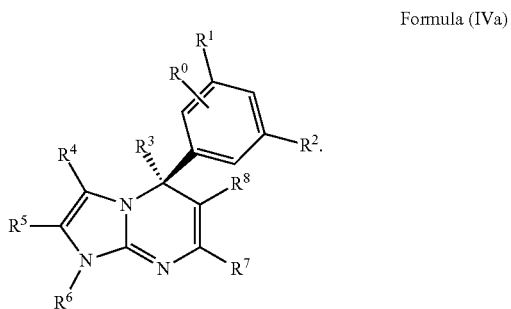

Formula (IVa)

In certain embodiments of any of the foregoing or following, the compounds of the disclosure, or a pharmaceutically acceptable salt thereof, are represented by Formula (IVb) (wherein the R groups are as described above for Formula (IV)):

Formula (IVb)

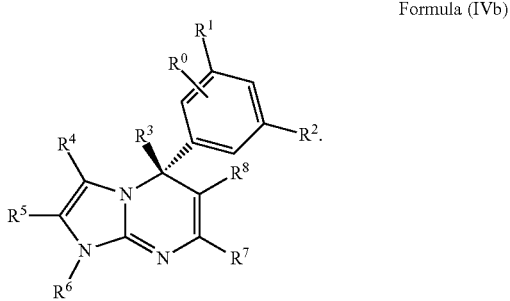

In certain embodiments, any of the compounds of Formula (IV) (including of Formula (Iva) or (IVb)) described herein, or a pharmaceutically acceptable salt thereof, are capable of inhibiting activity of an SHMT enzyme (e.g., are SHMT inhibitors, such as an SHMT2 inhibitor). Any such compounds described based on any of the structural features described herein may, in certain embodiments, also be described based on any of the functional features described herein (e.g., binding affinity for SHMT1 and/or 2, IC50, selectivity, inhibitory effect on serine flux or mitochondrial serine flux, etc.)

In certain embodiments of any of the foregoing or following, a compound of the disclosure is provided in isolated or substantially purified form, such as a substantially purified stereoisomer of a compound of the disclosure. Without being bound by theory, compounds of the disclosure have a stereocenter. Thus, in certain embodiments, substantially purified stereoisomers are provided and are suitable in any of the methods described herein.

In certain embodiments, the disclosure provides a pharmaceutically acceptable salt of any of the compounds of the disclosure.

In certain embodiments of any of the foregoing or following, $R^0$, $R^1$ and $R^2$ are each independently selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy.

In certain embodiments of any of the foregoing or following, $R^0$ is selected from hydroxyl, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, or —NS(O)$_2$R$^{12}$. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from —H, hydroxyl, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, or —NS(O)$_2$R$^{12}$.

In certain embodiments of any of the foregoing or following, $R^1$ and $R^2$ are each independently selected from —H, methoxy, fluoro, chloro, bromo, hydroxyl, nitro, nitrile, methyl, trifluoromethyl, or trifluoromethoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^3$ is selected from —H, halogen, hydroxyl, nitro, nitrile, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected from methyl, ethyl, propyl, isopropyl, cyclopropyl, or cyclobutyl. In certain embodiments, any of the foregoing, may be optionally substituted.

In certain embodiments of any of the foregoing or following, $R^3$ is isopropyl. In certain embodiments, isopropyl may be optionally substituted.

In certain embodiments of any of the foregoing or following, $R^4$ and $R^5$ are independently selected from H, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl.

In certain embodiments of any of the foregoing or following, $R^4$ and $R^5$ are each independently selected from —H, methyl, ethyl, propyl, isopropyl, cyclopropyl, cyclobutyl, cyclopentyl, cyclohexyl, phenyl or benzyl. In certain embodiments, any of the foregoing except —H, may be optionally substituted.

In certain embodiments of any of the foregoing or following, $R^4$ and $R^5$ are each independently —H or methyl. In certain embodiments, methyl may be optionally substituted.

In certain embodiments of any of the foregoing or following, $R^5$ and $R^4$ taken together with the respective carbon atoms to which they are attached form a substituted or unsubstituted 4-12 membered ring.

In certain embodiments of any of the foregoing or following, $R^5$ and $R^4$ taken together with the respective carbon atom to which they are attached form a 4-12 membered ring selected from substituted or unsubstituted aryl or substituted or unsubstituted heteroaryl.

In certain embodiments of any of the foregoing or following, $R^5$ and $R^4$ taken together with the respective carbon atom to which they are attached form a substituted or unsubstituted 4-12 membered ring containing 0-4 heteroatoms (0, 1, 2, 3 or 4) independently selected from N, O, or S.

In certain embodiments of any of the foregoing or following, the 4-12 membered ring is a monocyclic ring. In certain embodiments of any of the foregoing or following, the 4-12 membered ring is a polycyclic ring. In certain embodiments of any of the foregoing or following, the 4-12 membered ring is a bicyclic ring. In certain embodiments of any of the foregoing or following, when the 4-12 membered ring is a polycyclic ring, each ring is independently selected from saturated or unsaturated, and each ring may independently contain one or more heteroatoms.

In certain embodiments of any of the foregoing or following, $R^5$ and $R^4$ taken together with the respective carbon atom to which they are attached form a phenyl ring. In certain embodiments, the phenyl ring may be optionally substituted.

In certain embodiments of any of the foregoing or following, $R^6$ is selected from H, substituted or unsubstituted $C_1$-$C_6$ alkyl, substituted or unsubstituted cycloalkyl, substituted or unsubstituted aryl, substituted or unsubstituted heteroaryl, or substituted or unsubstituted arylalkyl.

In certain embodiments of any of the foregoing or following, $R^6$ is selected from —H, methyl, ethyl, isopropyl, cyclopropyl, cyclobutyl, cyclopentyl, cyclohexyl, phenyl, pyridyl, or benzyl. In certain embodiments, any of the foregoing except —H, may be optionally substituted.

In certain embodiments of any of the foregoing or following, $R^6$ is —H.

In certain embodiments of any of the foregoing or following, $R^7$ and $R^8$ are each independently selected from —H, —NR$^{10}$R$^{12}$, —C(O)NR$^{10}$R$^{12}$, —N(R$^{12}$)C(O)R$^{11}$, nitrile, methyl, ethyl, isopropyl, cyclopropryl, cyclobutyl, cyclopentyl, cyclohexyl, phenyl, or benzyl.

In certain embodiments of any of the foregoing or following, $R^7$ is selected from —H, —NH$_2$, methyl, or phenyl. In certain embodiments, any of the foregoing except —H, may be optionally substituted.

In certain embodiments of any of the foregoing or following, $R^8$ is selected from —H, nitrile, or —C(O)NH$_2$. In certain embodiments, —C(O)NH$_2$ may be optionally substituted.

In certain embodiments of any of the foregoing or following, each occurrence of $R^{11}$ is independently selected from substituted or unsubstituted $C_1$-$C_6$ alkyl or substituted or unsubstituted cycloalkyl. In certain embodiments, there is no occurrence of $R^{11}$.

In certain embodiments of any of the foregoing or following, each occurrence of $R^{10}$ and $R^{12}$ is each independently selected from —H, substituted or unsubstituted $C_1$-$C_6$ alkyl, or substituted or unsubstituted cycloalkyl, such as from —H, or substituted or unsubstituted $C_1$-$C_6$ alkyl. In certain embodiments, each occurrence of $R^{10}$ and $R^{12}$ is —H. In certain embodiments, there is no occurrence of $R^{10}$ and/or $R^{12}$.

In certain embodiments, the compound is selected from:

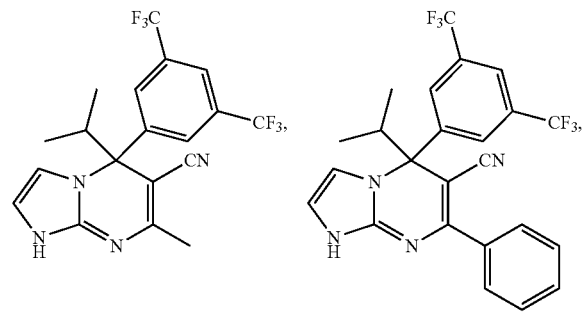

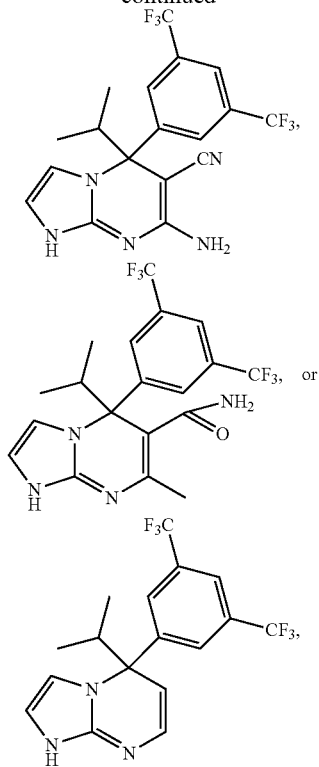

or a pharmaceutically acceptable salt thereof.

In certain embodiments, the compound of Formula (IV), (IVa), or (IVb) is:

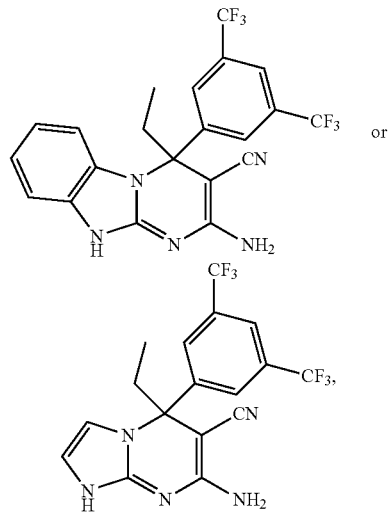

or a pharmaceutically acceptable salt thereof.

In certain embodiments of any of the foregoing or following, the disclosure provides a pharmaceutically acceptable salt thereof or an enantiomer thereof.

In certain embodiments of any of the foregoing or following, the $R^0$, $R^1$ and $R^2$ are not all simultaneously —H. In other embodiments, $R^0$ is —H and the ring to which it is attached, is substituted with a single substituent (other than —H) at one of $R^1$ or $R^2$. In certain embodiments, $R^0$ is —H, and $R^1$ and $R^2$ are not —H. In other embodiments, $R^1$ is —H and the ring to which it is attached is substituted with a single substituent (other than —H) at one of $R^0$ or $R^2$. In certain embodiments, $R^1$ is —H, and $R^0$ and $R^2$ are not —H. In other embodiments, $R^2$ is —H and the ring to which it is attached is substituted with a single substituent (other than —H) at one of $R^0$ or $R^1$. In certain embodiments, $R^2$ is —H, and $R^0$ and $R^1$ are not —H. In other embodiments, $R^0$, $R^1$ and $R^2$ are not —H.

In certain embodiments of any of the foregoing or following, compounds of Formula IV are inhibitors of SHMT, such as are capable of inhibiting an activity of an SHMT enzyme. In certain embodiments, compounds of Formula IV are SHMT2 inhibitors and, optionally, are also inhibitors of SHMT1. In certain embodiments, compounds of Formula IV are SHMT2 inhibitors, but do not inhibit SHMT1. In certain embodiments, compounds of Formula IV inhibit SHMT2 with an IC50 of less than 5000 nM and, optionally, inhibit SHMT1 with an IC50 of less than 5000 nM. In certain embodiments, compound of Formula IV inhibit SHMT2 with an IC50 of less than 2000 nM, less than 1500 nM, less than 800 nM, less than 500 nM, less than 250 nM, less than 150 nM, or less than 50 nM. In certain embodiments, such compounds also inhibit SHMT1 with an IC50 of less than 5000 nM. In certain embodiments, such compounds inhibit SHMT1 with an IC50 of less than 1000 nM, less than 750 nM, less than 500 nM, less than 250 nM, less than 100 nM, or less than 50 nM.

In certain embodiments, compounds of Formula IV described using any combination of structural and/or functional activity, including any combination of one or more features described above or herein, are provided (and may be provided as an isolated or purified form or as a pharmaceutical composition). In certain embodiments, any such compounds of the disclosure may be used in any of the methods described herein, such as to inhibit SHMT activity in vitro or in vivo, or to treat cancer.

In certain embodiments, the compound of Formula (IV), (Iva), or (IVb) is not

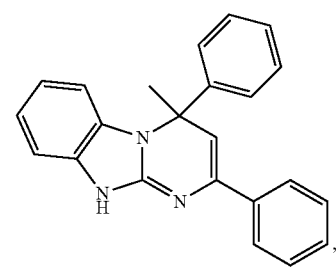

,

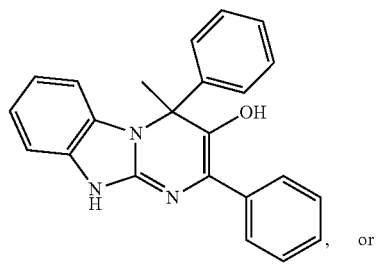

, or

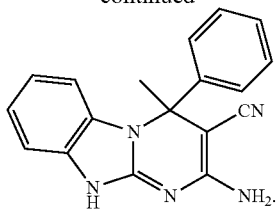

In one aspect, the disclosure provides compounds represented by general Formula (V):

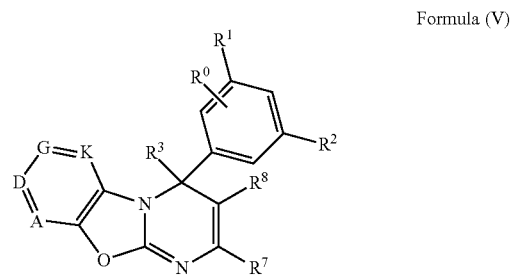

Formula (V)

wherein:
A, D, G and K are each independently N or $CR^{15}$, provided that no more than two of A, D, G, and K are N simultaneously;

$R^0$, $R^1$ and $R^2$ are each independently selected from —H, halogen, hydroxyl, nitro, —$SOR^{11}$, —$S(O)_2R^{11}$, —$S(O)_2NR^{10}R^{12}$, —$OR^{11}$, —$OC(O)R^{12}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$ substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;

$R^3$ is selected from —H, halogen, hydroxyl, nitro, nitrile, —$SOR^{11}$, —$S(O)_2R^{11}$, —$S(O)_2NR^{10}R^{12}$, —$OR^{11}$, —$OC(O)R^{12}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;

$R^7$ and $R^8$ are each independently selected from —H, —$NR^{10}R^{12}$, —$C(O)NR^{10}R^{12}$, —$N(R^{12})C(O)R^{11}$, nitrile, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

each occurrence of $R^{11}$ is independently selected from substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl;

each occurrence of $R^{10}$ and $R^{12}$ is each independently selected from —H, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl; and each occurrence of $R^{15}$ is independently selected from —H, halogen, hydroxyl, nitro, nitrile, substituted or unsubstituted $C_1$-$C_6$ alkoxy, substituted or unsubstituted $C_1$-$C_6$ alkyl, or substituted or unsubstituted $C_1$-$C_6$ haloalkyl, substituted or unsubstituted $C_1$-$C_6$ haloalkoxy, or a pharmaceutically acceptable salt thereof.

In certain embodiments, the compounds of the disclosure, or a pharmaceutically acceptable salt thereof, are represented by Formula (Va) (wherein the R groups are as described above for Formula (V)):

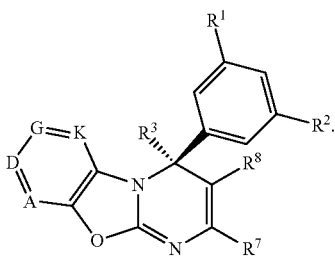

Formula (Va)

In certain embodiments, the compounds of the disclosure, or a pharmaceutically acceptable salt thereof, are represented by Formula (Vb) (wherein the R groups are as described above for Formula (V)):

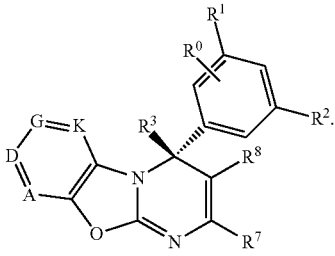

Formula (Vb)

In certain embodiments, any of the compounds of Formula (V) (including of Formula (Va) or (Vb)) described herein, or a pharmaceutically acceptable salt thereof, are capable of inhibiting activity of an SHMT enzyme (e.g., are SHMT inhibitors, such as an SHMT2 inhibitor). Any such compounds described based on any of the structural features described herein may, in certain embodiments, also be described based on any of the functional features described herein (e.g., binding affinity for SHMT1 and/or 2, IC50, selectivity, inhibitory effect on serine flux or mitochondrial serine flux, etc.)

In certain embodiments of any of the foregoing or following, a compound of the disclosure is provided in isolated or substantially purified form, such as a substantially purified stereoisomer of a compound of the disclosure. Without being bound by theory, compounds of the disclosure have a stereocenter. Thus, in certain embodiments, substantially purified stereoisomers are provided and are suitable in any of the methods described herein.

In certain embodiments, the disclosure provides a pharmaceutically acceptable salt of any of the compounds of the disclosure.

In certain embodiments of any of the foregoing or following, $R^0$, $R^1$, and $R^2$, are each independently selected from —H, halogen, hydroxyl, nitro, nitrile, —$SOR^{11}$, —$S(O)_2R^{11}$, —$S(O)_2NR^{10}R^{12}$, —$OR^{11}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy.

In certain embodiments of any of the foregoing or following, $R^0$ is selected from —H, hydroxyl, —$S(O)_2R^{11}$, —$S(O)_2NR^{10}R^{12}$, —$OR^{11}$, —$C(O)NR^{10}R^{12}$, —$NR^{10}R^{12}$, —$N(R^{12})C(O)R^{11}$, or —$NS(O)_2R^{12}$. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from —H, halogen, hydroxyl, nitro, nitrile, —$OR_{11}$, substituted or unsubstituted $C_1$-$C_6$ alkyl, or substituted or unsubstituted $C_1$-$C_6$ haloalkyl, substituted or unsubstituted $C_1$-$C_6$ haloalkoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from —H, methoxy, fluoro, chloro, bromo, hydroxyl, nitro, nitrile, methyl, or trifluoromethyl, or trifluoromethoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^3$ is selected from —H, halogen, hydroxyl, nitro, nitrile, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected from methyl, ethyl, propyl, isopropyl, cyclopropyl, or cyclobutyl. In certain embodiments, any of the foregoing, may be optionally substituted.

In certain embodiments, in of any of the foregoing or following, $R^3$ is isopropyl. In certain embodiments, isopropyl may be optionally substituted.

In certain embodiments of any of the foregoing or following, $R^7$ and $R^8$ are each independently selected from —H, —$NR^{10}R^{12}$, —$C(O)NR^{10}R^{12}$, —$N(R^{12})C(O)R^{11}$, nitrile, methyl, ethyl, isopropyl, cyclopropryl, cyclobutyl, cyclopentyl, cyclohexyl, phenyl, or benzyl. In certain embodiments, any of the foregoing except —H, may be optionally substituted.

In certain embodiments of any of the foregoing or following, $R^7$ is methyl or phenyl. In certain embodiments, any of the foregoing may be optionally substituted.

In certain embodiments of any of the foregoing or following, $R^8$ is nitrile or —C(O)NH$_2$. In certain embodiments, —C(O)NH$_2$ may be optionally substituted.

In certain embodiments of any of the foregoing or following, each occurrence of $R^{11}$ is independently selected from substituted or unsubstituted $C_1$-$C_6$ alkyl or substituted or unsubstituted cycloalkyl. In certain embodiments, there is no occurrence of $R^{11}$.

In certain embodiments of any of the foregoing or following, each occurrence of $R^{10}$ and $R^{12}$ is each independently selected from —H, substituted or unsubstituted $C_1$-$C_6$ alkyl, or substituted or unsubstituted cycloalkyl, such as from —H, or substituted or unsubstituted $C_1$-$C_6$ alkyl. In certain embodiments, each occurrence of $R^{10}$ and $R^{12}$ is —H. In certain embodiments, there is no occurrence of $R^{10}$ and/or $R^{12}$.

In certain embodiments of any of the foregoing or following, $R^0$ is independently selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;

$R^1$ and $R^2$ are each independently selected from —H, methoxy, fluoro, chloro, bromo, hydroxyl, nitro, nitrile, methyl, or trifluoromethyl;

$R^3$ is selected from methyl, ethyl, propyl, isopropyl, cyclopropyl, or cyclobutyl;

$R^7$ and $R^8$ are each independently selected from H, —NH$_2$, —C(O)NH$_2$, nitrile, methyl, ethyl, isopropyl, cyclopropryl, cyclobutyl, cyclopentyl, cyclohexyl, phenyl, or benzyl; and A, D, G and K is each independently selected from N or CR$^{15}$, wherein each occurrence of $R^{15}$ is independently selected from —H, halogen, hydroxyl, nitro, nitrile, substituted or unsubstituted $C_1$-$C_6$ alkoxy, substituted or unsubstituted $C_1$-$C_6$ alkyl, or substituted or unsubstituted $C_1$-$C_6$ haloalkyl, substituted or unsubstituted $C_1$-$C_6$ haloalkoxy.

In certain embodiments of any of the foregoing or following, $R^0$ is selected from —H, hydroxyl, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, or —NS(O)$_2$R$^{12}$;

$R^1$ and $R^2$ are each trifluoromethyl;

$R^3$ is isopropyl;

$R^7$ is —NH$_2$, methyl or phenyl;

$R^8$ is nitrile or —C(O)NH$_2$; and

A, D, G and K is each independently selected from N or CR$^{15}$, wherein each occurrence of $R^{15}$ is independently selected from —H, halogen, hydroxyl, nitro, nitrile, substituted or unsubstituted $C_1$-$C_6$ alkoxy, substituted or unsubstituted $C_1$-$C_6$ alkyl, or substituted or unsubstituted $C_1$-$C_6$ haloalkyl, substituted or unsubstituted $C_1$-$C_6$ haloalkoxy.

In certain embodiments, the compound is selected from:

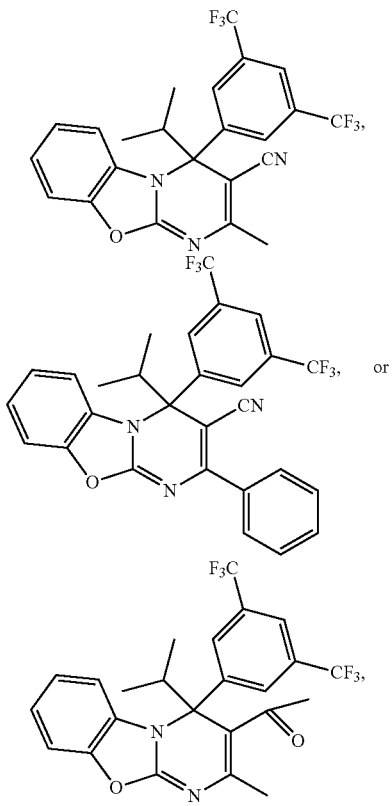

or a pharmaceutically acceptable salt thereof.

In certain embodiments of any of the foregoing or following, the disclosure provides a pharmaceutically acceptable salt thereof or an enantiomer thereof.

In certain embodiments of any of the foregoing or following, the $R^0$, $R^1$ and $R^2$ are not all simultaneously —H. In other embodiments, $R^0$ is —H and the ring to which it is attached, is substituted with a single substituent (other than —H) at one of $R^1$ or $R^2$. In certain embodiments, $R^0$ is —H, and $R^1$ and $R^2$ are not —H. In other embodiments, $R^1$ is —H and the ring to which it is attached is substituted with a single substituent (other than —H) at one of $R^0$ or $R^2$. In certain embodiments, $R^1$ is —H, and $R^0$ and $R^2$ are not —H. In other embodiments, $R^2$ is —H and the ring to which it is attached is substituted with a single substituent (other than —H) at one of $R^0$ or $R^1$. In certain embodiments, $R^2$ is —H, and $R^0$ and $R^1$ are not —H. In other embodiments, $R^0$, $R^1$ and $R^2$ are not —H.

In certain embodiments of any of the foregoing or following, compounds of Formula V are inhibitors of SHMT, such as are capable of inhibiting an activity of an SHMT enzyme. In certain embodiments, compounds of Formula (V) are SHMT2 inhibitors and, optionally, are also inhibitors of SHMT1. In certain embodiments, compounds of Formula V are SHMT2 inhibitors, but do not inhibit SHMT1. In certain embodiments, compounds of Formula V inhibit SHMT2 with an IC50 of less than 5000 nM and, optionally, inhibit SHMT1 with an IC50 of less than 5000 nM. In certain embodiments, compound of Formula (V) inhibit SHMT2 with an IC50 of less than 2000 nM, less than 1500 nM, less than 800 nM, less than 500 nM, less than 250 nM, less than 150 nM, or less than 50 nM. In certain embodiments, such compounds also inhibit SHMT1 with an IC50 of less than 5000 nM. In certain embodiments, such compounds inhibit SHMT1 with an IC50 of less than 1000 nM, less than 750 nM, less than 500 nM, less than 250 nM, less than 100 nM, or less than 50 nM.

In certain embodiments, compounds of Formula (V) described using any combination of structural and/or functional activity, including any combination of one or more features described above or herein, are provided (and may be provided as an isolated or purified form or as a pharmaceutical composition). In certain embodiments, any such compounds of the disclosure may be used in any of the methods described herein, such as to inhibit SHMT activity in vitro or in vivo, or to treat cancer.

In certain embodiments of any of the foregoing or following, the disclosure provides a pharmaceutical composition comprising a compound as disclosed herein, or a pharmaceutically acceptable salt thereof, and one or more pharmaceutically acceptable excipients and/or solvents.

In another aspect of any of the foregoing or following, the disclosure provides a method of inhibiting the activity of a mammalian serine hydroxymethyl transferase (SHMT) enzyme, comprising contacting the enzyme or a cell expressing the enzyme with a compound, or a pharmaceutically acceptable salt thereof, or a pharmaceutical composition as described herein.

In certain embodiments of any of the foregoing or following, the mammalian SHMT enzyme is a human SHMT enzyme.

In certain embodiments of any of the foregoing or following, the SHMT enzyme is SHMT2.

In certain embodiments of any of the foregoing or following, the method is an in vitro method comprising contacting the cell with the compound.

In another aspect of any of the foregoing or following, the disclosure provide a method for treating a disorder associated with activity of a serine hydroxymethyl transferase (SHMT) enzyme and/or associated with alterations in mitochondrial metabolism, such as mitochondrial folate metabolism, comprising administering to a subject in need thereof an effective amount of a compound, or a pharmaceutically acceptable salt thereof, or a pharmaceutical composition as described herein.

In certain embodiments of any of the foregoing or following, the SHMT enzyme is SHMT2, and wherein the subject is a human subject.

In certain embodiments of any of the foregoing or following, the disorder is cancer or an autoimmune disorder.

In certain embodiments of any of the foregoing or following, the cancer is selected from pediatric or adult leukemia, lymphoma, solid tumors of the lung, non-small cell lung cancer, mesothelioma, solid tumors of the breast, colon cancer, liver cancer, stomach cancer, prostate cancer, pancreatic cancer, ovarian cancer, uterus and female genital tract cancer, bladder cancer, head and neck cancer, osteosarcoma, or trophoblastic neoplasms.

In certain embodiments of any of the foregoing or following, the cancer is characterized by a Myc mutation.

In certain embodiments of any of the foregoing or following, the autoimmune disorder is selected from rheumatoid arthritis, dermatomyositis, psoriasis, lupus, sarcoidosis, Crohn's disease, eczema or vasculitis.

In certain embodiments of any of the foregoing or following, the method further comprises administering to the subject an additional anti-cancer agent.

In certain embodiments the additional anti-cancer agent comprises an anti-folate compound (e.g., a traditional anti-folate; an anti-folate that is not a selective inhibitor of SHMT).

In certain embodiments of any of the foregoing or following, the method further comprises administering to the subject a rescue therapy.

In certain embodiments of any of the foregoing or following, the rescue therapy is a formate salt or folinic acid.

In certain embodiments of any of the foregoing or following, the administration of a compound of the disclosure, or a pharmaceutically acceptable salt thereof, or a pharmaceutical composition comprising a compound of the disclosure, is part of a therapeutic regimen with one or more other agents or treatment modalities.

In another aspect, the disclosure provides a method of inhibiting the activity of a mammalian serine hydroxymethyl transferase (SHMT) enzyme, comprising contacting the enzyme or a cell expressing the enzyme with a compound of Formula (VI) or a pharmaceutically acceptable salt thereof:

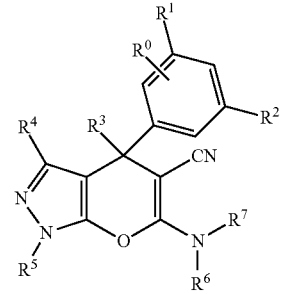

Formula (VI)

wherein:
$R^0$, $R^1$ and $R^2$ are each independently selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;
$R^3$ is selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;
$R^4$ is selected from H, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;
$R^5$, $R^6$ and $R^7$ are each independently selected from —H, —C(O)R$^{11}$, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl, or $R^5$ is selected from any of the foregoing and $R^6$ and $R^7$ taken together with the nitrogen atom to which they are attached form a substituted or unsubstituted 3-6 membered ring;

each occurrence of $R^{11}$ is independently selected from substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl; and each occurrence of $R^{10}$ and $R^{12}$ is each independently selected from —H, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In some embodiments, the compound is represented by Formula (VIa) (wherein the R groups are as described above for Formula (VI)):

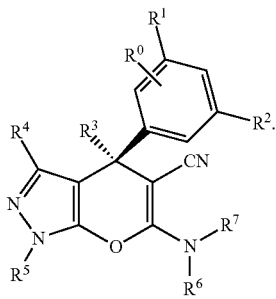

Formula (VIa)

In certain embodiments, the compound is represented by Formula (VIb) (wherein the R groups are as described above for Formula (VI)):

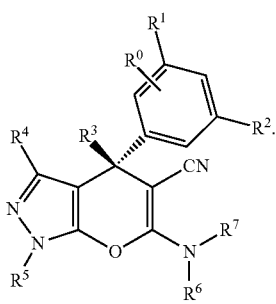

Formula (VIb)

In certain embodiments, any of the compounds of Formula (VI) (including of Formula (VIa) or (VIb)) described herein, or a pharmaceutically acceptable salt thereof, are capable of inhibiting activity of an SHMT enzyme (e.g., are SHMT inhibitors, such as an SHMT2 inhibitor). Any such compounds described based on any of the structural features described herein may, in certain embodiments, also be described based on any of the functional features described herein (e.g., binding affinity for SHMT1 and/or 2, IC50, selectivity, inhibitory effect on serine flux or mitochondrial serine flux, etc.)

In certain embodiments of any of the foregoing or following, a compound of the disclosure is provided in isolated or substantially purified form, such as a substantially purified stereoisomer of a compound of the disclosure. Without being bound by theory, compounds of the disclosure have a stereocenter. Thus, in certain embodiments, substantially purified stereoisomers are provided and are suitable in any of the methods described herein.

In certain embodiments, the disclosure provides a pharmaceutically acceptable salt of any of the compounds of the disclosure.

In another aspect, the disclosure provides a method for treating a disorder associated with activity of a serine hydroxymethyl transferase (SHMT) enzyme and/or associated with alterations in mitochondrial metabolism, such as mitochondrial folate metabolism, comprising administering to a subject in need thereof an effective amount of a compound of Formula (VI) or a pharmaceutically acceptable salt thereof:

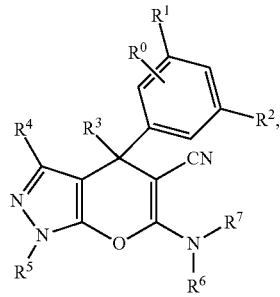

Formula (VI)

wherein:
$R^0$, $R^1$ and $R^2$ are each independently selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$ substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;

$R^3$ is selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;

$R^4$ is selected from H, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

$R^5$, $R^6$ and $R^7$ are each independently selected from —H, —C(O)R$^{11}$, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl, or $R^5$ is selected from any of the foregoing and $R^6$ and $R^7$ taken together with the nitrogen atom to which they are attached form a substituted or unsubstituted 3-6 membered ring;

each occurrence of $R^{11}$ is independently selected from substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl; and each occurrence of $R^{10}$ and $R^{12}$ is each independently selected from —H, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In some embodiments, the compound is represented by Formula (VIa) (wherein the R groups are as described above for Formula (VI)):

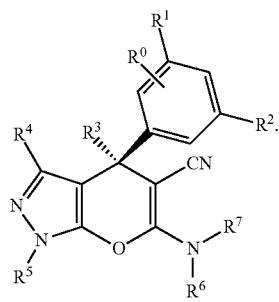

Formula (VIa)

In some embodiments, the compound is represented by Formula (VIb) (wherein the R groups are as described above for Formula (VI)):

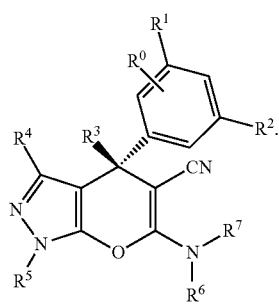

Formula (VIb)

In some embodiments, of any of the foregoing or following, $R^0$, $R^1$ and $R^2$ are each independently selected from —H, halogen, hydroxyl, nitro, nitrile, —$SOR^{11}$, —$S(O)_2R^{11}$, —$S(O)_2NR^{10}R^{12}$, —$OR^{11}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy.

In some embodiments, of any of the foregoing or following, $R^0$ is selected from hydroxyl, —$S(O)_2R^{11}$, —$S(O)_2NR^{10}R^{12}$, —$OR^{11}$, —$C(O)NR^{10}R^{12}$, —$NR^{10}R^{12}$, —$N(R^{12})C(O)R^{11}$, or —$NS(O)_2R^{12}$. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In some embodiments, of any of the foregoing or following, $R^1$ and $R^2$ are each independently selected from —H, halogen, hydroxyl, nitro, nitrile, —$OR^{11}$, substituted or unsubstituted $C_1$-$C_6$ alkyl, or substituted or unsubstituted $C_1$-$C_6$ haloalkyl, substituted or unsubstituted $C_1$-$C_6$ haloalkoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In some embodiments, of any of the foregoing or following, $R^1$ and $R^2$ are each independently selected from —H, methoxy, fluoro, chloro, bromo, hydroxyl, nitro, nitrile, methyl, trifluoromethyl, or trifluoromethoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In some embodiments, of any of the foregoing or following, $R^1$ and $R^2$ are each independently selected from H, methoxy, chloro, nitro, nitrile, or trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In some embodiments, of any of the foregoing or following, $R^1$ and $R^2$ are each trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^3$ is selected from —H, halogen, hydroxyl, nitro, nitrile, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In some embodiments of any of the foregoing or following, $R^3$ is selected from methyl, ethyl, propyl, isopropyl, cyclopropyl, or cyclobutyl. In certain embodiments, any of the foregoing may be optionally substituted.

In some embodiments of any of the foregoing or following, $R^3$ is selected from isopropyl, cyclopropyl, or cyclobutyl. In certain embodiments, any of the foregoing may be optionally substituted.

In some embodiments of any of the foregoing or following, $R^3$ is cyclobutyl. In certain embodiments, cyclobutyl may be optionally substituted.

In certain embodiments of any of the foregoing or following, $R^4$ is selected from —H, substituted or unsubstituted $C_1$-$C_6$ alkyl, substituted or unsubstituted cycloalkyl, substituted or unsubstituted aryl, substituted or unsubstituted heteroaryl, or substituted or unsubstituted arylalkyl.

In certain embodiments of any of the foregoing or following, $R^4$ is selected from —H, substituted or unsubstituted $C_1$-$C_6$ alkyl, substituted or unsubstituted cycloalkyl, substituted or unsubstituted aryl, or substituted or unsubstituted arylalkyl.

In some embodiments of any of the foregoing or following, $R^4$ is selected from methyl, ethyl, isopropyl, cyclopropyl, cyclobutyl, cyclopentyl, cyclohexyl, phenyl or benzyl. In certain embodiments, any of the foregoing may be optionally substituted.

In some embodiments of any of the foregoing or following, $R^4$ is methyl or isopropyl. In certain embodiments, any of the foregoing may be optionally substituted.

In some embodiments, of any of the foregoing or following, $R^4$ is methyl. In certain embodiments, methyl may be optionally substituted.

In certain embodiments of any of the foregoing or following, $R^5$, $R^6$ and $R^7$ are each independently selected from —H, —C(O)$R^1$, substituted or unsubstituted $C_1$-$C_6$ alkyl, substituted or unsubstituted cycloalkyl, substituted or unsubstituted aryl, substituted or unsubstituted arylalkyl, or $R^5$ is selected from any of the foregoing and $R^6$ and $R^7$ taken together with the nitrogen atom to which they are attached form a substituted or unsubstituted 3-6 membered ring.

In certain embodiments of any of the foregoing or following, $R^5$, $R^6$ and $R^7$ are each independently selected from —H, —C(O)$R^1$, substituted or unsubstituted $C_1$-$C_6$ alkyl, substituted or unsubstituted cycloalkyl, substituted or unsubstituted aryl, or substituted or unsubstituted arylalkyl.

In some embodiments of any of the foregoing or following, $R^5$, $R^6$ and $R^7$ are each independently selected from —H, methyl, ethyl, isopropyl, cyclopropyl, cyclobutyl, cyclopentyl, cyclohexyl, phenyl, benzyl, or $COCH_3$. In certain embodiments, any of the foregoing, except —H, may be optionally substituted.

In some embodiments of any of the foregoing or following, $R^5$, $R^6$ and $R^7$ are each independently selected from H, methyl, phenyl, or —$COCH_3$. In certain embodiments, any of the foregoing, except —H, may be optionally substituted.

In some embodiments of any of the foregoing or following, $R^5$ and $R^6$ are each independent selected from H, methyl or phenyl. In certain embodiments, any of the foregoing, except —H, may be optionally substituted.

In some embodiments of any of the foregoing or following, $R^7$ is H.

In some embodiments of any of the foregoing or following, the compound is selected from:

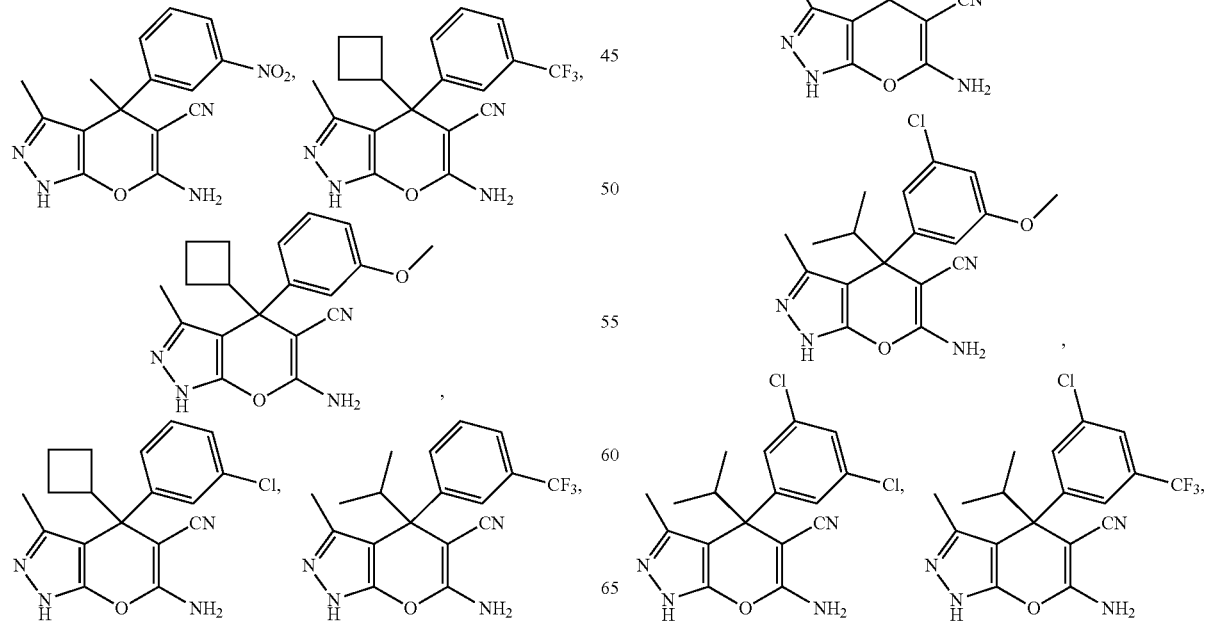

-continued

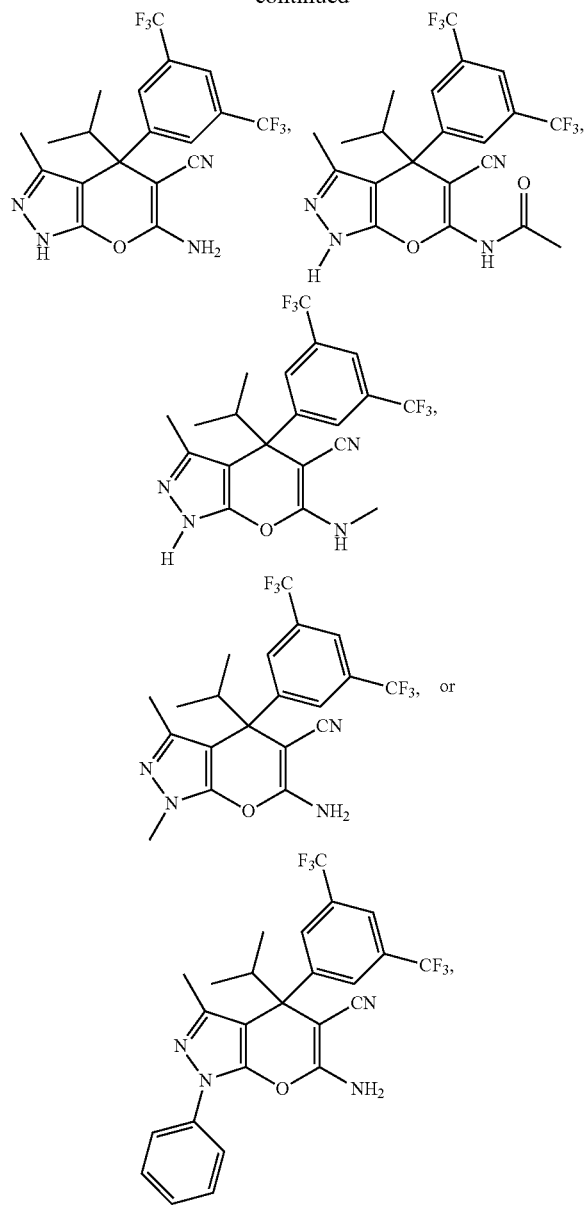

or a pharmaceutically acceptable salt thereof.

In certain embodiments of any of the foregoing or following, the compound is;

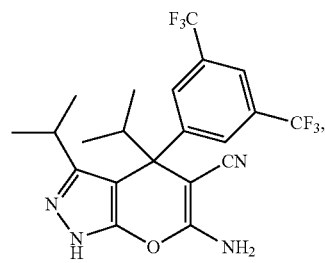 [SMILES: CC(C)c1n[nH]c2c1C(c1cc(C(F)(F)F)cc(C(F)(F)F)c1)(C(C)C)C(C#N)=C(N)O2]

or a pharmaceutically acceptable salt thereof.

In certain embodiments of any of the foregoing or following, the compound is:

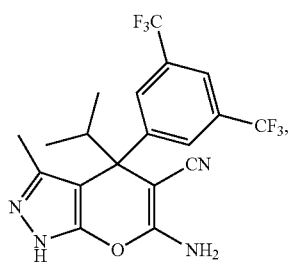 [SMILES: Cc1n[nH]c2c1C(c1cc(C(F)(F)F)cc(C(F)(F)F)c1)(C(C)C)C(C#N)=C(N)O2]

or an enantiomer thereof, or a pharmaceutically acceptable salt of any one of the foregoing. In certain such embodiment, the compound is:

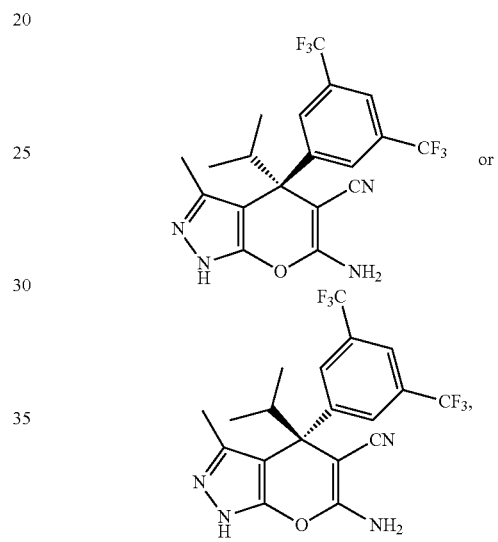

or a pharmaceutically acceptable salt thereof.

In certain embodiments of any of the foregoing or following, the disclosure provides a pharmaceutically acceptable salt thereof or an enantiomer thereof.

In certain embodiments of any of the foregoing or following, the $R^0$, $R^1$ and $R^2$ are not all simultaneously —H. In other embodiments, $R^0$ is —H and the ring to which it is attached, is substituted with a single substituent (other than —H) at one of $R^1$ or $R^2$. In certain embodiments, $R^0$ is —H, and $R^1$ and $R^2$ are not —H. In other embodiments, $R^1$ is —H and the ring to which it is attached is substituted with a single substituent (other than —H) at one of $R^0$ or $R^2$. In certain embodiments, $R^1$ is —H, and $R^0$ and $R^2$ are not —H. In other embodiments, $R^2$ is —H and the ring to which it is attached is substituted with a single substituent (other than —H) at one of $R^0$ or $R^1$. In certain embodiments, $R^2$ is —H, and $R^0$ and $R^1$ are not —H. In other embodiments, $R^0$, $R^1$ and $R^2$ are not —H.

In certain embodiments of any of the foregoing or following, compounds of Formula VI are inhibitors of SHMT, such as are capable of inhibiting an activity of an SHMT enzyme. In certain embodiments, compounds of Formula VI are SHMT2 inhibitors and, optionally, are also inhibitors of SHMT1. In certain embodiments, compounds of Formula VI are SHMT2 inhibitors, but do not inhibit SHMT1. In certain embodiments, compounds of Formula VI inhibit SHMT2 with an IC50 of less than 5000 nM and, optionally, inhibit SHMT1 with an IC50 of less than 5000 nM. In certain embodiments, compound of Formula VI inhibit SHMT2 with an IC50 of less than 2000 nM, less than 1500 nM, less than 800 nM, less than 500 nM, less than 250 nM, less than 150 nM, or less than 50 nM. In certain embodiments, such compounds also inhibit SHMT1 with an IC50 of less than 5000 nM. In certain embodiments, such compounds inhibit SHMT1 with an IC50 of less than 1000 nM, less than 750 nM, less than 500 nM, less than 250 nM, less than 100 nM, or less than 50 nM. In certain embodiments, the IC50 is measured in an in vitro assay, as described herein. In certain embodiments, compounds are selective inhibitors, as described herein.

In certain embodiments, compounds of Formula (VI) described using any combination of structural and/or functional activity, including any combination of one or more features described above or herein, are provided (and may be provided as an isolated or purified form or as a pharmaceutical composition). In certain embodiments, any such compounds of the disclosure may be used in any of the methods described herein, such as to inhibit SHMT activity in vitro or in vivo, or to treat cancer.

In another aspect, the disclosure provides a pharmaceutical composition for inhibiting the activity of a mammalian serine hydroxymethyl transferase (SHMT) enzyme, comprising a compound of Formula (VI) or a pharmaceutically acceptable salt thereof:

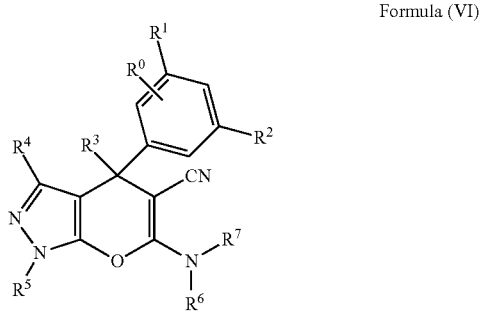

Formula (VI)

wherein:
$R^0$, $R^3$ and $R^2$ are each independently selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{10}$, —C(O)NR$^{10}$R$^{12}$, —NR$^{10}$R$^{12}$, —N(R$^{12}$)C(O)R$^{11}$, —NS(O)$_2$R$^{12}$ substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;
$R^3$ is selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;

$R^4$ is selected from H, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;
$R^5$, $R^6$ and $R^7$ are each independently selected from —H, —C(O)R$^{11}$, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl, or $R^5$ is selected from any of the foregoing and $R^6$ and $R^7$ taken together with the nitrogen atom to which they are attached form a substituted or unsubstituted 3-6 membered ring;
each occurrence of $R^{11}$ is independently selected from substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl, and
each occurrence of $R^{10}$ and $R^{12}$ is each independently selected from —H, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl, formulated in a pharmaceutically acceptable excipient or solvent.

In certain embodiments, the compound is represented by Formula (VIa) (wherein the R groups are as described above for Formula VI):

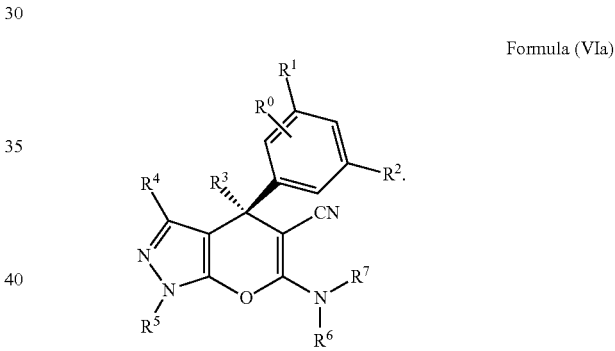

Formula (VIa)

In certain embodiments, the compound is represented by Formula (VIb) (wherein the R groups are as described above for Formula (VI)):

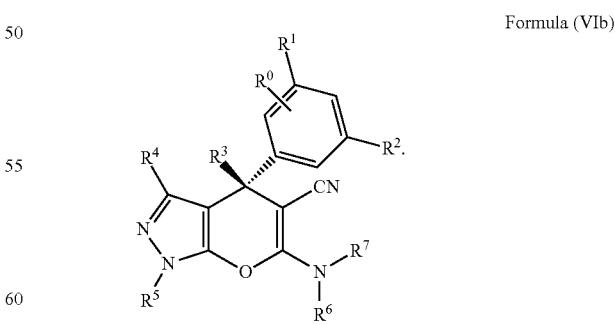

Formula (VIb)

In certain embodiments of any of the foregoing or following, $R^0$, $R^1$ and $R^2$ are each independently selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —C(O)OR$^{12}$, —C(O)R$^{11}$, —C(O)NR$^{10}$R$^{12}$, —NR$^{10}$R$^{12}$, —N(R$^{12}$)C(O)

$R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy.

In certain embodiments of any of the foregoing or following, $R^0$ is selected from hydroxyl, —$S(O)_2R^{11}$, —$S(O)_2NR^{10}R^{12}$, —$OR^{11}$, —$C(O)NR^{10}R^{12}$, —$NR^{10}R^{12}$, —$N(R^{12})C(O)R^{11}$, or —$NS(O)_2R^{12}$. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from —H, halogen, hydroxyl, nitro, nitrile, —$OR^{11}$, substituted or unsubstituted $C_1$-$C_6$ alkyl, or substituted or unsubstituted $C_1$-$C_6$ haloalkyl, substituted or unsubstituted $C_1$-$C_6$ haloalkoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from —H, methoxy, fluoro, chloro, bromo, hydroxyl, nitro, nitrile, methyl, trifluoromethyl, or trifluoromethoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from —H, methoxy, chloro, nitro, nitrile, or trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^3$ is selected from —H, halogen, hydroxyl, nitro, nitrile, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected from methyl, ethyl, propyl, isopropyl, cyclopropyl, or cyclobutyl. In certain embodiments, any of the foregoing may be optionally substituted.

In certain embodiments of any of the foregoing or following, $R^3$ is selected from isopropyl, cyclopropyl, or cyclobutyl. In certain embodiments, any of the foregoing may be optionally substituted.

In certain embodiments of any of the foregoing or following, $R^3$ is cyclobutyl. In certain embodiments, cyclobutyl may be optionally substituted.

In certain embodiments of any of the foregoing or following, $R^4$ is selected from —H, substituted or unsubstituted $C_1$-$C_6$ alkyl, substituted or unsubstituted cycloalkyl, substituted or unsubstituted aryl, substituted or unsubstituted heteroaryl, or substituted or unsubstituted arylalkyl.

In certain embodiments of any of the foregoing or following, $R^4$ is selected from —H, substituted or unsubstituted $C_1$-$C_6$ alkyl, substituted or unsubstituted cycloalkyl, substituted or unsubstituted aryl, or substituted or unsubstituted arylalkyl.

In certain embodiments of any of the foregoing or following, $R^4$ is selected from methyl, ethyl, isopropyl, cyclopropyl, cyclobutyl, cyclopentyl, cyclohexyl, phenyl or benzyl. In certain embodiments, any of the foregoing may be optionally substituted.

In certain embodiments of any of the foregoing or following, $R^4$ is methyl or isopropyl. In certain embodiments, any of the foregoing may be optionally substituted.

In certain embodiments of any of the foregoing or following, $R^4$ is methyl. In certain embodiments, methyl may be optionally substituted.

In certain embodiments of any of the foregoing or following, $R^5$, $R^6$ and $R^7$ are each independently selected from —H, —$C(O)R^{11}$, substituted or unsubstituted $C_1$-$C_6$ alkyl, substituted or unsubstituted cycloalkyl, substituted or unsubstituted aryl, substituted or unsubstituted arylalkyl, or $R^5$ is selected from any of the foregoing and $R^6$ and $R^7$ taken together with the nitrogen atom to which they are attached form a substituted or unsubstituted 3-6 membered ring.

In certain embodiments of any of the foregoing or following, $R^5$, $R^6$ and $R^7$ are each independently selected from —H, —$C(O)R^{11}$, substituted or unsubstituted $C_1$-$C_6$ alkyl, substituted or unsubstituted cycloalkyl, substituted or unsubstituted aryl, or substituted or unsubstituted arylalkyl.

In certain embodiments of any of the foregoing or following, $R^5$, $R^6$ and $R^7$ are each independently selected from —H, methyl, ethyl, isopropyl, cyclopropyl, cyclobutyl, cyclopentyl, cyclohexyl, phenyl, benzyl, or —$COCH_3$. In certain embodiments, any of the foregoing, except —H or —$COCH_3$, may be optionally substituted.

In certain embodiments of any of the foregoing or following, $R^5$, $R^6$ and $R^7$ are each independently selected from —H, methyl, phenyl, or —$COCH_3$. In certain embodiments, methyl and phenyl may be optionally substituted.

In certain embodiments of any of the foregoing or following, $R^5$ and $R^6$ are each independent selected from —H, methyl or phenyl. In certain embodiments, methyl or phenyl may be optionally substituted.

In certain embodiments of any of the foregoing or following, $R^7$ is —H.

In certain embodiments of any of the foregoing or following, the compound is selected from:

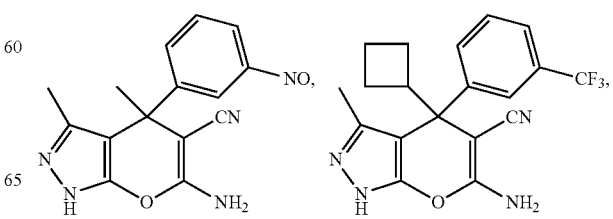

-continued
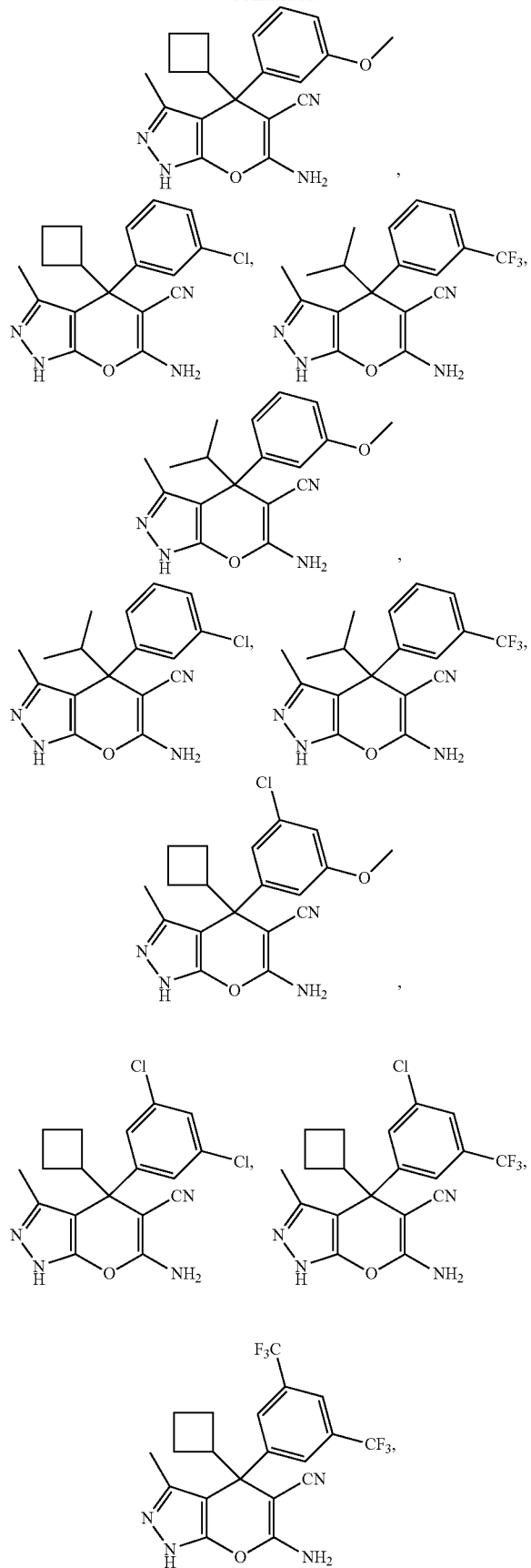
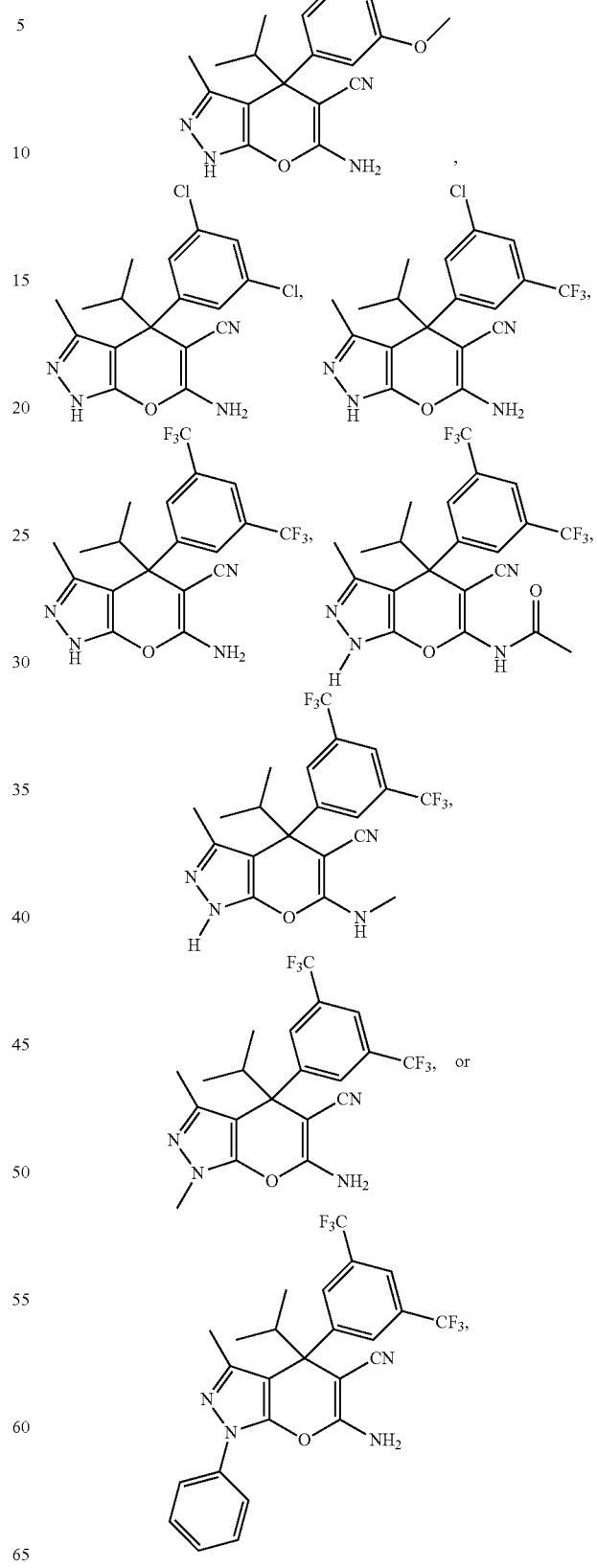
or a pharmaceutically acceptable salt thereof.

In certain embodiments of any of the foregoing or following, the compound is:

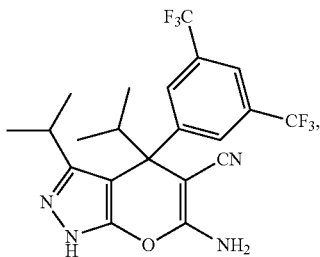 [SMILES: CC(C)c1n[nH]c2c1C(c1cc(C(F)(F)F)cc(C(F)(F)F)c1)(C(C)C)C(C#N)=C(N)O2]

or a pharmaceutically acceptable salt thereof.

In certain embodiments of any of the foregoing or following, the compound is:

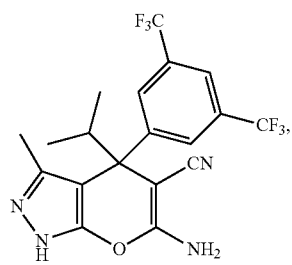 [SMILES: Cc1n[nH]c2c1C(c1cc(C(F)(F)F)cc(C(F)(F)F)c1)(C(C)C)C(C#N)=C(N)O2]

or an enantiomer thereof, or a pharmaceutically acceptable salt of any one of the foregoing. In certain such embodiment, the compound is:

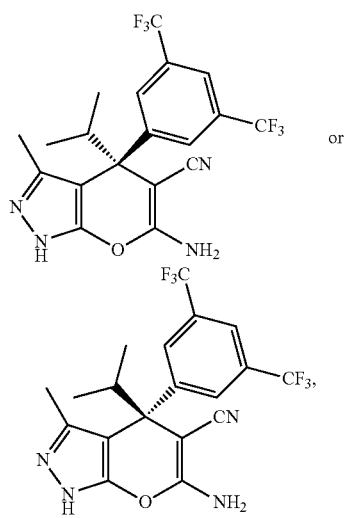

or a pharmaceutically acceptable salt thereof.

In certain embodiments of any of the foregoing or following, the disclosure provides a pharmaceutically acceptable salt thereof or an enantiomer thereof.

In certain embodiments of any of the foregoing or following, the $R^0$, $R^1$ and $R^2$ are not all simultaneously —H. In other embodiments, $R^0$ is —H and the ring to which it is attached, is substituted with a single substituent (other than —H) at one of $R^1$ or $R^2$. In certain embodiments, $R^0$ is —H, and $R^1$ and $R^2$ are not —H. In other embodiments, $R^1$ is —H and the ring to which it is attached is substituted with a single substituent (other than —H) at one of $R^0$ or $R^2$. In certain embodiments, $R^1$ is —H, and $R^0$ and $R^2$ are not —H. In other embodiments, $R^2$ is —H and the ring to which it is attached is substituted with a single substituent (other than —H) at one of $R^0$ or $R^1$. In certain embodiments, $R^2$ is —H, and $R^0$ and $R^1$ are not —H. In other embodiments, $R^0$, $R^1$ and $R^2$ are not —H.

In certain embodiments of any of the foregoing or following, when a moiety is characterized as "substituted," each substituent is for example, independently selected from a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, a cycloalkyl, an aralkyl, an aryl, or a heteroaryl.

The disclosure also provides variants of formulae (I), (II), (III), (IV), (V) and (VI), wherein

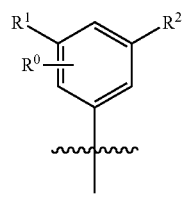

contains 1 to 3 heteroatoms (e.g., 1, 2 or 3 heteroatoms) independently selected from O or N.

The disclosure also provides variants of formulae (I), (II), (III), (IV), (V) and (VI), wherein,

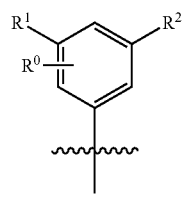

contains 1 to 3 heteroatoms (e.g., 1, 2 or 3 heteroatoms) independently selected from O or N.

Certain compounds of the disclosure (e.g., Compounds of formula (VIc), wherein formula (VIc) is a sub-genus of formula (VI)) and their corresponding inhibitory activity values are shown in Table A. The assay used to evaluate activity is described in the Examples.

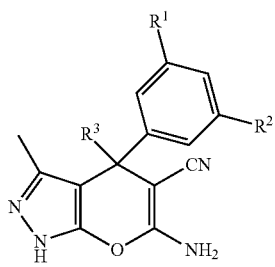

Formula (VIc)

TABLE A

| | $R^3$ | $R^2$ | $R^1$ | SHMT2 IC$_{50}$ (nM) | SHMT1 IC$_{50}$ (nM) |
|---|---|---|---|---|---|
| GD-07 | —CH$_3$ | —NO$_2$ | —H | >5000 | — |
| HK-1 | -cyclobutane | —CF$_3$ | —H | >5000 | — |
| HK-2 | -cyclobutane | —OMe | —H | >5000 | >5000 |
| HK-3 | -cyclobutane | —Cl | —H | 1191 | — |
| HK-4 | -cyclobutane | —CF$_3$ | —H | 1768 | — |
| HK-5 | —CH(CH$_3$)$_2$ | —CF$_3$ | —H | 756 | — |
| HK-6 | —CH(CH$_3$)$_2$ | —OMe | —H | 4580 | — |
| HK-7 | —CH(CH$_3$)$_2$ | —Cl | —H | 400.5 | — |
| HK-8 | —CH(CH$_3$)$_2$ | —CF$_3$ | —H | 400.5 | — |
| HK-9 | -cyclobutane | —Cl | —OMe | 3464 | — |
| HK-10 | -cyclobutane | —Cl | —Cl | 159.5 | — |
| HK-11 | -cyclobutane | —Cl | —CF$_3$ | 100 | — |
| HK-12 | -cyclobutane | —CF$_3$ | —CF$_3$ | 168 | 205.7 |
| HK-13 | —CH(CH$_3$)$_2$ | —Cl | —OMe | 500 | — |
| HK-14 | —CH(CH$_3$)$_2$ | —Cl | —Cl | 131 | 67 |
| HK-15 | —CH(CH$_3$)$_2$ | —Cl | —CF$_3$ | 35 | 20 |
| HK-16 | —CH(CH$_3$)$_2$ | —CF$_3$ | —CF$_3$ | 27 | 21 |
| HK-16 (PK-1) | —CH(CH$_3$)$_2$ | —CF$_3$ | —CF$_3$ | >5000 | >5000 |
| HK-16 (PK-2) | —CH(CH$_3$)$_2$ | —CF$_3$ | —CF$_3$ | 15 | 5 |

D. General Synthetic Methodology

The compounds of this disclosure may be prepared in general by methods known to those skilled in the art. Scheme 1 below illustrates a general synthetic route to the compounds of the present disclosure. Other equivalent schemes, which will be readily apparent to the ordinary skilled organic chemist, may alternatively be used to synthesize various portions of the molecules as illustrated by the general scheme below.

The synthesis of certain compounds of Formula (VI) disclosed herein is set forth in WO 2013/182472, which is herein incorporated by reference in its entirety. Compounds of Formulae I and VI can be prepared according to Scheme 1.

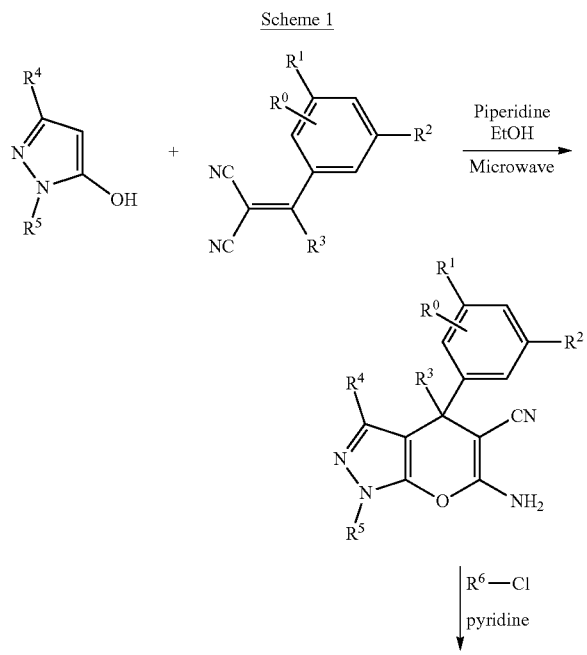

Scheme 1

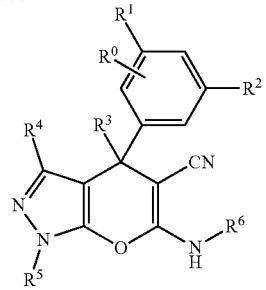

Additional exemplary synthetic schemes are set forth in the examples. By way of further example, exemplary compounds of formulae (II) and (III) can be prepared according to the protocols described in Journal of Heterocyclic Chemistry, 2005, 42, 6, p. 1111-1116). Exemplary compounds of Formula (IV) can be prepared according to the protocols described in U.S. Pat. No. 4,918,074, incorporated herein by reference.

E. Exemplary Uses

In certain aspects, compounds of the disclosure, such as compounds and compositions as described herein, can be used for a variety of in vitro or in vivo uses. In other words, in certain embodiments, mammalian SHMT inhibitors, such as SHMT2 inhibitors, such as inhibitors that inhibit both mammalian SHMT2 and SHMT1, can be used for a variety of in vitro and/or in vivo uses. Exemplary SHMT inhibitors are described herein. In certain embodiments, the SHMT2 inhibitor is a small organic molecule. In some embodiments, the SHMT2 inhibitor is not an antibody. Compounds of the disclosure (e.g., SHMT inhibitors, such as any of the inhibitors described herein based on structure and/or function) are suitable to inhibit SHMT activity, such as enzyme activity, in vitro or in vivo. In vitro uses include for studying SHMT function and/or serine flux and/or folate metabolism and/or NADPH generation and/or glycine generation in, for example, healthy cells, cancerous cells and/or in hypoxic cells. Similarly, folate metabolism, NADPH generation, and/or SHMT activity can be assessed in mutant cell lines, such as cells in which the activity of MTHFD1, MTHFD1L, MTHFD2, MTHFD2L, SHMT1, SHMT2, MTHFR, ALDH1L1, ALDHL2, SLC25A32 (also known as the mitochondrial folate transporter MFT), FH, KEAP1 is or has been inhibited, disregulated or knocked out, or cells having certain hyperactivating mutations in any of the foregoing or in NRF2. Evaluation of compounds in such mutant or knock out cell lines, or in cell lines harboring mutations affecting mitochondrial metabolism or a mitochondrial folate pathway is also useful for identifying cell types and cancer types in which compounds of the disclosure would be particularly useful, have increased anti-proliferative activity and/or improved activity at a lower dose. This can be seen in the examples.

In vivo uses include for studying SHMT activity and/or folate metabolism and/or serine flux and/or NADPH generation in animal models of disease, such as in animal cancer models, such as mouse xenografts. In certain embodiments, compounds of the disclosure are useful for evaluating the impact of hypoxic conditions to growth, survival and migration of cells, such as the tolerance of cells to hypoxic conditions. In certain embodiments, the cells or animal model comprise a mutation in Myc.

Suitable in vivo uses include to treat cancer or an autoimmune condition. For example, suitable in vivo uses include to treat a condition associated with SHMT activity and/or associated with alterations in mitochondrial metabolism, such as mitochondrial folate metabolism. For example, compounds of the disclosure, such as SHMT inhibitors, or such as any of the compounds described herein based on structure and/or function, are suitable for use in conditions in which increased mitochondrial activity is necessary or useful for disease progression, and/or SHMT expression or activity (e.g., SHMT2) is elevated in the disease state versus the healthy state and/or in which there is an alteration in mitochondrial metabolism, such as mitochondrial folate metabolism (e.g., via mutations or alterations in, for example, cancer cells). Exemplary genes or proteins that may be disregulated in, for example, cancer cells, are described above and include, for example, MTHFD1, MTHFD1L, MTHFD2, MTHFD2L, SHMT1, SHMT2, MTHFR, ALDH1L1, ALDHL2, SLC25A32 (also known as the mitochondrial folate transporter MFT), FH, KEAP1, and/or NRF2. Accordingly, the disclosure provides methods of treating cancer in a mammalian subject in need thereof, such as by inhibiting SHMT in a mammalian subject in need thereof, such as a subject with a condition associated with SHMT activity and/or associated with alterations in mitochondrial metabolism, such as mitochondrial folate metabolism. In certain embodiments, the method comprises administering a therapeutically effective amount of a compound of the disclosure. In certain embodiments, administration of the compound improves one or more symptoms of the disease or condition. In the case of cancer, such improvement in symptoms may include, for example, decrease in tumor size, decrease in disease progression, increased time to progression, increased overall patient survival, decrease in metastasis or decrease in time to metastasis, and the like. In certain embodiments, improvement in these symptoms is evaluated versus a control (e.g., an untreated patient or a patient receiving the standard of care).

Similarly, as demonstrated in the examples, compounds of the disclosure, such as SHMT inhibitors are useful to treat conditions in which there is a mutation or dysfunction in mitochondrial metabolism, such as a mitochondrial folate pathway. These may include activating mutations or upregulating of enzymes in the pathway. However, this may also include loss of function mutations that lead to dysregulation. Without wishing to be bound by theory, such dysregulation may sensitize cells to SHMT inhibitors, particularly inhibitors of the present disclosure capable of inhibiting both SHMT2 and SHMT1. Such conditions are not the only conditions in which compounds of the disclosure are effective (as shown herein). However, they may represent a category of conditions that are particularly sensitive to this approach.

In certain embodiments, the disclosure provides a method for treating cancer. In certain embodiments, the cancer is associated with SHMT activity. In certain embodiments, the method comprises administering an effective amount of a compound or composition of the disclosure, such as an SHMT2 inhibitor, such as any of the compounds described herein based on structure and/or function. SHMT inhibitors may be administered as a monotherapy or in combination with one or more additional agents or therapeutic modalities as part of a therapeutic regimen. In certain embodiments, administration of the compound (alone or as part of the therapeutic regimen) improves one or more symptoms of the disease or condition. In the case of cancer, such improvement in symptoms may include, for example, decrease in tumor size, decrease in pain, decrease in disease progression, increased time to progression, increased overall patient survival, decrease in metastasis or decrease in time to metastasis, and the like. In certain embodiments, improvement in these symptoms is evaluated versus a control (e.g., an untreated patient or a patient receiving the standard of care).

In certain embodiments, the disclosure provides a method for treating an autoimmune disorder. In certain embodiments, the autoimmune disorder is associated with SHMT activity. In certain embodiments, the method comprises administering an effective amount of a compound or composition of the disclosure, such as an SHMT2 inhibitor, or any of the inhibitors compounds herein based on structure and/or function. SHMT inhibitors may be administered as a monotherapy or in combination with one or more additional agents or therapeutic modalities as part of a therapeutic regimen. In certain embodiments, administration of the compound (alone or as part of the therapeutic regimen) improves one or more symptoms of the disease or condition. In the case of an autoimmune disorder, such improvement in symptoms may include, for example, decrease in inflammatory markers, decrease in inflammation, decrease in pain, increased mobility and/or range of motion, and improvements in patient reports on quality of life measures. The particular symptoms improved will vary based on the autoimmune condition. In certain embodiments, improvement in these symptoms is evaluated versus a control (e.g., an untreated patient or a patient receiving the standard of care).

In certain aspects, the disclosure contemplates that any of the compounds of the disclosure (and pharmaceutical compositions) may be used in any of the in vitro or in vivo methods provided herein. In certain embodiments, compounds of the disclosure are SHMT inhibitors and are suitable for inhibiting SHMT activity, such as SHMT2 and, optionally, SHMT1 activity. In certain embodiments, such compounds are suitable for modulating SHMT activity in vitro, such as to manipulate serine flux and/or folate metabolism. Such in vitro methods may be useful for identifying other components of folate metabolic pathways. In other embodiments, such compounds are suitable for modulating SHMT activity in vivo, such to treat a patient suffering from a SHMT-related condition or a condition that can be ameliorated by inhibiting SHMT activity and/or a condition associated with alterations in mitochondrial metabolism, such as mitochondrial folate metabolism, such as cancer and autoimmune disorders.

Moreover, any of the compounds of the disclosure may be formulated as a pharmaceutical composition comprising a compound and one or more acceptable carriers and/or excipients. Compositions, such as pharmaceutical compositions, may be used in any of the in vitro or in vivo methods described herein, such has to treat any one or more of the diseases or conditions described herein.

Accordingly, the disclosure contemplates methods of treating (decreasing the frequency or severity of or otherwise alleviating one or more symptoms of the condition) a subject in need thereof (e.g., a subject having any of the conditions described herein, including any of the autoimmune conditions described herein or any of the forms of cancer described herein) by administering a compound of the disclosure (e.g., SHMT inhibitors, such as any of the inhibitors described herein based on structure and/or function), such as an effective amount of a compound of the disclosure.

Cancers and Proliferative Disorders

In certain embodiments, compounds and compositions of the disclosure are useful to treat cancer, such as to reduce cancer cell growth, survival and/or metastasis. Such cancers include, for example, solid tumors and hematological malignancies (both adult and pediatric). Exemplary cancers include, but are not limited to, leukemia, lymphoma, lung cancer (including non-small lung cancer), mesothelioma, breast cancer (including other solid tumors of the breast), liver cancer (including other solid tumors of the liver), colon or colorectal cancer (including other solid tumors of the colon and/or rectum), stomach cancer (including other solid tumors of the stomach), prostate cancer (including other solid tumors of the prostate), pancreatic cancer (including other solid tumors of the pancreas), ovarian cancer (including other solid tumors of the ovary), solid tumors of the uterus or female genital tract, bladder cancer (including other solid tumors of the bladder), head and neck cancers, glioblastoma and other brain tumors, and trophoblastic neoplasms.

Although the high metabolic needs of cancer cells make all cancers good candidates for treatment with SHMT inhibitors, certain cancers may be particularly susceptible to treatment or may be sensitized to treatment due to their underlying mitochondrial activity or mutational status. By way of non-limiting example, in certain embodiments, the cancer comprises cells having a mutation affecting mitochondrial metabolism or the mitochondrial folate pathway. One class of cancers has high expression levels of SHMT2 or upregulation in a component of the mitochondrial folate pathway. However, other mutations may impair mitochondrial metabolism or the mitochondrial folate pathway (including mutations in SHMT2), and thus, sensitize cancers to SHMT inhibition. Examples of such sensitization are provided herein. Exemplary genes or proteins that may be disregulated in, for example, cancer cells, are described above and include, for example, MTHFD1, MTHFD1L, MTHFD2, MTHFD2L, SHMT1, SHMT2, MTHFR, ALDH1L1, ALDHL2, SLC25A32 (also known as the mitochondrial folate transporter MFT), FH, KEAP1, and/or NRF2.

Another class of cancers that may be particularly susceptible to treatment with an SHMT inhibitor are cancers comprising mutations that inactivate KEAP1 (either by, for example, somatic mutation or epigenetic silencing). Such mutations may result in aberrant NRF2 activity and nuclear function. Additionally or alternatively, suitable cancers may additionally have mutations in NRF2 itself with or without KEAP1 mutation. Cancers may additionally have alterations in mitochondrial metabolism including mutations to fumarate hydratase (FH) that lead to activation of NRF2. Loss of FH activity may potentiate cells to SHMT inhibitors by additional mechanisms as well. Without being bound by theory, cancers may have aberrant activation of NRF2 via other mechanisms. Aberrant NRF2 activation leads to altered transcription of mitochondrial and one carbon metabolism genes through the activity of ATF4. Activation of the 1c pathway and mitochondrial folate metabolism by NRF2 may also occur via ATF4 independent mechanisms.

Exemplary cancers with identified mutations in the KEAP1-NRF2-ATF4 pathway include non-small cell lung cancer, squamous cell lung carcinoma, prostate cancer, head and neck cancer (KEAP1 mutations, NRF2 mutations), hereditary papillary renal carcinoma, Hereditary leiomyomatosis and renal cell cancer (FH mutations). Furthermore, as described herein, there are identified cancers with elevated SHMT2 levels and/or mutations in other folate pathway components.

Without being bound by theory, the present disclosure provides methods for treating cancer and autoimmune conditions, such as cancers and conditions associated with alterations in mitochondrial folate metabolism. In some embodiments, particularly susceptible cancers or autoimmune conditions are those in which SHMT2 or another mitochondrial folate pathway enzyme or another gene is upregulated or activated. In other embodiments, particularly susceptible cancers or autoimmune conditions are those in which SHMT2 or another mitochondrial folate pathway component are knocked out or downregulated, thereby increasing the susceptibility of cells to treatment.

In certain embodiments, a compound of the disclosure is administered as a monotherapy. In other embodiments, compounds of the disclosure are used in combination with one or more other agents and/or therapeutic modalities (e.g., dietary regimen). When more than one agent is administered, the agents may be administered at the same or varying times, and by the same or differing routes of administration.

In certain embodiments, compounds of the disclosure are used in combination with the then current standard of care of the particular condition as part of a therapeutic regimen. In other embodiments, the therapeutic regimen includes one or more antifolates (e.g., other than a compound of the disclosure; an antifolate that is not selective for SHMT1 and/or SHMT2), such as traditional antifolates, such as methotrexate or pemetrexed or another compound that is an inhibitor of DHFR and/or TS. In other embodiments, the therapeutic regimen includes an additional anti-cancer agent, such as 5FU or other chemotherapeutic or radiotherapy regimen. In certain embodiments, the therapeutic regimen includes rescue therapy, such as leucovorin, formate or pharmaceutical salts, esters or derivatives of formate. In certain embodiments, rescue therapy refers to administration of leucovorin, formate and/or a pharmaceutical salt of formate. Without being bound by theory, use of rescue therapy to reduce toxicity and/or side effects may be used when SHMT inhibitors are used alone, as well as when they are used as part of a therapeutic regimen with one or more additional agents or therapeutic modalities. Rescue therapy is routinely used currently in patients receiving, for example, methotrexate. Accordingly, its use can be readily adapted to this context. For example, the dose of rescue therapy can be titered to decrease toxicity without abrogating therapeutic efficacy. Similarly, rescue therapy may be administered at the same time, prior to, or following administration of an SHMT inhibitor to manage any toxicity (if any) while maintaining an acceptable therapeutic profile. Similarly, when rescue therapy is combined with other agents as part of a therapeutic regimen, it can be administered at the same time, prior to, or following administration of a given other agent. In other embodiments, use of rescue therapy is unnecessary because the safety and toxicity profile is acceptable.

In certain embodiments, co-administration results in an additive or synergistic effect versus administration of at least one of the compounds alone. In certain embodiments, co-administration permits administration of a lower dose of the non-SHMT inhibitor compound (e.g., effectiveness is reached at a lower dose of, for example, methotrexate) or of a higher dose of the SHMT inhibitor or other agent by, for example, reducing side effects. In certain embodiments, the combination therapy improves the therapeutic window of one or both compounds or reduces side effects associated with one or both compounds.

In other embodiments, a compound of the disclosure is administered with a glycine containing composition. In other embodiments, the therapeutic regimen includes a dietary regimen, such as a regimen in which dietary levels of methionine, serine, and/or choline are reduced and/or dietary levels of glycine are increased.

In certain embodiments, the cancer is pancreatic cancer or colon cancer. In certain embodiments, the cancer is a cancer comprising (e.g., in which one or more cells of the tumor or cancer have) a mutation in the mitochondrial folate pathway. For example, in certain embodiments, the compounds of the disclosure, such as SHMT inhibitors are used to treat a cancer comprising a mutation in the mitochondrial folate pathway, such as mutation in mitochondrial serine hydroxymethyl transferase (SHMT2), mitochondrial methylene tetrahydrofolate dehydrogenase (MTHFD2), MTHFD1L or FH.

The disclosure contemplates combinations of any of the foregoing embodiments and aspects. In other words, the disclosure contemplates that any of the compounds of the disclosure, including any inhibitor of mammalian SHMT2 (and, in certain embodiments also SHMT1), may be used in any of the in vitro or in vivo methods, including methods of treatment. Moreover, such compounds and pharmaceutical compositions may be used as a monotherapy or as part of a therapeutic regimen with one or more other agents or treatment modalities, including but not limited to chemotherapy, anti-folate agent, rescue therapy, glycine, radiation therapy, nutritional therapy, and/or the standard of care for the particular cancer. Exemplary categories of compounds for use in treating cancer or autoimmune condition are, for example, Compounds of Formula VI, VIa, VIb, or any of the compounds described based on a combination of structural and/or functional characteristics herein.

Autoimmune Conditions

In other embodiments, the disclosure provides methods of treating an autoimmune condition by administering a compound of the disclosure. Such diseases or disorders include, but are not limited to, rheumatoid arthritis, multiple sclerosis, systemic lupus erythematosus, myasthenia gravis, inflammatory bowel disease (e.g., Crohn's disease or ulcerative colitis), polymyositis, dermatomyositis, inflammatory myositis, ankylosing spondolytis, and ulcerative colitis. Similar to as described above for cancer, autoimmune disorders, as well as other conditions, may be treated based on administering a compound of the disclosure as a monotherapy or as a combination therapy, as described above.

As noted above, in certain embodiments, compounds of the disclosure may be particularly suitable for use in subjects having one or more mutations that impact mitochondrial metabolism, as described above. Additionally or alternatively, in autoimmune conditions the mitochondrial folate pathway may be activated, and thus, compounds of the disclosure offer a mechanism for regulating this inappropriate activation or dysregulation of mitochondrial metabolism.

F. Compositions and Modes of Administration

In some embodiments of this disclosure, a compound of the present disclosure is formulated with one or more pharmaceutically acceptable carriers, excipients and/or solvents. The disclosure provides such compositions and pharmaceutical compositions. Any of the compounds of the disclosure may be provided in isolated or purified form and/or as a pharmaceutical composition. The compound may be formulated for administration in any convenient way for use in human medicine. Any compound of the disclosure or salt or enantiomer thereof can be provided as a composition, such as a pharmaceutical composition, such as a composition having any of the features described herein. Any such compound of the disclosure or composition of the disclosure may be used in any of the in vitro or in vivo methods described herein.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The characteristics of the carrier will depend on the route of administration. Each of the methods or uses of the present disclosure, as described herein, comprises administering to a mammal in need of such treatment or use an effective amount, such as a pharmaceutically or therapeutically effective amount, of a compound of the disclosure, or a pharmaceutically acceptable salt thereof. Compounds may be administered alone or in combination with other agents.

Compounds or pharmaceutical compositions of the disclosure may be administered to cells in vitro, such as by addition to culture media. Additionally or alternatively, compounds or pharmaceutical compositions may be administered to route of administration, such as oral, parenteral, intravenous, intra-arterial, cutaneous, subcutaneous, intramuscular, topical, intracranial, intraorbital, ophthalmic, intravitreal, intraventricular, intracapsular, intraspinal, intracisternal, intraperitoneal, intranasal, aerosol, central nervous system (CNS) administration, or administration by suppository. In some embodiments, the therapeutic methods of the disclosure include administering the composition of a compound topically, systemically, or locally. For example, therapeutic compositions of compounds of the disclosure may be formulated for administration by, for example, injection (e.g., intravenously, subcutaneously, or intramuscularly), inhalation or insufflation (either through the mouth or the nose) or oral, buccal, sublingual, transdermal, nasal, or parenteral administration. The compositions of compounds described herein may be formulated as part of an implant or device, or formulated for slow or extended release. When administered parenterally, e.g., by intravenous, cutaneous or subcutaneous injection, the therapeutic composition of compounds for use in this disclosure is preferably in a pyrogen-free, physiologically acceptable form.

A preferred pharmaceutical composition for intravenous, cutaneous, or subcutaneous injection should contain, in addition to the toxicity-reducing compounds, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the compound of the present disclosure may also contain stabilizers, preservatives, buffers, antioxidants, or other additives known to those of skill in the art. Techniques and formulations generally may be found in Remington's Pharmaceutical Sciences, Meade Publishing Co., Easton, Pa.

A composition comprising a compound of the present disclosure may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

When an effective amount of a compound(s) of the present disclosure is administered orally, compound(s) of the present disclosure may be in the form of a tablet, capsule, powder, solution or elixir. When administered in tablet form, the pharmaceutical composition may additionally contain a solid carrier such as a gelatin or an adjuvant. The tablet, capsule, and powder may contain from about 5 to 95% of a compound of the present disclosure, and preferably from about 10% to 90% of a compound of the present disclosure. When administered in liquid form, a liquid carrier such as water, petroleum, oils of animal or plant origin such as peanut oil, mineral oils, phospholipids, tweens, triglycerides, including medium chain triglycerides, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition typically contains from about 0.5 to 90% by weight of a compound of the present disclosure, and preferably from about 1 to 50% by weight of a compound of the present disclosure.

In solid dosage forms for oral administration (capsules, tablets, pills, dragees, powders, granules, and the like), one or more compositions comprising the compound of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the compound of the present disclosure, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

The pharmaceutical compositions may be in the form of a liposome or micelles in which the toxicity-reducing compounds are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

Suspensions, in addition to the active compounds may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The amount of compound(s) of the present disclosure in the pharmaceutical composition will depend upon the nature and severity of the condition being treated, on the amount of the compound of the present disclosure used, and on the nature of prior treatments the patient has undergone. Ultimately, the practitioner will decide the amount of the compound of the present disclosure with which to treat each individual patient. Representative doses of the present disclosure include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during one day, especially when relatively large amounts are deemed to be needed. It is contemplated that the various pharmaceutical compositions used to practice the methods of the present disclosure should contain about 0.1 µg to about 100 mg (preferably about 0.1 mg to about 50 mg, more preferably about 1 mg to about 2 mg) of compound per kg body weight.

The desired dose may conveniently be presented in a single dose or as divided doses administered at appropriate intervals, for example, as 2, 3, 4 or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

This disclosure will be better understood from the Experimental Details which follow. However, one skilled in the art will readily appreciate that the specific methods and results discussed are merely illustrative of the disclosure as described more fully in the embodiments which follow thereafter.

EXEMPLIFICATION

The subject matter of this disclosure now being generally described, it will be more readily understood by reference to the following examples which are included merely for purposes of illustration of certain aspects and embodiments of the present disclosure, and are not intended to limit the subject matter of this disclosure.

Example 1: Preparation of Compounds of Formula (I) or (VI)

The synthesis of certain compounds of formula (VI) disclosed herein is set forth in WO 2013/182472, which is herein incorporated by reference in its entirety. The compounds of formula (I) or (VI) can be prepared according to Scheme 1.

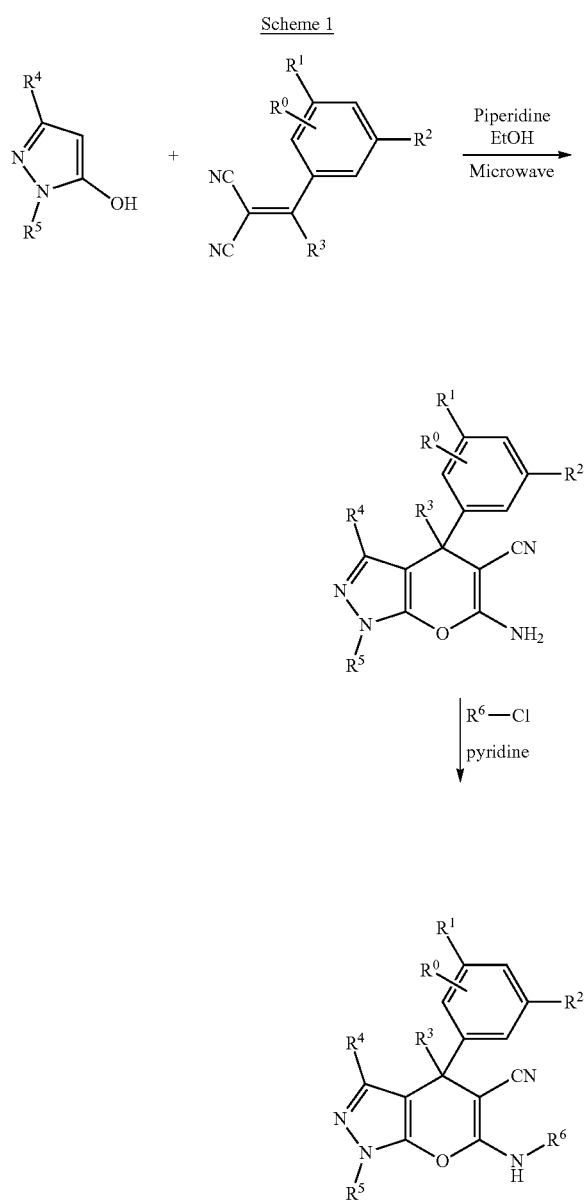

Example 2: Preparation of 5-(6-amino-5-cyano-4-isopropyl-3-methyl-1H-pyrano[2,3-c]pyrazol-4-yl)benzene-1,3-dicarbonitrile (6) via Scheme 2

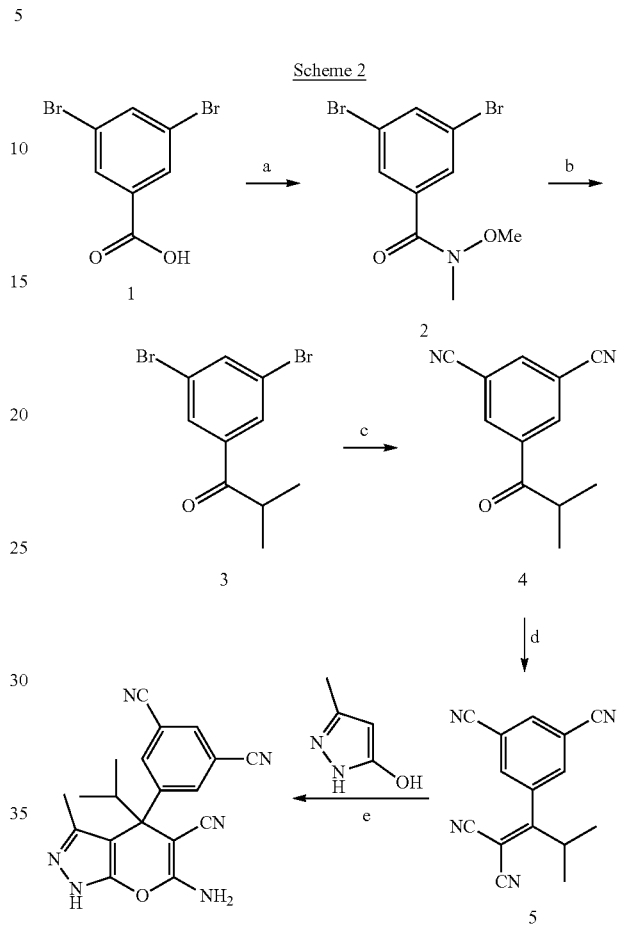

Scheme 2.

Reagents and conditions: (a) carbonyldiimidazole, methoxymethylamine, dichloromethane, room temperature, 18 h, (93%); (b) i-PrMgCl, Et$_2$O, room temperature, overnight (37%); (c) Zn(CN)$_2$, Zn, dppf, Pd(dba)$_2$, dioxane, 100° C., overnight (68%); (d) CHCl$_3$, malodinitrile, Ti(Cl)$_4$, pyridine, reflux, 48 h, (86%); (e) EtOH, dioxane, piperidine, 3 h, 65° C., (21%), A solution of 3,5-dibromobenzoic acid (1) (112 g, 0.4 mol) and carbonyldiimidazole (24 g, 149 mmol) in 1000 ml DCM was stirred at room temperature for 1 h. Methoxymethylamine (71.3 g, 0.44 mol) was added, and the mixture was stirred at room temperature for 18 h. Filtration was done and the filtrate was washed with saturated NaHCO$_3$ solution and brine, dried over anhydrous Na$_2$SO$_4$, filtered and the filtrate was evaporated to give 3,5-dibromo-N-1,5 methoxy-N-methyl-benzamide (2) (360 g, yield 93.1%). A solution of 3,5-dibromo-N-methoxy-N-methyl-benzamide (2) (60 g, 186 mmol) in 2 L anhydrous Et$_2$O was added i-PrMgCl (2M in Et$_2$O, 140 mL, 164 mmol) dropwise at room temperature under N$_2$ atmosphere. The mixture was stirred at room temperature overnight, then quenched with saturated NH$_4$Cl, extracted with EtOAc, washed with brine, dried over anhydrous Na$_2$SO$_4$, to give the crude product after concentration. The crude product was purified by column chromatography (Petrolether:EtOAc=200:1) to give 1-(3,5-dibromophenyl)-2-methyl-propan-1-one (3) (128 g, yield 37.4%). A solution of (3) (128 g, 417 mmol), Zn(CN)$_2$ (145 g, 1.25 mol), Zn (2.71 g, 41.7 mmol) and dppf (17.6 g, 31.3 mmol) in 2.5 l dioxane was flushed with N$_2$ for 10 min, then added Pd(dba)$_2$ (19.1 g, 20.9 mmol). The mixture was stirred at 100° C. overnight, filtered and evaporated. The resulting crude product was purified by silicon-gel column (Petrolether:EtOAc=5:1) to give 56 g of 5-(2-methylpropanoyl)benzene-1,3-dicarbonitrile (4) (yield: 67.8%). A solution of (4) (7.5 g, 38 mmol) was dissolved in chloroform (30 ml) and malodinitrile (10 g, 152 mmol), titaniumtetrachloride (1 M in CHCl$_3$; 38 ml, 38 mmol) and pyridine (6.1 ml, 76 mmol) was added. The solution is refluxed for 48 h. After cooling, the solution was added to 2N HCl (30 ml) and extracted with methylene chloride and the organic phase dried with sodium sulfate. After evaporation of the solvents to yield 8.0 g 5-[1 (dicyanomethylene)-2-methyl-propyl]benzene-1,3-dicarbonitrile (5) (86% yield) as colorless solid. A solution of (5) (2.2 g, 8.9 mmol) and 3-hydroxy-5-methylpyrazole (0.88 g, 8.9 mmol) in ethanol (6 ml) dioxane (6 ml) and piperidine (3 drops) was heated for 3 h at 65° C. in the microwave. After cooling water was added and extracted with ethylacetate. The organic phase was dried with sodium sulfate and the solvents evaporated. The residue was chromatographed on silica with cyclohexane/ethylacetate gradient to yield 0.66 g of 5-(6-amino-5-cyano-4-isopropyl-3-methyl-1H-pyrano[2,3-c]pyrazol-4-yl)benzene-1,3-dicarbonitrile (6) (21% yield) as colourless solid.

Further exemplified compounds of formula (I) or formula (VI) have been prepared in accordance to the general scheme 1 and 2 described above and their characterization data were listed in the Table B below.

TABLE B

| Compound | NMR (d$_6$-DMSO, 400 MHz), δ/ppm | LC-MS (m/z) |
|---|---|---|
| 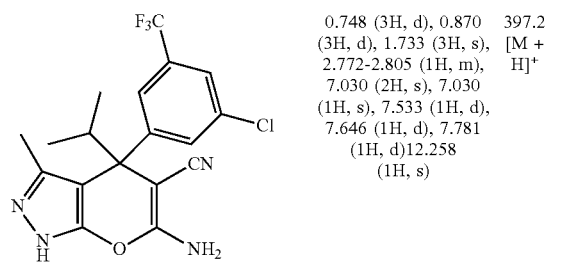 | 0.739 (3H, d), 0.863 (3H, d), 1.760 (3H, s), 2.698-2.731 (1H, m), 6.997 (2H, s), 7.291 (2h, d), 7.515 (1H, d), 12.238 (1H, s) | 363.1 [M]$^+$ |
| | 0.748 (3H, d), 0.870 (3H, d), 1.733 (3H, s), 2.772-2.805 (1H, m), 7.030 (2H, s), 7.030 (1H, s), 7.533 (1H, d), 7.646 (1H, d), 7.781 (1H, d)12.258 (1H, s) | 397.2 [M + H]$^+$ |

TABLE B-continued

| Compound | NMR (d$_6$-DMSO, 400 MHz), δ/ppm | LC-MS (m/z) |
|---|---|---|
| | 0.756 (3H, d), 0.876 (3H, d), 1.712 (3H, s), 2.836-2.9.2 (1H, m), 7.077 (2H, s, br), 7.896 (2H, d), 8.039 (1H, d), 0859 (1H, br) | 431.2 [M + H]$^+$ |
| | 0.564 (3H, d), 0.785 (3H, d), 0.895 (3H, d), 1.113 (3H, 2d); 2.231 (2H, m), 2.840 (1H, m), 7.072 (2H, s), 7.931 (2H, s), 8.046 (1H, s), 12.346 (1H, s) | 459.02 [M + H]$^+$ |

Enantiomers of compounds in this disclosure, when in a racemic mixture, can be separated and purified by chiral superfluid chromatography. For example, enantiomers of compound HK-16 was separated and purified on a preparative Chiralpak AD-H ((3×25 cm) column with the following conditions: mobile phase 10% isopropanol (0.1% diethylamine)/CO2 (100 bar); flow rate at 70 mL/min; UV detection at 254 nm with a sample concentration of 20 mg/mL with 1 mL/inj. Two Peaks were resolved and collected: Peak 1 (HK-16-P1) at 6.1 min and Peak 2 (HK-16-P2) at 7.3 min.

Example 3: Preparation of Compounds of Formula (II) or (III)

Exemplary compounds of formula (II) or (III) can be prepared according to Scheme 3.

Scheme 3

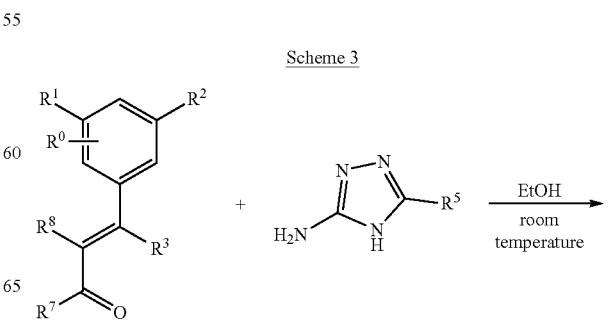

-continued

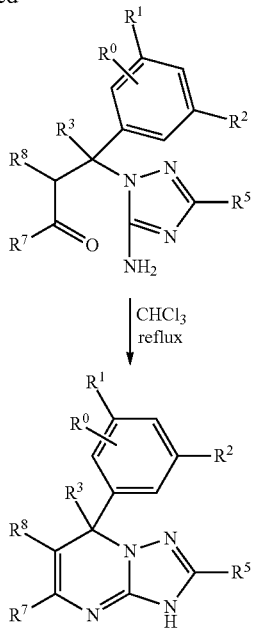

Exemplified compounds of formula (II) have been prepared in accordance to the general scheme 3 described above and their characterization data were listed in the Table C below.

TABLE C

| Compound | NMR (d$_6$-DMSO, 400 MHz), δ/ppm | LC-MS (m/z) |
|---|---|---|
| [structure with F$_3$C, CF$_3$, CN, NH$_2$, benzimidazole] | 1.103 (3H, t), 1.976-2.044 (2H, q), 3.360 (s, br), 6.993 (1H, m), 7.104 (3H, m), 7.142 (1H, d), 7.588 (1H, d), 8.026 (1H, s), 8.068 (2H, s), 9.041 (1H, br) | 452.2 [M + H]$^+$ |
| [structure with F$_3$C, CF$_3$, CN, NH$_2$, imidazopyrimidine] | 1.019 (3H, t), 1.890-1.942 (2H, q), 6.587 (1H, d), 7.169 (1H, d), 7.291 (1H, s), 8.029 (2H, s), 8.367 (3H, s), (1H, s) | 402.1 [M + H]$^+$ |

Example 4: Labeled dTTP ((2'-deoxythymidine 5'-triphosphate)

Using 2,3,3-$^2$H$_3$-serine (D3-serine) as a tracer, mitochondrial flux was measured by quantifying the labeling pattern of dTTP, a downstream product of dTMP. Two-labeled (M+2) dTTP can only arise from cytosolic flux, since 1C units from the mitochondria enter the cytosol as formate, which can only retain one deuterium (FIG. 1). As seen in FIG. 1(b), essentially all de novo dTTP is M+1, implying nearly all 1C units originate in the mitochondria. In contrast, most de novo dTTP in AMTHFD2 cells (cells engineered with a deletion in MTHFD2) is M+2, meaning its 1C units derive from the cytosolic pathway. This assay was used to examine mitochondrial serine flux and the effect of compounds of the disclosure on mitochondrial serine flux, in either wildtype or mutant cells.

An example of the use of this assay is depicted in FIG. 2(c). SHMT serine metabolic activity in SHMT2 expressing human cells is inhibited by HK-16, an inhibitor of SHMT2. Uniformly labeled serine is metabolized into various isoptomers in WT cells by the forward and reverse enzymatic activity of SHMT. This process is inhibited in cells by HK-16 in a dose-dependent manner.

Methods: Isotope Labeling Experiments:

HEK-293T cells were cultured in 6-well plates in Dulbecco's modified eagle media (DMEM) without pyruvate with 10% dialysed fetal bovine serum in 5% CO$_2$ at 37° C. Cells were treated with media containing uniformly labeled $^{13}$C serine or 2,2,3-$^2$H serine and, for inhibitor experiments, either DMSO (vehicle) or HK-16 (an inhibitor of SHMT2; racemic mixture or enatiomerically resolved). Growth was quenched and metabolites extracted by aspirating media, washing cells with cold PBS, and immediately adding MeOH/water (80:20 at −80° C.). Supernatants from two rounds of extraction were combined, dried under N$_2$, resuspended in water, placed in a 4° C. autosampler, and analyzed by reverse-phase ion-paring chromatography negative-mode electrospray-ionization high-resolution MS on a stand-alone orbitrap.

Deletion Cell Lines:

HEK293T cell lines mutant for SHMT1 and SHMT2 were created using the CRISPR-Cas9 system following standard published protocols. Single clones from successful transfections were grown up, genotyped and characterized.

Example 5: Measurement of 5-Aminoimidazole-4-carboxamide Ribonucleotide (AICAR)

Generation of AICAR provides an assay to evaluate one-carbon unit stress. Inhibition of SHMT2 in cells decreases serine metabolism and leads to one-carbon stress. FIG. 2(a) shows results from experiments using genetically engineered SHMT2 deletion cell lines. Such cells show high constitutive levels of 5-aminoimidazole-4-carboxamide ribonucleotide (AICAR), a marker for one-carbon unit stress, when cultured in media (left bar in FIG. 2(a)). This can be rescued by exogenous treatment with sodium formate (right bar in FIG. 2(a)).

FIG. 2(b) summarizes experiments using an inhibitor of SHMT2, HK-16. Human cells expressing SHMT2 were treated with control or increasing concentrations of HK-16. Treatment of human cells expressing SHMT2 for 24 hours with HK-16, an inhibitor of SHMT2, resulted in AICAR accumulation in a dose-dependent manner. (*) indicates AICAR was below the limit of detection.

Generation of AICAR provides an assay for evaluating compounds of the disclosure. Compounds of the disclosure were evaluated in such an assay.

Example 6: Inhibition of Human SHMT

We evaluated selective inhibition of human SHMT by racemic pyrazolopyran compounds. As depicted in FIG. 3(a), a pyrazolopyran referred to as GD07 showed weak inhibitory activity against recombinant human SHMT2 in an in vitro coupled enzymatic assay as measured at a single time point. Activity of additional compounds was evaluated. In FIG. 3(b), inhibition of human SHMT2 activity (using calculated percent inhibition) of several compounds was evaluated in an in vitro assay. The compounds depicted are: HK-2, HK-12, HK-14, HK-15, and HK-16.

Of note, these compounds are selective for SHMT. These compounds that show activity against SHMT2 in vitro do not inhibit human MTHFD2 in enzymatic assays (see FIG. 3(c) for data for HK-2, HK-15 and HK-16).

Description of Other Tested Compounds:

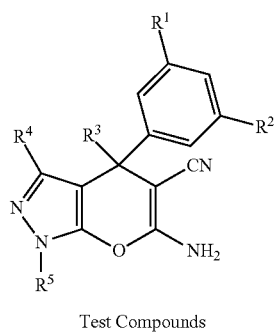

Test Compounds and 4% DMSO. Inhibition of initial reaction velocity was determined by adding various inhibitors at different concentrations and monitored as described. IC50 were calculated based on this assay.

For the MTHFD2 in vitro assay (FIG. 3(c)), the rate of NADH formation was directly monitored at 340 nm. The reaction conditions was started by addition of 0.125 μM (final) of 5,10 methylene tetrahydrofolate to MTHFD2 (2.5 mcg/mL), 50 mM potassium phosphate (pH 7.4), 7.5 mM dithiothreitol, 1.25 mM $NAD^+$, and 4% DMSO.

Example 7: Pyrazolopyran Inhibitors are Enantiomerically Specific

Compound HK-16 was enantiomerically resolved by HPLC into two pure fractions, "Peak 1" and "Peak 2". The anti-SHMT2 activity of HK-16 was confined to the enantiomer represented by "Peak 2" (PK-2) (FIG. 4(a)). The enantiomer in "Peak 2" was also active against SHMT1 in an in vitro enzyme assay (FIG. 4(b)). The assays for reaction rate are as described in Example 6.

Example 8: Inhibition of Human Cell Growth

Inhibitors of SHMT were evaluated in cells in culture, such as transformed cells or cancerous cells, to evaluate inhibition of cell growth. As depicted in FIG. 5, enantiomerically pure HK-16 inhibited cell growth in HEK293T cells in

| | $R^5$ | $R^4$ | $R^3$ | $R^2$ | $R^1$ | SHMT2 $IC_{50}$ (nM) | SHMT1 $IC_{50}$ (nM) |
|---|---|---|---|---|---|---|---|
| GD-07 | —H | —$CH_3$ | —$CH_3$ | —$NO_2$ | —H | >5000 | — |
| HK-1 | —H | —$CH_3$ | -cyclobutane | —$CF_3$ | —H | >5000 | — |
| HK-2 | —H | —$CH_3$ | -cyclobutane | —OMe | —H | >5000 | >5000 |
| HK-3 | —H | —$CH_3$ | -cyclobutane | —Cl | —H | 1191 | — |
| HK-4 | —H | —$CH_3$ | -cyclobutane | —$CF_3$ | —H | 1768 | — |
| HK-5 | —H | —$CH_3$ | —$CH(CH_3)_2$ | —$CF_3$ | —H | 756 | — |
| HK-6 | —H | —$CH_3$ | —$CH(CH_3)_2$ | —OMe | —H | 4580 | — |
| HK-7 | —H | —$CH_3$ | —$CH(CH_3)_2$ | —Cl | —H | 400.5 | — |
| HK-8 | —H | —$CH_3$ | —$CH(CH_3)_2$ | —$CF_3$ | —H | 400.5 | — |
| HK-9 | —H | —$CH_3$ | -cyclobutane | —Cl | —OMe | 3464 | — |
| HK-10 | —H | —$CH_3$ | -cyclobutane | —Cl | —Cl | 159.5 | — |
| HK-11 | —H | —$CH_3$ | -cyclobutane | —Cl | —$CF_3$ | 100 | — |
| HK-12 | —H | —$CH_3$ | -cyclobutane | —$CF_3$ | —$CF_3$ | 168 | 205.7 |
| HK-13 | —H | —$CH_3$ | —$CH(CH_3)_2$ | —Cl | —OMe | 500 | — |
| HK-14 | —H | —$CH_3$ | —$CH(CH_3)_2$ | —Cl | —Cl | 131 | 67 |
| HK-15 | —H | —$CH_3$ | —$CH(CH_3)_2$ | —Cl | —$CF_3$ | 35 | 20 |
| HK-16 | —H | —$CH_3$ | —$CH(CH_3)_2$ | —$CF_3$ | —$CF_3$ | 27 | 21 |
| HK-16 (PK-1) | —H | —$CH_3$ | —$CH(CH_3)_2$ | —$CF_3$ | —$CF_3$ | >5000 | >5000 |
| HK-16 (PK-2) | —H | —$CH_3$ | —$CH(CH_3)_2$ | —$CF_3$ | —$CF_3$ | 15 | 5 |
| KDG-4 | —$CH_3$ | —$CH_3$ | —$CH(CH_3)_2$ | —$CF_3$ | —$CF_3$ | >5000 | >5000 |
| KDG-5 | phenyl | —$CH_3$ | —$CH(CH_3)_2$ | —$CF_3$ | —$CF_3$ | >5000 | >5000 |
| KDG-12 | —H | —$CH(CH_3)_2$ | —$CH(CH_3)_2$ | —$CF_3$ | —$CF_3$ | 71 | 9.3 |

Note
for some compounds, activity was only tested against SHMT2, and thus, no data for SHMT1 is provided.

Enzymatic Assays:

For the SHMT1 and SHMT2 in vitro enzymatic assays (FIGS. 3(a) and 3(b)), the rate of 5,10-methylene tetrahydrofolate formation catalyzed by SHMT1/2 was indirectly evaluated by coupling with excess MTHFD2, which converts $NAD^+$ to NADH allowing for reaction monitoring by absorption at 340 nm. The reaction was started by addition of serine (1 mM final) to either human SHMT1 or human SHMT2 (2 mcg/mL), and human MTHFD2 (25 mcg/mL) in a buffer of 50 mM potassium phosphate (pH 7.4), 0.3 mM tetrahydrofolate, 7.5 mM dithiothreitol, 1.25 mM $NAD^+$, culture. Specifically, the growth of these human cells was not inhibited by Peak 1 (FIG. 5(a)) but was inhibited by Peak 2 (FIG. 5(b)).

Cell Growth Assays:

HEK293T cells were cultured in 96-well plates in Dulbecco's modified eagle media (DMEM) without pyruvate with 10% dialysed fetal bovine serum (Invitrogen) in 5% $CO_2$ at 37° C. 24 hours after plating, cells were treated with various concentrations of inhibitor. Growth was serially assessed using the resazurin ('AlamarBlue') assay.

Example 9: Inhibition of Cell Growth in Human Embryonic Kidney Cells

Inhibitors of SHMT were evaluated in wildtype, SHMT2 knock-out, and MTHFD2 knock-out 293T cells (FIG. 6(a) and FIG. 6(b)). Peak 2 of enantiomerically pure HK-16 inhibited cell growth in all three cell types tested (See FIG. 6(a)). Inhibition at a lower concentration of HK-16 compound was observed in the 293T cells having mutations in mitochondrial folate pathway (e.g., mutations or deficiencies in a mitochondrial folate enzyme), including the SHMT2 knock out cells and the MTHFD2 knock out cells. Cell lines deficient in a component of the mitochondrial folate pathway, such as deficient in a mitochondrial folate enzyme (generated using CRISPR-Cas9 editing) had increased sensitivity to inhibition by HK-16-P2.

Activity of Peak 1 of HK-16 was also evaluated. The compound showed little or no activity against wild type 293T cells. Some, although a lower degree of activity was observed with the highest dose of Peak 1 compound when tested against the knock out cell lines.

Example 10: Inhibition of Cancer Cell Growth

Inhibitors of SHMT were evaluated in various cancer cell lines. In this example, HK-16-P2 demonstrated inhibition in both the pancreatic cancer cell line 8988T and the human colon carcinoma cell line HCT116. As shown in FIGS. 7(a) and 7(b), enantiomerically pure HK-16 compounds were tested and revealed different inhibition properties against these cancer cell lines. HK-16-P2 (Peak 2) inhibited growth of both cell lines (FIG. 7a). Interestingly, the 8988T pancreatic cancer cell line was more sensitive to HK-16 (peak 2) and was sensitive at a lower dose of compound. This cancer cell line comprises (harbors) a mutation in a component of the mitochondrial folate pathway. Specifically, one or more cells in this line comprise a mutation in the downstream mitochondrial folate enzyme, MTHFD1L.

Cell Growth Assays

Example 11: Rescue Effect in Human Cells Treated with SHMT Inhibitors

Application of formate was shown to rescue the antigrowth effect in human cells treated with SHMT inhibitors. As shown in FIG. 8, the rescue effect of formate in cells treated with the SHMT2 inhibitor, HK-16 (peak 2) was demonstrated in wild-type HEK293T cells treated with pyrazolopyran compounds, specifically HK-16-P2 (Peak 2). The inhibitory effects of compound HK-16-P2 (Peak 2) at 10 µM in HEK293T cells were rescued upon co-culturing cells with formate at 1 mM. This example indicates that, akin to its use in anti-folate therapy, rescue with formate and formate related compounds may be suitable to help limit or decrease side effects that may be associated with SHMT inhibitors.

The described cell lines used in Examples 9-11 were cultured in 96-well plates in Dulbecco's modified eagle media (DMEM) without pyruvate (CELLGRO) with 10% dialysed fetal bovine serum (Invitrogen) in 5% CO2 at 37° C. Approximately 2,500 cells were plated in each well in 90 uL of media. After 24 hours cells were treated with various concentrations of inhibitor (time=0 hours), with or without formate. Growth was assessed at multiple time points (time=0, 24, 48, 72 hours) through measurement of fluorescence at 595 nm (excitation at 535 nm) on a BioTek micro titer plate reader after incubation with resazurin (0.01 mg/mL for 1.5 hours). IC50 curves were generated from percent inhibition of growth at 72 hours.

All publications and patents cited herein are hereby incorporated by reference in their entirety.

Those skilled in the art will recognize, or be able to ascertain using no more than routine experimentation, many equivalents to the specific embodiments of the disclosure described herein. Such equivalents are intended to be encompassed by the following claims.

We claim:

1. A method for treating cancer, comprising administering to a mammalian subject in need thereof an effective amount of a serine hydroxymethyl transferase (SHMT) inhibitor, and an anti-folate compound.

2. The method of claim 1, wherein the method further comprises administering a rescue therapy.

3. A method for treating cancer, comprising administering to a mammalian subject in need thereof an effective amount of a serine hydroxymethyl transferase (SHMT) inhibitor, an anti-folate compound and a rescue therapy, wherein the rescue therapy comprises formate, formate salt, formate ester, or leucovorin.

4. A method for treating a hematological malignancy, comprising administering to a mammalian subject in need thereof an effective amount of a compound of Formula (VI), or a pharmaceutically acceptable salt thereof:

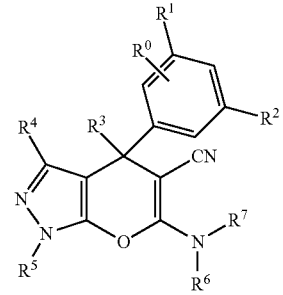

Formula (VI)

wherein:

$R^0$, $R^1$ and $R^2$ are each independently selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{11}$, —NS(O)$_2$R$^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;

$R^3$ is selected from isopropyl, cyclopropyl, or cyclobutyl;

$R^4$ is selected from —H, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

$R^5$, $R^6$ and $R^7$ are each independently selected from —H, —C(O)R$^{11}$, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl, or $R^5$ is selected from any of the foregoing and $R^6$ and $R^7$ taken together with the nitrogen atom to which they are attached form a substituted or unsubstituted 3-6 membered ring;

each occurrence of $R^{11}$ is independently selected from substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl; and each occurrence of $R^{10}$ and $R^{12}$ is each independently selected from H, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

5. The method according to claim 4, wherein the compound is represented by Formula (VIa):

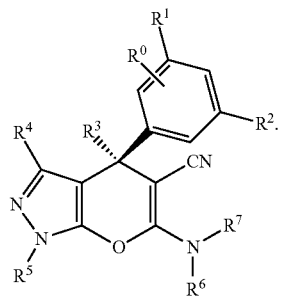

Formula (VIa)

6. The method according to claim 4, wherein the compound is represented by Formula (VIb):

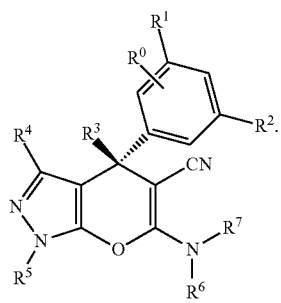

Formula (VIb)

7. The method according to claim 4, wherein $R^0$ is selected from hydroxyl, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, or —NS(O)$_2$R$^{12}$.

8. The method according to claim 4, wherein $R^1$ and $R^2$ are each independently selected from —H, halogen, hydroxyl, nitro, nitrile, —OR$^{11}$, substituted or unsubstituted $C_1$-$C_6$ alkyl, or substituted or unsubstituted $C_1$-$C_6$ haloalkyl, substituted or unsubstituted $C_1$-$C_6$ haloalkoxy.

9. The method according to claim 4, wherein $R^4$ is selected from methyl, ethyl, isopropyl, cyclopropyl, cyclobutyl, cyclopentyl, cyclohexyl, phenyl or benzyl.

10. The method according to claim 4, wherein $R^5$, $R^6$ and $R^7$ are each independently selected from —H, methyl, ethyl, isopropyl, cyclopropyl, cyclobutyl, cyclopentyl, cyclohexyl, phenyl, benzyl, or —COCH$_3$.

11. The method according to claim 4, wherein $R^7$ is —H.

12. The method according to claim 4, wherein the compound is selected from:

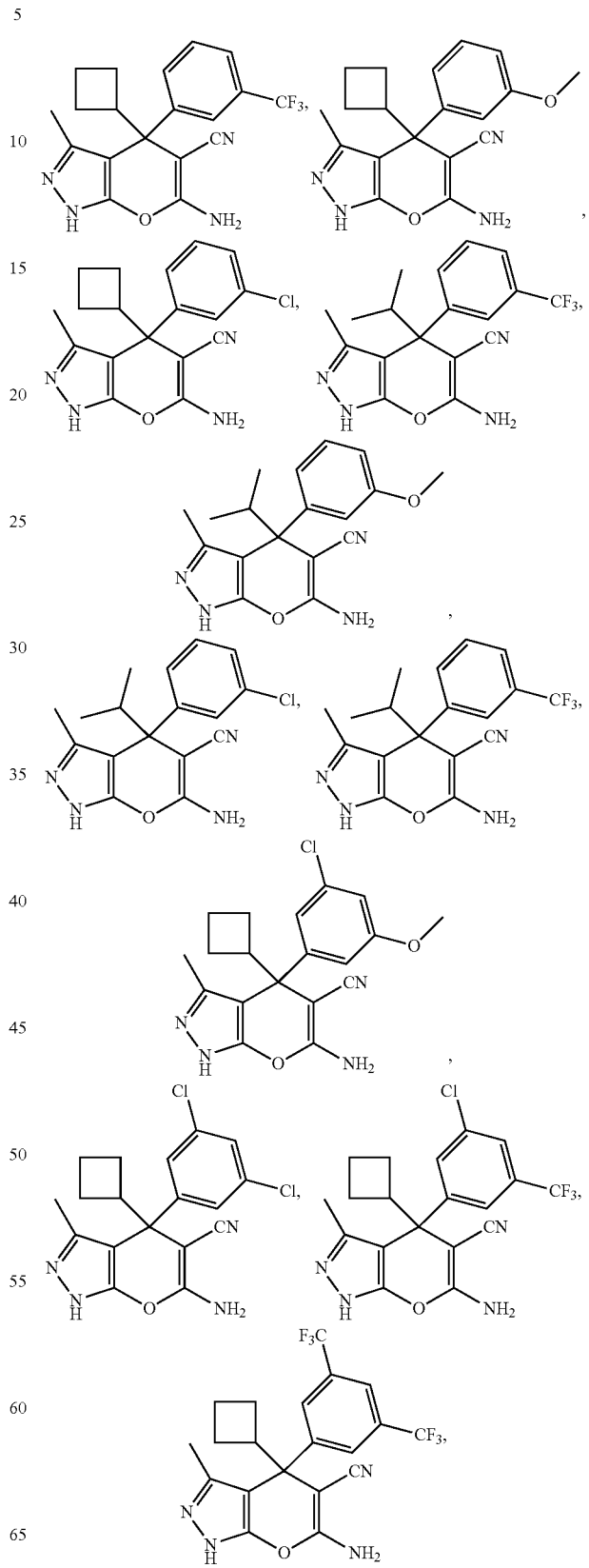

-continued

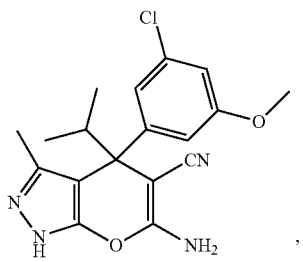

,

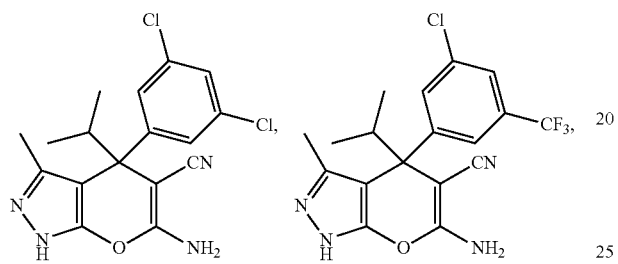

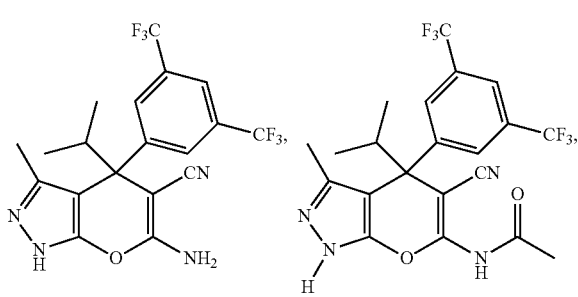

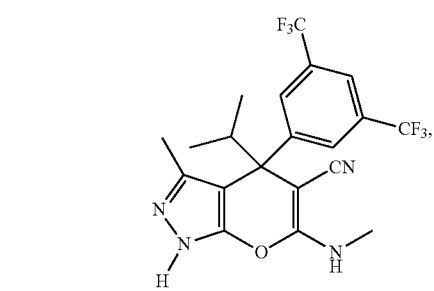

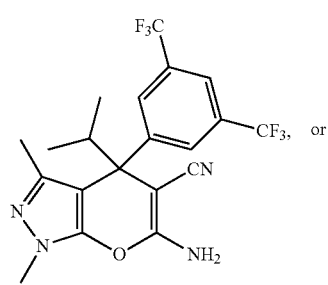 or

-continued

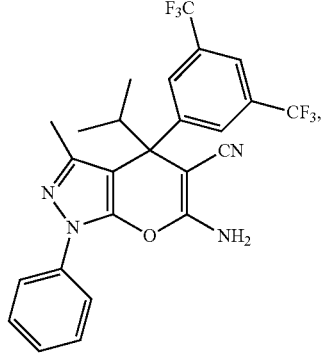

or a pharmaceutically acceptable salt thereof.

13. The method of claim 12, wherein the compound is:

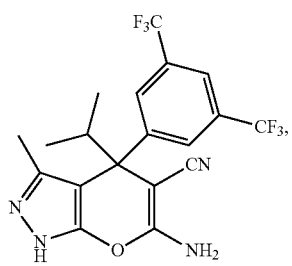

or a pharmaceutically acceptable salt thereof.

14. The method according to claim 4, wherein the compound is:

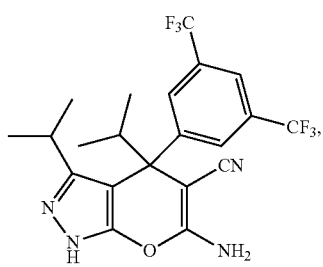 [SMILES: CC(C)c1n[nH]c2c1C(c1cc(C(F)(F)F)cc(C(F)(F)F)c1)(C(C)C)C(C#N)=C(N)O2]

or a pharmaceutically acceptable salt thereof.

15. The method according to claim 4, wherein the method further comprises administering an additional anti-cancer agent.

16. The method according to claim 15, wherein the additional anti-cancer agent is an anti-folate compound.

17. The method according to claim 4, wherein the compound of Formula (VI) is administered as part of a therapeutic regimen including one or more additional agents or treatment modalities.

18. The method according to claim 2, wherein the rescue therapy is a formate salt or folinic acid.

19. A method for treating a hematological malignancy, comprising administering to a mammalian subject in need thereof an effective amount of a compound of Formula (VI), or a pharmaceutically acceptable salt thereof:

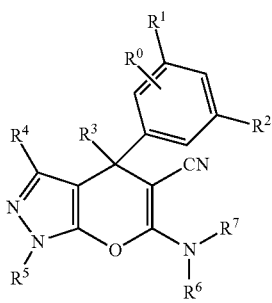

Formula (VI)

wherein:
R⁰, R¹ and R² are each independently selected from —H, halogen, hydroxyl, nitro, nitrile, —SOR¹¹, —S(O)₂R¹¹, —S(O)₂NR¹⁰R¹², —OR¹¹, —OC(O)R¹², —C(O)OR¹², —C(O)R¹¹, —C(O)NR¹⁰R¹², —NR¹⁰R¹², —N(R¹²)C(O)R¹¹, —NS(O)₂R¹², substituted or unsubstituted C₁-C₆ alkyl, substituted or unsubstituted cycloalkyl, substituted or unsubstituted heterocyclyl, substituted or unsubstituted aryl, substituted or unsubstituted heteroaryl substituted or unsubstituted arylalkyl, substituted or unsubstituted heteroarylalkyl, substituted or unsubstituted C₁-C₆ haloalkyl, or substituted or unsubstituted C₁-C₆ haloalkoxy;

R³ is selected from halogen, hydroxyl, nitro, nitrile, —SOR¹¹, —S(O)₂R¹¹, —S(O)₂NR¹⁰R¹², —OR¹¹, —OC(O)R¹², —C(O)OR¹², —C(O)R¹¹, —C(O)NR¹⁰R¹², —NR¹⁰R¹², —N(R¹²)C(O)R¹¹, —NS(O)₂R¹², substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted C₁-C₆ haloalkyl, or substituted or unsubstituted C₁-C₆ haloalkoxy;

R⁴ is selected from —H, substituted or unsubstituted C₁-C₆ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

R⁵, R⁶ and R⁷ are each independently selected from —H, —C(O)R¹¹, substituted or unsubstituted C₁-C₆ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl, or R⁵ is selected from any of the foregoing and R⁶ and R⁷ taken together with the nitrogen atom to which they are attached form a substituted or unsubstituted 3-6 membered ring;

each occurrence of R¹¹ is independently selected from substituted or unsubstituted C₁-C₆ alkyl, substituted or unsubstituted cycloalkyl, substituted or unsubstituted heterocyclyl, substituted or unsubstituted aryl, or substituted or unsubstituted heteroaryl; and each occurrence of R¹⁰ and R¹² is each independently selected from H, substituted or unsubstituted C₁-C₆ alkyl, substituted or unsubstituted cycloalkyl, substituted or unsubstituted heterocyclyl, substituted or unsubstituted aryl, or substituted or unsubstituted heteroaryl.

20. The method of claim 1, wherein the anti-folate compound is methotrexate or pemetrexed.

21. The method of claim 3, wherein the anti-folate compound is methotrexate or pemetrexed.

22. The method of claim 1, wherein the SHMT inhibitor is administered following administration of the anti-folate compound.

23. The method of claim 20, wherein the SHMT inhibitor is administered following administration of methotrexate or pemetrexed.

* * * * *